United States Patent
Li et al.

(10) Patent No.: US 11,744,900 B2
(45) Date of Patent: *Sep. 5, 2023

(54) PREPARATION OF MAYTANSINOID ANTIBODY CONJUGATES BY A ONE-STEP PROCESS

(71) Applicant: ImmunoGen, Inc., Waltham, MA (US)

(72) Inventors: Xinfang Li, Newton, MA (US); Jared M. Worful, Pittsburgh, PA (US)

(73) Assignee: IMMUNOGEN, INC., Waltham, MA (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/371,151

(22) Filed: Jul. 9, 2021

(65) Prior Publication Data

US 2022/0133899 A1 May 5, 2022

Related U.S. Application Data

(63) Continuation of application No. 16/787,942, filed on Feb. 11, 2020, now Pat. No. 11,090,390, which is a continuation of application No. 16/555,668, filed on Aug. 29, 2019, now abandoned, which is a continuation of application No. 15/886,495, filed on Feb. 1, 2018, now Pat. No. 10,435,432, which is a continuation of application No. 15/215,857, filed on Jul. 21, 2016, now Pat. No. 9,914,748, which is a continuation of application No. 14/313,868, filed on Jun. 24, 2014, now Pat. No. 9,428,543, which is a continuation of application No. 13/434,451, filed on Mar. 29, 2012, now Pat. No. 8,795,673.

(60) Provisional application No. 61/468,997, filed on Mar. 29, 2011.

(51) Int. Cl.
    A61K 39/00        (2006.01)
    A61K 47/68        (2017.01)
    C07K 1/113        (2006.01)
    C07K 16/28        (2006.01)
    C07K 16/32        (2006.01)

(52) U.S. Cl.
    CPC ...... *A61K 47/6803* (2017.08); *A61K 47/6809* (2017.08); *A61K 47/6819* (2017.08); *A61K 47/6849* (2017.08); *A61K 47/6867* (2017.08); *C07K 1/113* (2013.01); *C07K 16/2896* (2013.01); *C07K 16/32* (2013.01)

(58) Field of Classification Search
    CPC .............................................. A61K 47/6803
    See application file for complete search history.

(56) References Cited

U.S. PATENT DOCUMENTS

| | | |
|---|---|---|
| 4,137,230 A | 1/1979 | Hashimoto et al. |
| 4,149,003 A | 4/1979 | Carlsson et al. |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,664,911 A | 5/1987 | Uhr et al. |
| 4,780,210 A | 10/1988 | Hsia |
| 4,859,449 A | 8/1989 | Mattes |
| 4,859,499 A | 8/1989 | Sauvinet et al. |
| 5,024,834 A | 6/1991 | Houston et al. |
| 5,208,020 A | 5/1993 | Chari et al. |
| 5,225,539 A | 7/1993 | Winter |
| 5,241,078 A | 8/1993 | Moreland et al. |
| 5,252,714 A | 10/1993 | Harris et al. |
| 5,416,064 A | 5/1995 | Chari et al. |
| 5,475,092 A | 12/1995 | Chari et al. |

(Continued)

FOREIGN PATENT DOCUMENTS

| | | |
|---|---|---|
| EP | 0239400 A2 | 9/1987 |
| EP | 0425235 A2 | 5/1991 |

(Continued)

OTHER PUBLICATIONS

Extended European Search Report issued by the European Patent Office in corresponding Application No. EP 18196502 dated Apr. 4, 2019 (our reference IGH-00197).

(Continued)

*Primary Examiner* — Albert M Navarro

(74) *Attorney, Agent, or Firm* — Nixon & Vanderhye, PC

(57) ABSTRACT

The invention provides a one-step process for preparing a cell-binding agent cytotoxic agent conjugate comprising contacting a cell-binding agent with a cytotoxic agent to form a first mixture comprising the cell-binding agent and the cytotoxic agent and contacting the first mixture comprising the cell-binding agent and the cytotoxic agent with a bifunctional crosslinking reagent, which provides a linker, in a solution having a pH of about 4 to about 9 to provide a second mixture comprising the cell-binding agent cytotoxic agent conjugate, wherein the cell-binding agent is chemically coupled through the linker to the cytotoxic agent, free cytotoxic agent, and reaction by-products. The second mixture is then optionally subjected to purification to provide a purified cell-binding agent cytotoxic agent conjugate.

22 Claims, No Drawings

Specification includes a Sequence Listing.

(56) References Cited

U.S. PATENT DOCUMENTS

| | | |
|---|---|---|
| 5,529,986 A | 6/1996 | Larsson et al. |
| 5,545,806 A | 8/1996 | Lonberg et al. |
| 5,552,293 A | 9/1996 | Lindholm et al. |
| 5,556,623 A | 9/1996 | Barton et al. |
| 5,569,825 A | 10/1996 | Lonberg et al. |
| 5,580,853 A | 12/1996 | Sytkowski |
| 5,585,089 A | 12/1996 | Queen et al. |
| 5,585,499 A | 12/1996 | Chari et al. |
| 5,612,474 A | 3/1997 | Patel |
| 5,639,641 A | 6/1997 | Pedersen et al. |
| 5,665,357 A | 9/1997 | Rose et al. |
| 5,693,761 A | 12/1997 | Queen et al. |
| 5,693,762 A | 12/1997 | Queen et al. |
| 5,714,149 A | 2/1998 | Rhind et al. |
| 5,714,352 A | 2/1998 | Jakobovits |
| 5,747,446 A | 5/1998 | Sytkowski |
| 5,846,545 A | 12/1998 | Chari et al. |
| 5,885,793 A | 3/1999 | Griffiths et al. |
| 5,919,758 A | 7/1999 | Sytkowski |
| 5,965,714 A | 10/1999 | Ryall |
| 5,969,108 A | 10/1999 | McCafferty et al. |
| 6,171,586 B1 | 1/2001 | Lam et al. |
| 6,235,716 B1 | 5/2001 | Ben-Sasson |
| 6,265,150 B1 | 7/2001 | Terstappen et al. |
| 6,316,003 B1 | 11/2001 | Frankel et al. |
| 6,333,410 B1 | 12/2001 | Chari et al. |
| 6,340,461 B1 | 1/2002 | Terman |
| 6,340,701 B1 | 1/2002 | Chari et al. |
| 6,371,975 B2 | 4/2002 | Cruise et al. |
| 6,372,738 B2 | 4/2002 | Chari et al. |
| 6,391,913 B1 | 5/2002 | Page et al. |
| 6,436,931 B1 | 8/2002 | Chari et al. |
| 6,441,163 B1 | 8/2002 | Chari et al. |
| 6,462,070 B1 | 10/2002 | Hasan et al. |
| 6,534,660 B1 | 3/2003 | Yongxin et al. |
| 6,573,245 B1 | 6/2003 | Marciani |
| 6,586,618 B1 | 7/2003 | Zhao et al. |
| 6,596,757 B1 | 7/2003 | Chari et al. |
| 6,630,579 B2 | 10/2003 | Chari et al. |
| 6,632,979 B2 | 10/2003 | Erickson et al. |
| 6,706,708 B2 | 3/2004 | Chari et al. |
| 6,716,821 B2 | 4/2004 | Zhao et al. |
| 6,756,397 B2 | 6/2004 | Zhao et al. |
| 6,875,886 B2 | 4/2005 | Frangioni |
| 6,913,748 B2 | 7/2005 | Widdison |
| 7,045,605 B2 | 5/2006 | Bander et al. |
| 7,097,840 B2 | 8/2006 | Erickson et al. |
| 7,196,073 B2 | 3/2007 | Marciani |
| 7,368,565 B2 | 5/2008 | Chari et al. |
| 7,575,748 B1 | 8/2009 | Erickson et al. |
| 7,642,044 B2 | 1/2010 | Thogersen et al. |
| 7,811,572 B2 | 10/2010 | Dai et al. |
| 7,964,415 B2 | 6/2011 | Zhelev et al. |
| 8,088,387 B2 | 1/2012 | Steeves et al. |
| 8,206,901 B2 | 6/2012 | Freskgard et al. |
| 8,383,122 B2 | 2/2013 | Dai et al. |
| 8,557,966 B2 | 10/2013 | Ab et al. |
| 8,624,003 B2 | 1/2014 | Kellogg et al. |
| 8,795,673 B2 | 8/2014 | Li et al. |
| 8,840,877 B2 | 9/2014 | Adamson et al. |
| 8,933,205 B2 | 1/2015 | Dai et al. |
| 9,376,500 B2 | 6/2016 | Kellogg et al. |
| 9,428,543 B2 | 8/2016 | Li et al. |
| 9,771,432 B2 | 9/2017 | Kellogg et al. |
| 9,789,204 B2 | 10/2017 | Dai et al. |
| 9,914,748 B2 | 3/2018 | Li et al. |
| 10,435,432 B2 | 10/2019 | Li et al. |
| 2002/0001587 A1 | 1/2002 | Erickson et al. |
| 2002/0150585 A1 | 10/2002 | Marciani |
| 2002/0197266 A1 | 12/2002 | Debinski |
| 2003/0004210 A1 | 1/2003 | Chari et al. |
| 2003/0055226 A1 | 3/2003 | Chari et al. |
| 2003/0195365 A1 | 10/2003 | Zhao et al. |
| 2004/0024049 A1 | 2/2004 | Baloglu et al. |
| 2004/0192900 A1 | 9/2004 | Kunz et al. |
| 2004/0220142 A1 | 11/2004 | Marciani |
| 2004/0235840 A1 | 11/2004 | Chari et al. |
| 2004/0241174 A1 | 12/2004 | Amphlett et al. |
| 2005/0031627 A1 | 2/2005 | Mazzola et al. |
| 2005/0053608 A1 | 3/2005 | Weber et al. |
| 2005/0074425 A1 | 4/2005 | Waugh et al. |
| 2005/0112130 A1 | 5/2005 | Bhat et al. |
| 2005/0118183 A1 | 6/2005 | Hoffee et al. |
| 2005/0169933 A1 | 8/2005 | Steeves et al. |
| 2005/0175619 A1 | 8/2005 | Duffy et al. |
| 2005/0261232 A1 | 11/2005 | Strong et al. |
| 2006/0024317 A1 | 2/2006 | Boyd et al. |
| 2006/0062786 A1 | 3/2006 | Salcedo et al. |
| 2006/0073528 A1 | 4/2006 | Lecerf et al. |
| 2006/0099592 A1 | 5/2006 | Freskgard et al. |
| 2006/0100163 A1 | 5/2006 | Orlando et al. |
| 2006/0153834 A1 | 7/2006 | Carbonell et al. |
| 2006/0182740 A1 | 8/2006 | Yang et al. |
| 2006/0182750 A1 | 8/2006 | Chari et al. |
| 2006/0193865 A1 | 8/2006 | Govindan |
| 2006/0233811 A1 | 10/2006 | Chari |
| 2007/0031402 A1 | 2/2007 | Zhang et al. |
| 2007/0048314 A1 | 3/2007 | Dai et al. |
| 2007/0154901 A1 | 7/2007 | Thogersen et al. |
| 2007/0155750 A1 | 7/2007 | Neamati et al. |
| 2007/0196275 A1 | 8/2007 | Li et al. |
| 2007/0264257 A1 | 11/2007 | Dunussi-Joannopoulos et al. |
| 2008/0166363 A1 | 7/2008 | Govindan et al. |
| 2008/0171040 A1 | 7/2008 | Ebens et al. |
| 2008/0171865 A1 | 7/2008 | Steeves et al. |
| 2008/0213349 A1 | 9/2008 | Thakker et al. |
| 2008/0279868 A1 | 11/2008 | Boyd et al. |
| 2008/0305044 A1 | 12/2008 | McDonagh et al. |
| 2009/0274713 A1 | 11/2009 | Chari et al. |
| 2010/0003719 A1 | 1/2010 | Thagersen et al. |
| 2010/0047257 A1 | 2/2010 | Blanc et al. |
| 2010/0129314 A1 | 5/2010 | Singh et al. |
| 2010/0203007 A1 | 8/2010 | Li et al. |
| 2010/0291021 A1 | 11/2010 | Vetter et al. |
| 2010/0316656 A1 | 12/2010 | Bouchard et al. |
| 2011/0003969 A1 | 1/2011 | Kellogg et al. |
| 2011/0064754 A1 | 3/2011 | Taylor et al. |
| 2011/0166319 A1 | 7/2011 | Dai et al. |
| 2011/0206658 A1 | 8/2011 | Crowley et al. |
| 2011/0221744 A1 | 9/2011 | Bae et al. |
| 2011/0223257 A1 | 9/2011 | Zhao et al. |
| 2012/0149732 A1 | 6/2012 | Chucholowski et al. |
| 2012/0225089 A1 | 9/2012 | Bouchard et al. |
| 2012/0226026 A1 | 9/2012 | Singh et al. |
| 2012/0238731 A1 | 9/2012 | Fishkin et al. |
| 2012/0253021 A1 | 10/2012 | Li et al. |
| 2012/0259100 A1 | 10/2012 | Jin |
| 2012/0282175 A1 | 11/2012 | Carrigan et al. |
| 2013/0071482 A1 | 3/2013 | Bae et al. |
| 2013/0281678 A1 | 10/2013 | Dai et al. |
| 2014/0179906 A1 | 6/2014 | Kellogg et al. |
| 2014/0309406 A1 | 10/2014 | Li et al. |
| 2014/0350228 A1 | 11/2014 | Liu et al. |
| 2015/0010494 A1 | 1/2015 | Adamson et al. |
| 2015/0182635 A1 | 7/2015 | Dai et al. |
| 2015/0225446 A1 | 8/2015 | Chen et al. |
| 2015/0297742 A1 | 10/2015 | Strieker et al. |
| 2015/0306242 A1 | 10/2015 | Li et al. |
| 2015/0307596 A1 | 10/2015 | Li et al. |

FOREIGN PATENT DOCUMENTS

| | | |
|---|---|---|
| EP | 0457250 A2 | 11/1991 |
| EP | 0485749 A2 | 5/1992 |
| EP | 1258255 A1 | 11/2002 |
| EP | 2468304 A2 | 6/2012 |
| GB | 2188638 A | 10/1987 |
| JP | 2000026404 A | 1/2000 |
| WO | WO-92/01047 A1 | 1/1992 |
| WO | WO-96/39183 A1 | 12/1996 |
| WO | WO-99/06587 A2 | 2/1999 |
| WO | WO-1999/005317 A1 | 2/1999 |
| WO | WO-00/02587 A1 | 1/2000 |
| WO | WO-2000/066091 A1 | 11/2000 |

(56) References Cited

FOREIGN PATENT DOCUMENTS

| | | |
|---|---|---|
| WO | WO-01/24763 A2 | 4/2001 |
| WO | WO-02/16368 A1 | 2/2002 |
| WO | WO-02/16401 A2 | 2/2002 |
| WO | WO-02/060955 A2 | 8/2002 |
| WO | WO-02/092127 A1 | 11/2002 |
| WO | WO-02/094325 A2 | 11/2002 |
| WO | WO-02/098883 A1 | 12/2002 |
| WO | WO-2002/098887 A1 | 12/2002 |
| WO | WO-2002/098897 A2 | 12/2002 |
| WO | WO-03/053462 A2 | 7/2003 |
| WO | WO-2003/057163 A2 | 7/2003 |
| WO | WO-03/092623 A2 | 11/2003 |
| WO | WO-03/102132 A2 | 12/2003 |
| WO | WO-2004/103272 A2 | 12/2004 |
| WO | WO-2004/110498 A2 | 12/2004 |
| WO | WO-2005/037992 A2 | 4/2005 |
| WO | WO-2005/077090 A2 | 8/2005 |
| WO | WO-2005/094882 A1 | 10/2005 |
| WO | WO-2005/112919 A2 | 12/2005 |
| WO | WO-2005/117986 A2 | 12/2005 |
| WO | WO-2006/086733 A2 | 8/2006 |
| WO | WO-2006/113623 A2 | 10/2006 |
| WO | WO-2007/009229 A1 | 1/2007 |
| WO | WO-2007/024536 A2 | 3/2007 |
| WO | WO-2007/034495 A2 | 3/2007 |
| WO | WO-2008/057683 A2 | 5/2008 |
| WO | WO-2009/134952 A2 | 11/2009 |
| WO | WO-2011/039724 A1 | 4/2011 |
| WO | WO-2011/106528 A1 | 9/2011 |
| WO | WO-2012-112687 A1 | 8/2012 |
| WO | WO-2012/112708 A1 | 8/2012 |
| WO | WO-2012/135517 A2 | 10/2012 |
| WO | WO-2014/055893 A1 | 4/2014 |

OTHER PUBLICATIONS

Hamann et al., "An Anti-CD33 Antibody-Calicheamicin Conjugate for Treatment of Acute Myeloid Leukemia. Choice of Linker," Bioconj. Chem., 13(1):40-46 (2002).

Kinoshita et al., "Enzyme Immunoassay for Captopril," J. Pharm. Sci., 75(7):711-713 (1986).

Yin et al., "Phagemid Encoded Small Molecules for High Throughput Screening of Chemical Libraries," J. Am. Chem. Soc., 126(42):13570-13571 (2004).

Yin et al., "Supporting Information—Phagemid Encoded Small Molecules for High Throughput Screening of Chemical Libraries," J. Am. Chem. Soc., 126(42):S1-S8 (2004).

"Clinical Trials Begin of Antiangiogenesis Antibody, CNTO 95," Cancer Weekly, 57 (Jan. 13, 2004).

Al-Arif et al., "Synthesis of Fatty Acyl CoA and Other Thiol Esters Using N-Hydroxysuccinimide Esters of Fatty Acids," J Lipid Res, 10: 344-345 (1969).

Al-Katib et al., "Superior Antitumor Activity of SAR3419 to Rituximab in Xenograft Models for non-Hodgkin's Lymphoma," Clin Cancer Res, 15(12):4038-4045 (2009).

Baldus et al., "Lewis(y) Antigent (CD174) and Apopiosis in Gastric and Colorectal Carcinomas: Correlations with Clinical and Prognostic Parameters," Histol Histopathol, 21(5):503-510 (2006).

Berg et al., Biochemistry, 5th Ed., New York: WH Freeman, 1-8 (2002).

Bergelt et al., "Listeriolysin O as Cytotoxic Component of an Immunotoxin," Protein Sci, 18(6): 1210-1220 (2009).

Bhuyan et al., "CC=1-65 (NSC 298223), A Most Potent Antitumor Agent: Kinetics of Inhibition of Growth, DNA Synthesis, and Cell Survival," Cancer Res, 42(9): 3532-3537 (1982).

Boger et al., "Synthesis and Preliminary Evaluation of (+)-CBI-Indole2: An Enhanced Functional Analog of (+)-CC-1065," Bioorg Med Chem Lett, 1(2):115-120 (1991).

Boger et al., "Synthesis of N-(tert-buty!oxycarbonyi)-CBI, CBI, CBI-CDPI1, and CBI-CDPI2 Enhanced Functional Analogs of CC-1065 Incorporating the 1,2,9,9a-tetrahydrocyclopropa[c]benz[e]indol-4-one (CBI) Left-Hand Subunit," J Org Chem, 55(23): 5823-5833 (1990).

Boschetti et al., "Antibody Separation by Hydrophobic Charge Induction Chromatography," Trends Microbiol, 20(8): 333-337 (2002).

Brinkman et al., "A Recombinant Immunotoxin Containing a Disulfide-Stabilized Fv Fragment," Proc Natl Acad Sci USA, 90(16): 7538-7542 (1993).

Burgess, "The Complex Mediators of Ceil Growth and Differentiation," Immunol Today, 5(6): 155-158 (1984).

Carlsson et al., "Protein Thiolation and Reversible Protein-Protein Conjugation. N-Succinimidyl 3-(2-pyridyldithio) Propionate, a New Heterobifunctional Reagent," Biochem J. 173(3): 723-737 (1978).

Cassidy et al., "Purification of staphylococcal alpha-toxin by adsorption chromatography on glass," Infect Immun, 13(3): 982-986 (1976).

Chari et al., "Enhancement of the Selectivity and Antitumor Efficacy of a CC-1065 Analogue Through Immunoconjugates Formation," Cancer Res, 55(18): 4079-4084 (1995).

Chari et al., "Immunoconjugates Containing Novel Maytansinoids: Promising Anticancer Drugs," Cancer Res, 52(1): 127-131 (1992).

Chen et al., "Factors affecting endotoxin removal from recombinant therapeutic proteins by anion exchange chromatography," Protein Expr Purif, 64(1): 76-81 (2009).

Christy et al., "High-Performance Tangential Flow Filtration: A Highly Selective Membrane Separation Process," Desalination, 144(1-3): 133-136 (2002).

Colomer et al., "Herceptin: from the Bench to the Clinic," Cancer Invest, 19(1): 49-56 (2001).

Desmyter et al., "Crystal Structure of a camel Single-Domain VH Antibody Fragment in Complex with Lysozyme," Nat Struct Biol, 3(9): 803-811 (1996).

Erickson et al., "Antibody-Maytansinoid Conjugates Are Activated in Targeted Cancer Cells by Lysosomal Degradation and Linker-Dependent Intracellular Processing," Cancer Res. 66: 4426-4433 (2006).

European Search Report issued by the European Patent Office in corresponding Application No. 13844268.6, dated Apr. 3, 2017 (our ref. IGH-00480).

Extended European Search Report for European Application No. 10783998.7 dated May 28, 2015.

Extended European Search Report for European Application No. 12856692.4 dated Jul. 3, 2015.

Extended European Search Report issued by the European Patent Office in corresponding Application No. 13843881.7, dated Apr. 11, 2016.

Gao et al., "Expression of Lewis y Antigent and Integrin AlphaV, Beta3 in Ovarian Cancer and Their Relationship with chemotherapeutic Drug Resistance," J Exp Clin Cane Res, 32: 36 (2013).

Ghetie et al., "Large Scale Preparation of Immunotoxins Constructed with the Fab'fragment of IgG1 Murine Monoclonal Antibodies and Chemically Deglycosylated Ricin A Chain," J Immunol Methods, 112(2): 267-277 (1988).

Gong et al., "Comparison of DNA Immobilization Efficiency on New and Regenerated Commercial Amine-Reactive Polymer Microarray Surfaces," Surf Sci, 570: 67-77 (2004).

Greenberg et al., "A New Antigen Receptor Gene Family that Undergoes Rearrangement and Extensive Somatic Diversification in Sharks," Nature, 374 (6518): 168-173 (1995).

Griffin et al., "A Monoclonal Antibody Reactive with Normal and Leukemic Human Myeloid Progenitor Cells," Leukemia Res, 8(4): 521-534 (1984).

Haskard et al., "The Production of Human Monoclonal Autoantibodies from Patients with Rheumatoid Arthritis by the EBV-hybridoma Technique," J Immunol Methods, 74(2): 361-367 (1984).

Heider et al., "Splice Variants of the Cell Surface Glycoprotein CD44 Associated with Metastatic Tumour Cells Are Expressed in Normal Tissues of Humans and Cynomolgus Monkeys," Eur J Cancer, 31A(13-14): 2385-2391 (1995).

Henning, "Tumor Cell Targeted Gene Delivery by Adenovirus 5 Vectors Carrying Knobless Fibers with Antibody-binding Domains," Gene Ther, 12(3): 211-224 (2005).

(56) References Cited

OTHER PUBLICATIONS

Hurwitz et al., "The Covalent Binding of Daunomycin and Adriamycin to Antibodies, with Retention of Both Drug and Antibody Activities," Cancer Res, 35: 1175-1181 (1975).
Huse et al., "Generation of a Large Combinatorial Library of the Immunoglobulin Repertoire in Phage Lambda," Science, 246(4935): 1275-1281 (1989).
Instructions for SMCC and Sulfo-SMCC, Thermo Scientific, 1-4 (2007).
International Search Report and Written Opinion for International Application No. PCT/US10/37046, dated Jul. 30, 2010.
International Search Report and Written Opinion for International Application No. PCT/US12/031243, dated Dec. 10, 2012.
International Search Report and Written Opinion for International Application No. PCT/US12/31253, dated Dec. 7, 2012.
International Search Report and Written Opinion for International Application No. PCT/US2006/004937 dated Apr. 11, 2007.
International Search Report and Written Opinion for International Application No. PCT/US2006/031653 dated Apr. 3, 2007.
International Search Report and Written Opinion for International Application No. PCT/US2012/069527 dated Feb. 20, 2013.
International Search Report and Written Opinion for International Application No. PCT/US2013/63415, dated Jan. 29, 2014.
International Search Report and Written Opinion for International Application No. PCT/US2013/63480 dated Jan. 16, 2014.
International Search Report and Written Opinion for International Application No. PCT/US2013/63503 dated Jan. 16, 2014.
International Search Report for International Application No. PCT/US2002/03378 dated Jun. 12, 2002.
Jayson et al., "Phase I Study of CNTO 95, a Fully Human Monoclonal Antibody (mAb) to alphav Integrins, in Patients with Solid Tumors," J Clin Oncol, 22(14): 3119 (2004).
Jensen et al., "Targeting the Neural Cell Adhesion Molecule in Cancer," Cancer Lett, 258(1): 9-21 (2007).
Jiao et al., "Pharmacokinetics of CNTO 95, a Fully Human MAB to Human Integrin Receptors Following Single or Multiple IV Injections to Cynomolgus Monkeys," Eur J Cancer, 2(8): 93 (2004).
Kahn et al., "Purification of plasmid DNA by tangential flow filtration," Biotechnol Bioeng, 69(1): 101-106 (2000).
Kawai et al., "Chemical Modification of Ansamitocin. III. Synthesis and Biological Effects of 3-acyl Esters of Maytansinol," Chem Pharm Bull, 32(9): 3441-3451 (1984).
Kellogg et al., "Antibody-maytansinoid conjugates with hydrophilic linkers: cytotoxic therapeutics with enhanced potency against cancer cells with low antigen number and multidrug resistance," abstract 5480, 2009 AACR annual meeting (2009).
Kohler et al., "Derivation of Specific Antibody-Producing Tissue Culture and Tumor Lines by Cell Fusion," Eur J Immunol, 6: 511-519 (1976).
Kupchan et al., "Structural Requirements for Antileukemic Activity Among the Naturally Occurring and Semisynthetic Maytansinoids," J Med Chem, 21(1): 31-37 (1978).
Ladino et al., "Folate-Maytansinoids: Target-Selective Drugs of Low Molecular Weight," Int J Cancer, 73(6): 859-864 (1997).
Lewis et al., "An Improved Method for Conjugating Monoclonal Antibodies with N-hydroxysulfosuccinimidyl DOTA," Bioconjugate Chem, 12(2): 320-324 (2001).
Liu et al, "Cure of Human Small Cell Lung Cancer Xenografts in SCID Mice by a hN901-maytansinoid Immunoconjuqate," 1997 AACR Annual Meeting, Abstract 190 (1997).
Liu et al, "Cure of Human Small Cell Lung Cancer Xenografts in SCID Mice by a hN901-maytansinoid Immunoconjugate," Proc Natl Acad Sci USA, 93(16): 8618-8623 (1996).
Liu et al., "Monoclonal Antibodies to the Extracellular Domain of Prostate-Specific Membrane Antigen Also React with Tumor Vascular Endothelium," Cancer Res, 57(17): 3629-3634 (1997).
Lundberg et al., "Click Assisted One-Pot Multi-Step Reactions in Polymer Science: Accelerated Synthetic Protocols," Macromol Rapid Comm, 29: 998-1015 (2008).

Maloney et al., "IDEC-C2B8 (Rituximab) Anti-CD20 Monoclonal Antibody Therapy in Patients with Relapsed Low-grade non-Hodgkin's Lymphoma," Blood, 90(6): 2188-2195 (1997).
Manosroi et al., "Thermo-stability and Antitumor Activity on Colon Cancer Cell Lines of Monoclonal Anti-CEA Antibody-Saporin Immunotoxin," J Korean Med Sci, 7(2): 128-135 (1992).
McDonagh et al., "Engineered anti-CD70 antibody-drug conjugate with increased therapeutic index," Mol Cancer Ther, 7(9): 2913-2923 (2008).
Merriam Webster, Online Dictionary, "Room Temperature," [retrieved at URL htto://www.mernam-webster.com/medical/room%20temperature on Dec. 12, 2014].
Nadler et al., "B4, a Human B Lymphocyte-associated Antigen Expressed on Normal, Mitogen-activated, and Malignant B Lymphocytes," J Immunol, 131(1): 244-250 (1983).
Nisonoff et al., "Separation of Univalent Fragments from the Bivalent Rabbit Antibody Molecule by Reduction of Disulfide Bonds," Arch Biochem Biophys, 89: 230-244 (1960).
O'Keefe et al., "Characterization of a Transferrin-diphtheria Toxin Conjugate," J Biol Chem, 260(2): 932-937 (1985).
Okamoto et al., "Therapeutic Effect of Ansamitocin Targeted to Tumor by a Bispecific Monoclonal Antibody," Jpn J Cancer Res, 83(7): 761-768 (1992).
Parham, "On the Fragmentation of Monoclonal IgG1, IgG2b from BALB/c Mice," J Immunol, 131(6): 2895-2902 (1983).
Pastan et al., "Characterization of Monoclonal Antibodies B1 and B3 that React with Mucinous Adenocarcinomas," Cancer Res, 51(14): 3781-3787 (1991).
Pedersen et al., "Comparison of Surface Accessible residues in Human and Murine Immunoglobulin Fv Domains. Implication for humanization of Murine Antibodies," J Mol Biol, 235(3): 959-973 (1994).
Pietersz, "The Linkage of Cytotoxic Drugs to Monoclonal Antiboies for the Treatment of Cancer," Bioconjugate Chem, 1(2): 89-95 (1990).
Reider et al., "Maytansinoids," The Alkaloids, XXII, 71-73 (1984).
Reis et al., "High-performance tangential flow filtration using charged membranes," J Membrane Sci, 159(1-2): 133-142 (1999).
Reiter et al., "Engineering Interchain Disulfide Bonds into Conserved Framework Regions of Fv Fragments: Improved Biochemical Characteristics of Recombinant Immunotoxins Containing Disulfide-Stabilised Fv," Protein Engineering, 7(5): 697-704 (1994).
Ritz et al., "A Monoclonal Antibody to Human Acute Lymphoblastic Leukaemia Antigen," Nature, 283(5747): 583-585 (1980).
Roder et al., "The EBV-hybriodoma Technique," Methods Enzymol, 121: 140-167 (1986).
Roguska et al., "Humanization of Murine Monoclonal Antibodies Through Variable Domain Resurfacing," Proc Natl Acad Sci USA, 91(3): 969-973 (1974).
Sehgal et al., "A Method for the High Efficiency of Water-Soluble Carbodiimide-Mediated Amidation," Anal Biochem, 218: 87-91 (1994).
Smith, "Technology Evaluation: C242-DM1, ImmunoGen Inc.," Curr Opin Mol Ther, 3(2): 198-203 (2001).
Spring et al., "Allotypic Markers on Fab Fragments of Mouse Immunoglobulins." J Immunol, 113(2): 470-478 (1974).
Stanfield et al., "Crystal Structure of a Shark Single-Domain Antibody V Region in Complex with Lysozyme," Science, 305(5691): 1770-1773 (2004).
Stryer et al., "Levels of Structure in Protein Architecture," Biochemitry, 3rd Ed., New York: WH Freeman, 31-33 (1998).
Sytkowski et al., "Human Erythropoietin Dimers with Markedly Enhanced in Vivo Activity," Proc Natl Acad Sci USA, 95(3): 1184-1188 (1998).
Taylor-Papadimitriou et al., "Monoclonal Antibodies io Epithelium-Specific Components of the Human Milk Fat Globule Membrane: Production and Reaction with Cells in Culture," Int J Cancer, 28: 17-21 (1981).
Trikha et al., "CNTO 95, a Fully Human Monoclonal Antibody that Inhibits alphav Integrins, Has Antitumor and Antiangiogenic Activity in Vivo," Int J Cancer, 110(3): 326-335 (2004).
Trouet et al., "A Covalent Linkage Between Daunorubicin and Proteins that is Stable in Serum and Reversible by Lysosomal

(56) References Cited

OTHER PUBLICATIONS

Hydrolases, as Required for a Lysosomotrophic Drug-Carrier Conjugate: In vitro and in vivo Studies," Proc Natl Acad Sci USA, 79: 626-629 (1982).

Tugcu et al., "Maximizing productivity of chromatography steps for purification of monoclonal antibodies," Biotechnol Bioeng, 99(3): 599-613 (2008).

Ugwu et al., "The Effect of Buffers on Protein Conformational Stability," Pharmaceutical Technology, 86, 88, 90, 92, 94, 96, 98, 100, 102, 104, 106, 108, 110-113 (2004).

Umemoto et al., "Preparation and in Vitro Cytotoxicity of a Methotrexate-anti-MM46 Monoclonal Antibody Conjugate via an Oligopepetide Spacer," Int J Cancer, 43(4): 677-684 (1989).

Van Hof et al., "Biodistribution of (111)indium-labeled Engineered Human Antibody CTMO1 in Ovarian Cancer Patients: Influence of Protein Dose," Cancer Res, 56(22): 5179-5185 (1996).

Wang et al., "Trichosanthin-monoclonal Antibody Conjugate Specifically Cytotoxic to Human Hepatoma Cells in Vitro," Cancer Res, 51: 3353-3355 (1991).

Warpehoski et al., "Stereoelectronic Factors Influencing the Biological Activity and DNA Interaction of Synthetic Antitumor Agents Modeled on CC-1065," J Med Chem, 31(3): 590-603 (1988).

Wawryznczak et al., Molecular and Bioiogical Properties of an Arbin A Chain Immunotoxin Designated for Therapy of Human Small Cell Lung Cancer, Br J Cancer, 66(2): 361-366 (1992).

Welt et al., Antibody Targeting in Metastic Colon Cancer: A Phase I Study of J Clin Oncol, 12(6): 1193-1203 (1994).

Winkler et al., "Changing the Antigen Binding Specificity by Single Point Mutations of an Anti-p24 (HIV-1) Antibody," J Immunol, 165(8): 4505-4514 (2000).

Written Opinion and International Search Report dated Jul. 30, 2010, as issued in International Patent Application No. PCT/US10/37046, filed Jun. 2, 2010.

Yan et al., "Enhancement of the Adhesive and Spreading Potentials of Ovarian Carcinomas RMG-1 Cells Due to Increased Expression of Integrin Alpha5beta1 with the Lewis Y-structure on Transfection of the Alpha1,2-fucosyltransferase Gene," Biochimie, 92(7): 852-857 (2010).

Zhou et al., "New Q membrane scale-down model for process-scale antibody purification," J Chromatogr A, 1134(1-2): 66-73 (2006).

PREPARATION OF MAYTANSINOID ANTIBODY CONJUGATES BY A ONE-STEP PROCESS

CROSS-REFERENCE TO RELATED APPLICATIONS

This patent application is a Continuation of U.S. patent application Ser. No. 16/787,942, filed on Feb. 11, 2020, which is a Continuation of U.S. patent application Ser. No. 16/555,668, filed on Aug. 29, 2019, now abandoned, which is a Continuation of U.S. patent application Ser. No. 15/886,495, filed on Feb. 1, 2018, now U.S. Pat. No. 10,435,432, issued Oct. 8, 2019, which is a Continuation of U.S. patent application Ser. No. 15/215,857, filed Jul. 21, 2016, now U.S. Pat. No. 9,914,748, issued Mar. 13, 2018, which is a Continuation of U.S. patent application Ser. No. 14/313,868, filed Jun. 24, 2014, now U.S. Pat. No. 9,428,543, issued Aug. 30, 2016, which is a Continuation of U.S. patent application Ser. No. 13/434,451, filed Mar. 29, 2012, now U.S. Pat. No. 8,795,673, issued Aug. 5, 2014, which claims the benefit of priority of U.S. Provisional Patent Application No. 61/468,997, filed Mar. 29, 2011, the contents of each of which are incorporated herein by reference in their entirety.

INCORPORATION-BY-REFERENCE OF MATERIAL SUBMITTED ELECTRONICALLY

Incorporated by reference in its entirety herein is a computer-readable nucleotide/amino acid sequence listing identified as follows: One 158,830 Byte ASCII (Text) file named "6776.0696_Sequence_Listing.txt," created on Jul. 7, 2021.

BACKGROUND OF THE INVENTION

Antibody-Drug-Conjugates (ADC's) which are useful for the treatment of cancer and other diseases are commonly composed of three distinct elements: a cell-binding agent; a linker; and a cytotoxic agent. The conventional method of conjugating a cell-binding agent, such as an antibody, to a cytotoxic agent, employs two distinct reaction steps with the antibody. In the first reaction step (the modification step), the antibody is reacted with a heterobifunctional linker to produce a linker-modified antibody. The modified antibody product is then optionally purified from the excess linker or hydrolyzed linker reagent. In the second reaction step (the conjugation step), the linker-modified antibody is reacted with the cytotoxic agent containing a reactive group, such as thiol, to generate the antibody-cytotoxic agent conjugate, which is again purified in an additional purification step.

The processes that have been previously described for manufacture of the antibody-cytotoxic agent conjugates are complex because they are encumbered with steps that are cumbersome to perform or produce immunoconjugates that are less pure or less stable than optimally desired. Thus, it would be desirable to modify or eliminate one or more manufacturing steps while improving the product quality, such as purity and/or stability.

In view of the foregoing, there is a need in the art to develop improved processes for preparing cell-binding agent-cytotoxic agent conjugates that are of substantially high purity and can be prepared avoiding cumbersome steps and by reducing time and cost to the user. The invention provides such a process. These and other advantages of the invention, as well as additional inventive features, will be apparent from the description of the invention provided herein.

BRIEF SUMMARY OF THE INVENTION

The invention provides a process for preparing a cell-binding agent cytotoxic agent conjugate comprising the step of contacting a cell-binding agent with a cytotoxic agent to form a first mixture comprising the cell-binding agent and the cytotoxic agent, and then contacting the first mixture comprising the cell-binding agent and the cytotoxic agent with a bifunctional crosslinking reagent comprising a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products. The process can further comprise the step of purifying the mixture to provide a purified cell-binding agent cytotoxic agent conjugate.

The processes of the present invention provide cell-binding agent cytotoxic agent conjugate with high purity and/or stability. To achieve the high purity and/or stability of the conjugate, it is essential that the cytotoxic agent is contacted with the cell-binding agent first to form a mixture comprising the cell-binding agent and the cytotoxic agent before the mixture is contacted with a bifunctional crosslinking reagent.

The present invention also includes a cell-binding agent cytotoxic agent conjugate prepared according to the processes described herein.

DETAILED DESCRIPTION OF THE INVENTION

The invention provides a one-step process for preparing a cell-binding agent cytotoxic agent conjugate. The process comprises contacting a cell-binding agent (e.g., an antibody) with a cytotoxic agent to form a first mixture comprising the cell-binding agent and the cytotoxic agent, and then contacting the first mixture comprising the cell-binding agent and the cytotoxic agent with a bifunctional crosslinking reagent comprising a linker, in a solution having a pH of about 4 to about 9 to provide a second mixture comprising the cell-binding agent cytotoxic agent conjugate, free cytotoxic agent, and reaction by-products, wherein the cell-binding agent is chemically coupled through the linker to the cytotoxic agent. The second mixture is then subjected to purification to provide a purified cell-binding agent cytotoxic agent conjugate.

In one embodiment, the contacting is effected by providing the cell-binding agent, then contacting the cell-binding agent with the cytotoxic agent to form a first mixture comprising the cell-binding agent and the cytotoxic agent, and then contacting the first mixture comprising the cell-binding agent and the cytotoxic agent with the bifunctional crosslinking reagent. For example, in one embodiment, the cell-binding agent is provided in a reaction vessel, the cytotoxic agent is added to the reaction vessel (thereby contacting the cell-binding agent), and then the bifunctional crosslinking reagent is added to the mixture comprising the cell-binding agent and the cytotoxic agent (thereby contacting the mixture comprising the cell-binding agent and the cytotoxic agent). In one embodiment, the cell-binding agent is provided in a reaction vessel, and the cytotoxic agent is added to the reaction vessel immediately following providing the cell-binding agent to the vessel. In another embodiment, the cell-binding agent is provided in a reaction vessel, and the cytotoxic agent is added to the reaction vessel after a time interval following providing the cell-binding agent to the vessel (e.g., about 5 minutes, about 10 minutes, about 20 minutes, about 30 minutes, about 40 minutes, about 50 minutes, about 1 hour, about 1 day or longer after providing the cell-binding agent to the space). The cytotoxic agent can be added quickly (i.e., within a short time interval, such as about 5 minutes, about 10 minutes) or slowly (such as by using a pump).

The mixture comprising the cell-binding agent and the cytotoxic agent can be then contacted with the bifunctional crosslinking reagent either immediately after contacting the cell-binding agent with the cytotoxic agent or at some later point (e.g., about 5 minutes to about 8 hours or longer) after contacting the cell-binding agent with the cytotoxic agent. For example, in one embodiment, the bifunctional crosslinking reagent is added to the mixture comprising the cell-binding agent and the cytotoxic agent immediately after the addition of the cytotoxic agent to the reaction vessel comprising the cell-binding agent. Alternatively, the mixture comprising the cell-binding agent and the cytotoxic agent can be contacted with the bifunctional crosslinking reagent at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the cell-binding agent with the cytotoxic agent.

In another embodiment, the cytotoxic agent and the bifunctional agent are added through multiple cycles (e.g., 1, 2, 3, 4, 5 or more cycles). For example, the invention provides a process comprising the steps of: a) contacting a cell-binding agent with a cytotoxic agent to form a first mixture comprising the cell-binding agent and the cytotoxic agent; and then contacting the first mixture with a bifunctional crosslinking reagent comprising a linker, in a solution having a pH of about 4 to about 9 to provide a second mixture comprising the cell-binding agent cytotoxic agent conjugate, free cytotoxic agent, and reaction by-products, wherein the cell-binding agent is chemically coupled through the linker to the cytotoxic agent; b) contacting the second mixture with the cytotoxic agent to form a third mixture; and then contacting the third mixture with the bifunctional crosslinking reagent at a pH of about 4 to about 9 to provide a fourth mixture; and c) purifying the fourth mixture to provide the purified cell-binding agent cytotoxic agent conjugate. In one embodiment, step b) is carried out after a time interval (e.g., about 1 hour, about 2 hours, about 3 hours or longer) following step a). In another embodiment, step b) can be repeated several times (e.g., 1, 2, 3, 4 or more times) before step c) is carried out. The additional step b) can be carried out after a time interval (e.g., about 1 hour, about 2 hours, about 3 hours or longer) following the initial step b).

In another embodiment, the bifunctional crosslinking reagent is added before the complete addition of the cytotoxic agent. For example, in one embodiment, the cytotoxic agent is added to the cell-binding agent continuously over a time interval (e.g., over about 5 minutes, about 10 minutes, about 30 minutes, about 1 hour, about 2 hours, about 3 hours, or longer) to form a mixture comprising the cell-binding agent and the cytotoxic agent. Before the addition of the cytotoxic agent is complete, the bifunctional crosslinking reagent is added to the mixture comprising the cell-binding agent and the cytotoxic agent, provided that at any time, the cytotoxic agent is in molar excess of the bifunctional crosslinking reagent. In one embodiment, the bifunctional crosslinking reagent is added continuously over a time interval (e.g., over about 5 minutes, about 10 minutes, about 30 minutes, about 1 hour, about 2 hours, about 3 hours, or longer).

After the mixture comprising the cell-binding agent and the cytotoxic agent is contacted with the bifunctional crosslinking reagent, the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

Contacting the cell-binding agent with the cytotoxic agent and then the bifunctional crosslinking reagent (i.e., the reaction step) occurs in a solution having a pH of about 4 to about 9 (e.g., about 4, about 4.5, about 5, about 5.5, about 6, about 6.5, about 7, about 7.5, about 8, about 8.5, or about 9). In one embodiment, the reaction step occurs in a solution having a pH of about 6 or less (e.g., about 4 to about 6, about 4 to about 5.5, or about 4.5 to about 5.5).

In another embodiment, the inventive process comprises contacting a cell-binding agent with a cytotoxic agent and then a bifunctional crosslinking reagent in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the inventive process comprises contacting a cell-binding agent with a cytotoxic agent and a bifunctional crosslinking reagent in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In a specific embodiment, the inventive process comprises contacting a cell-binding agent with a cytotoxic agent and a bifunctional crosslinking reagent in a solution having a pH of about 7.8 (e.g., a pH of 7.6 to 8.0 or a pH of 7.7 to 7.9).

The inventive process comprises performing the one-step reaction (i.e., contacting a cell-binding agent with a cytotoxic agent and then a bifunctional crosslinking reagent) at any suitable temperature known in the art. For example, the one-step reaction can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, contacting a cell-binding agent with a cytotoxic agent and a bifunctional crosslinking reagent occurs at a temperature of about 16° C. to about 24° C. (e.g., about 16° C., about 17° C., about 18° C., about 19° C., about 20° C., about 21° C., about 22° C., about 23° C., about 24° C., or about 25° C.).

In another embodiment, contacting a cell-binding agent with a cytotoxic agent and then a bifunctional crosslinking reagent occurs at a temperature of about 15° C. or less (e.g., about −10° C. to about 15° C., or about 0° C. to about 15° C.). In this respect, the inventive process comprises contacting a cell-binding agent with a cytotoxic agent and then a bifunctional crosslinking reagent at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the bifunctional crosslinking reagent. In one embodiment, the inventive process comprises contacting a cell-binding agent with a cytotoxic agent and then a bifunctional crosslinking reagent at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another embodiment, the inventive process comprises contacting a cell-binding agent with a cytotoxic agent and then a bifunctional crosslinking reagent at a temperature of about 10° C. (e.g., a temperature of 8° C. to 12° C. or a temperature of 9° C. to 11° C.).

In one embodiment, the inventive process comprises contacting a cell-binding agent with a cytotoxic agent and then a bifunctional crosslinking reagent in a solution having a high pH (e.g., about 7 or greater) at a low temperature (e.g., about 15° C. or less). For example, in one embodiment, the inventive process comprises contacting a cell-binding agent with a cytotoxic agent and then a bifunctional crosslinking reagent in a solution having a pH of about 7.5 at a temperature of about 15° C., in a solution having a pH of about 7.8 at a temperature of about 10° C., in a solution having a pH about 8.2 at a temperature of about 0° C., or in a solution having a pH about 8.5 at a temperature of about 0° C. In another embodiment, the inventive process comprises contacting a cell-binding agent with a cytotoxic agent and then a bifunctional crosslinking reagent in a solution having a pH of 7.0 to 8.5 (e.g., a pH of 7.5 to 8.0) at a temperature of 5° C. to 15° C.

In one embodiment, the inventive process further comprises a quenching step to quench any unreacted cytotoxic agent and/or unreacted bifunctional crosslinking reagent. The quenching step is performed prior to purification of the cell-binding agent cytotoxic agent. For example, the inventive process comprises (a) contacting a cell-binding agent with a cytotoxic agent to form a mixture comprising the cell-binding agent and the cytotoxic agent and then contacting the mixture comprising the cell-binding agent and the cytotoxic agent with a bifunctional crosslinking reagent comprising a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products, (b) quenching the mixture prepared in step (a) to quench any unreacted cytotoxic agent and/or unreacted bifunctional crosslinking reagent, and (c) purifying the mixture to provide a purified cell-binding agent cytotoxic agent conjugate.

In one embodiment, the mixture is quenched by contacting the mixture with a quenching reagent. As used herein, the "quenching reagent" refers to a reagent that reacts with the free cytotoxic agent and/or the bifunctional crosslinking reagent.

In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the cytotoxic agent is quenched. The quenching step can help prevent the dimerization of the cytotoxic agent, particular the cytotoxic agent having an unreacted thiol group (such as DM1). The dimerized cytotoxic agent can be difficult to remove. The quenching step may also minimize any unwanted thiol-disulfide interchange reaction with the native antibody disulfide groups. Upon quenching with polar, charged thiol-quenching reagents (such as 4-maleimidobutyric acid or 3-maleimidopropionic acid), the excess, unreacted cytotoxic agent is converted into a polar, charged, water-soluble adduct that can be easily separated from the covalently-linked conjugate during the purification step. Quenching with non-polar and neutral thiol-quenching reagents can also be used.

In one embodiment, the mixture is quenched by contacting the mixture with a quenching reagent that reacts with the unreacted bifunctional crosslinking reagent. For example, nucleophiles can be added to the mixture in order to quench any unreacted bifunctional crosslinking reagent. The nucleophile preferably is an amino group containing nucleophile, such as lysine, taurine and hydroxylamine.

In a preferred embodiment, the reaction (i.e., contacting a cell-binding agent with a cytotoxic agent and then a bifunctional crosslinking reagent) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the cell-binding agent and the cytotoxic agent is contacted with the bifunctional crosslinking reagent.

The inventive process may optionally include the addition of sucrose to the reaction step (i.e., contacting a cell-binding agent with a cytotoxic agent and a bifunctional crosslinking reagent) to increase solubility and recovery of the cell-binding agent-cytotoxic agent conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

Following the reaction step, the cell-binding agent cytotoxic agent conjugate is subjected to a purification step. In this regard, the cell-binding agent cytotoxic agent conjugate can be purified from the other components of the mixture (e.g., free cytotoxic agent and reaction by-products) using tangential flow filtration (TFF), which is a membrane-based tangential flow filtration process, non-adsorptive chromatography, adsorptive chromatography, adsorptive filtration, selective precipitation, or any other suitable purification process, as well as combinations thereof. In one embodiment of the invention, the cell-binding agent cytotoxic agent conjugate is purified using a single purification step (e.g., TFF). Preferably, the conjugate is purified and exchanged into the appropriate formulation using a single purification step (e.g., TFF). In another embodiment of the invention, the cell-binding agent cytotoxic agent conjugate is purified using two sequential purification steps. For example, the conjugate can be first purified by selective precipitation, adsorptive filtration, adsorptive chromatography or non-absorptive chromatography, followed by purification with TFF. One of ordinary skill in the art will appreciate that purification of the cell-binding agent cytotoxic agent conjugate enables the isolation of a stable conjugate comprising the cell-binding agent chemically coupled to the cytotoxic agent.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., Mab-Select, GE Healthcare, Piscataway, N.J.), where the cell-binding agent is an antibody, and lectin affinity resins, e.g. Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In one embodiment, the inventive process further comprises a holding step to release the unstably bound linkers from the cell-binding agent. The holding step comprises holding the mixture prior to purification of the cell-binding agent-cytotoxic agent conjugate (e.g., after the reaction step, between the reaction step and the quenching step, or after the quenching step). For example, the inventive process comprises (a) contacting a cell-binding agent with a cytotoxic agent to form a mixture comprising the cell-binding agent and the cytotoxic agent; and then contacting the mixture comprising the cell-binding agent and the cytotoxic agent with a bifunctional crosslinking reagent, which provides a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products, (b) holding the mixture prepared in step (a) to release the unstably bound linkers from the cell-binding agent, and (c) purifying the mixture to provide a purified cell-binding agent cytotoxic agent conjugate.

In another embodiment, the inventive process comprises (a) contacting a cell-binding agent with a cytotoxic agent to form a mixture comprising the cell-binding agent and the cytotoxic agent; and then contacting the mixture comprising the cell-binding agent and the cytotoxic agent with a bifunctional crosslinking reagent, which provides a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products, (b) quenching the mixture prepared in step (a) to quench any unreacted cytotoxic agent and/or unreacted bifunctional crosslinking reagent, (c) holding the mixture prepared in step (b) to release the unstably bound linkers from the cell-binding agent, and (d) purifying the mixture to provide a purified cell-binding agent cytotoxic agent conjugate.

Alternatively, the holding step can be performed after purification of the cell-binding agent-cytotoxic agent conjugate, followed by an additional purification step.

In a preferred embodiment, the reaction (i.e., contacting a cell-binding agent with a cytotoxic agent and then a bifunctional crosslinking reagent) is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the cell-binding agent and the cytotoxic agent is contacted with the bifunctional crosslinking reagent.

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the cell-binding agent while not substantially releasing the stably bound linkers from the cell-binding agent. In one embodiment, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another embodiment, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another embodiment, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to a week. In another embodiment, the holding step comprises maintaining the solution at a temperature of about 2° C. to about 8° C. overnight (e.g., about 12 to about 24 hours, preferably about 20 hours).

The pH value for the holding step preferably is about 4 to about 10. In one embodiment, the pH value for the holding step is about 4 or more, but less than about 6 (e.g., 4 to 5.9) or about 5 or more, but less than about 6 (e.g., 5 to 5.9). In another embodiment, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In specific embodiments, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The invention provides a process for preparing compositions of stable conjugates comprising a cell-binding agent chemically coupled to a cytotoxic agent, wherein the compositions are substantially free of unstable conjugates. In this respect, the invention provides a process for preparing cell-binding agent-cytotoxic agent conjugate of substantially high purity and stability. Such compositions can be used for treating diseases because of the high purity and stability of the conjugates. Compositions comprising a cell-binding agent, such as an antibody, chemically coupled to a cytotoxic agent, such as a maytansinoid, are described in, for example, U.S. Pat. No. 7,374,762, the entire teaching of which is incorporated herein by reference in its entirety. In one aspect of the invention, a cell-binding agent-cytotoxic agent conjugate of substantially high purity has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free cytotoxic agent level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (e) no substantial increase in the level of free cytotoxic agent upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free cytotoxic agent means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free cytotoxic agent is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the cell-binding agent that is covalently linked with the bifunctional crosslinking reagent, wherein the cell-binding agent is not covalently coupled to the cytotoxic agent through the linker of the bifunctional crosslinking reagent (i.e., the "unconjugated linker" can be represented by CBA-L, wherein CBA represents the cell-binding agent and L represents the bifunctional crosslinking reagent. In contrast, the cell-binding agent cytotoxic agent conjugate can be represented by CBA-L-D, wherein D represents the cytotoxic agent).

In one embodiment, the average molar ratio of the cytotoxic agent to the cell-binding agent in the cell-binding agent cytotoxic agent conjugate is about 1 to about 10, about 2 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

The present invention provides a more efficient process for preparing compositions of stable conjugates comprising a cell-binding agent chemically coupled to a cytotoxic agent. In one embodiment, as compared to the traditional processes for preparing conjugates of a cell-binding agent and a cytotoxic agent, less amount of the cytotoxic agent is required to achieve the same average molar ratio of the cytotoxic agent to the cell-binding agent for the conjugates.

The cell-binding agent can be any suitable agent that binds to a cell, typically and preferably an animal cell (e.g., a human cell). The cell-binding agent preferably is a peptide or a polypeptide. Suitable cell-binding agents include, for example, antibodies (e.g., monoclonal antibodies and fragments thereof), interferons (e.g. alpha., beta., gamma.), lymphokines (e.g., IL-2, IL-3, IL-4, IL-6), hormones (e.g., insulin, TRH (thyrotropin releasing hormone), MSH (melanocyte-stimulating hormone), steroid hormones, such as androgens and estrogens), growth factors and colony-stimulating factors such as EGF, TGF-alpha, FGF, VEGF, G-CSF, M-CSF and GM-CSF (Burgess, *Immunology Today* 5:155-158 (1984)), nutrient-transport molecules (e.g., transferrin), vitamins (e.g., folate) and any other agent or molecule that specifically binds a target molecule on the surface of a cell.

Where the cell-binding agent is an antibody, it binds to an antigen that is a polypeptide or a glycotope and may be a transmembrane molecule (e.g., receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I); insulin-like growth factor binding proteins; EpCAM; GD3; FLT3; PSMA; PSCA; MUC1; MUC16; STEAP; CEA; TENB2; EphA receptors; EphB receptors; folate receptor; FOLR1; mesothelin; crypto; alpha beta$_6$; integrins; VEGF, VEGFR; EGFR; transferrin receptor; IRTA1; IRTA2; IRTA3; IRTA4; IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in U.S. Patent Application Publication No. 2008/0171040 or U.S. Patent Application Publication No. 2008/0305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3, or HER4 receptor; endoglin; c-Met; IGF1R; prostate antigens such as PCA3, PSA, PSGR, NGEP, PSMA, PSCA, TMEFF2, and STEAPI; LGR5; B7H4; and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents The term "antibody," as used herein, refers to any immunoglobulin, any immunoglobulin fragment, such as Fab, Fab', F(ab')$_2$, dsFv, sFv, minibodies, diabodies, tribodies, tetrabodies (Parham, *J. Immunol.*, 131: 2895-2902 (1983); Spring et al. *J. Immunol.*, 113: 470-478 (1974); Nisonoff et al. *Arch. Biochem. Biophys.*, 89: 230-244 (1960), Kim et al., *Mol. Cancer Ther.*, 7: 2486-2497 (2008), Carter, *Nature Revs.*, 6: 343-357 (2006)), or immunoglobulin chimera, which can bind to an antigen on the surface of a cell (e.g., which contains a complementarity determining region (CDR)). Any suitable antibody can be used as the cell-binding agent. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody molecules, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, *Eur. J. Immunol.*, 5: 511-519 (1976), Harlow and Lane (eds.), *Antibodies: A Laboratory Manual, CSH Press* (1988), and C. A. Janeway et al. (eds.), Immunobiology, 5$^{th}$ Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, *J. Immunol. Methods,* 74(2): 361-67 (1984), and Roder et al., *Methods Enzymol.,* 121: 140-67 (1986)), bacteriophage vector expression systems (see, e.g., Huse et al., *Science,* 246: 1275-81 (1989)), or phage display libraries comprising antibody fragments, such as Fab and scFv (single chain variable region) (see, e.g., U.S. Pat. Nos. 5,885,793 and 5,969,108, and International Patent Application Publications WO 92/01047 and WO 99/06587).

The monoclonal antibody can be isolated from or produced in any suitable animal, but is preferably produced in a mammal, more preferably a mouse or human, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-cytotoxic agent conjugate. To circumvent these complications, a monoclonal antibody preferably is not recognized as "foreign" by the human immune system.

To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual,* 3$^{rd}$ Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example, U.S. Pat. Nos. 5,545,806 and 5,569,825, and Janeway et al., supra.

Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.*, 235: 959-973 (1994). While the antibody employed in the conjugate of the inventive composition most preferably is a humanized monoclonal antibody, a human monoclonal antibody and a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab')$_2$ fragment. Reduction of a F(ab')$_2$ fragment with dithiothreitol or mercaptoethylamine produces a fragment referred to as a Fab' fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7: 697-704 (1994)). Antibody fragments in the context of the invention, however, are not limited to these exemplary types of antibody fragments. Any suitable antibody fragment that recognizes and binds to a desired cell surface receptor or antigen can be employed. Antibody fragments are further described in, for example, Parham, *J. Immunol.*, 131: 2895-2902 (1983), Spring et al., *J. Immunol.*, 113: 470-478 (1974), and Nisonoff et al., *Arch. Biochem. Biophys.*, 89: 230-244 (1960). Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

In addition, the antibody can be a chimeric antibody or an antigen binding fragment thereof. By "chimeric" it is meant that the antibody comprises at least two immunoglobulins, or fragments thereof, obtained or derived from at least two different species (e.g., two different immunoglobulins, such as a human immunoglobulin constant region combined with a murine immunoglobulin variable region). The antibody also can be a domain antibody (dAb) or an antigen binding fragment thereof, such as, for example, a camelid antibody (see, e.g., Desmyter et al., *Nature Struct. Biol.*, 3: 752, (1996)), or a shark antibody, such as, for example, a new antigen receptor (IgNAR) (see, e.g., Greenberg et al., *Nature*, 374: 168 (1995), and Stanfield et al., *Science*, 305: 1770-1773 (2004)).

Any suitable antibody can be used in the context of the invention. For example, the monoclonal antibody J5 is a murine IgG2a antibody that is specific for Common Acute Lymphoblastic Leukemia Antigen (CALLA) (Ritz et al., *Nature*, 283: 583-585 (1980)), and can be used to target cells that express CALLA (e.g., acute lymphoblastic leukemia cells). The monoclonal antibody MY9 is a murine IgG1 antibody that binds specifically to the CD33 antigen (Griffin et al., *Leukemia Res.*, 8: 521 (1984)), and can be used to target cells that express CD33 (e.g., acute myelogenous leukemia (AML) cells).

Similarly, the monoclonal antibody anti-B4 (also referred to as B4) is a murine IgG1 antibody that binds to the CD19 antigen on B cells (Nadler et al., *J. Immunol.*, 131: 244-250 (1983)), and can be used to target B cells or diseased cells that express CD19 (e.g., non-Hodgkin's lymphoma cells and chronic lymphoblastic leukemia cells). N901 is a murine monoclonal antibody that binds to the CD56 (neural cell adhesion molecule) antigen found on cells of neuroendocrine origin, including small cell lung tumor, which can be used in the conjugate to target drugs to cells of neuroendocrine origin. The J5, MY9, and B4 antibodies preferably are resurfaced or humanized prior to their use as part of the conjugate. Resurfacing or humanization of antibodies is described in, for example, Roguska et al., *Proc. Natl. Acad. Sci. USA*, 91: 969-73 (1994).

In addition, the monoclonal antibody C242 binds to the CanAg antigen (see, e.g., U.S. Pat. No. 5,552,293), and can be used to target the conjugate to CanAg expressing tumors, such as colorectal, pancreatic, non-small cell lung, and gastric cancers. HuC242 is a humanized form of the monoclonal antibody C242 (see, e.g., U.S. Pat. No. 5,552,293). The hybridoma from which HuC242 is produced is deposited with ECACC identification Number 90012601. HuC242 can be prepared using CDR-grafting methodology (see, e.g., U.S. Pat. Nos. 5,585,089, 5,693,761, and 5,693,762) or resurfacing technology (see, e.g., U.S. Pat. No. 5,639,641). HuC242 can be used to target the conjugate to tumor cells expressing the CanAg antigen, such as, for example, colorectal, pancreatic, non-small cell lung, and gastric cancer cells.

To target ovarian cancer and prostate cancer cells, an anti-MUC1 antibody can be used as the cell-binding agent in the conjugate. Anti-MUC1 antibodies include, for example, anti-HMFG-2 (see, e.g., Taylor-Papadimitriou et al., *Int. J. Cancer*, 28: 17-21 (1981)), hCTM01 (see, e.g., van Hof et al., *Cancer Res.*, 56: 5179-5185 (1996)), and DS6. Prostate cancer cells also can be targeted with the conjugate by using an anti-prostate-specific membrane antigen (PSMA) as the cell-binding agent, such as J591 (see, e.g., Liu et al., *Cancer Res.*, 57: 3629-3634 (1997)). Moreover, cancer cells that express the Her2 antigen, such as breast, prostate, and ovarian cancers, can be targeted with the conjugate by using anti-Her2 antibodies, e.g., trastuzumab, as the cell-binding agent. Cells that express epidermal growth factor receptor (EGFR) and variants thereof, such as the type III deletion mutant, EGFRvIII, can be targeted with the conjugate by using anti-EGFR antibodies. Anti-EGFR antibodies are described in International Patent Application Nos. PCT/US11/058385 and PCT/US11/058378. Anti-EGFRvIII antibodies are described in U.S. Pat. Nos. 7,736,644 and 7,628,986 and U.S. Application Publications 2010/0111979, 2009/0240038, 2009/0175887, 2009/0156790, and 2009/0155282. Anti-IGF-IR antibodies that bind to insulin-like growth factor receptor, such as those described in U.S. Pat. No. 7,982,024, also can be used in the conjugate. Antibodies that bind to CD27L, Cripto, CD138, CD38, EphA2, integrins, CD37, folate, CD20, PSGR, NGEP, PSCA, TMEFF2, STEAPI, endoglin, and Her3 also can be used in the conjugate.

In one embodiment, the antibody is selected from the group consisting of huN901, huMy9-6, huB4, huC242, an anti-HER2 antibody (e.g., trastuzumab), bivatuzumab, sibrotuzumab, rituximab, huDS6, anti-mesothelin antibodies described in International Patent Application Publication WO 2010/124797 (such as MF-T), anti-cripto antibodies described in U.S. Patent Application Publication 2010/0093980 (such as huB3F6), anti-CD138 antibodies described in U.S. Patent Application Publication 2007/0183971 (such as huB-B4), anti-EGFR antibodies described in International Patent Application Nos. PCT/US11/058385 and PCT/US11/058378 (such as EGFR-7), anti-EGFRvIII antibodies described U.S. Pat. Nos. 7,736,644 and 7,628,986 and U.S. Patent Application Publications 2010/0111979, 2009/0240038, 2009/0175887, 2009/0156790 and 2009/0155282, humanized EphA2 antibodies described in International Patent Application Publications WO 2011/039721 and WO 2011/039724 (such as 2H11R35R74); anti-CD38 antibodies described in International Patent Application Publication WO 2008/047242 (such as hu38SB19), anti-folate antibodies described in International Patent Application Publication WO 2011/106528, and U.S. Patent Application Publication 2012/0009181 (e.g., huMov19); anti-IGF1R antibodies described in U.S. Pat. Nos. 5,958,872, 6,596,743, and 7,982,024; anti-CD37 antibodies described in U.S. Patent Application Publication 2011/0256153 (e.g., huCD37-3); anti-integrin $\alpha_v\beta_6$ antibodies described in U.S. Application Publication 2006/0127407 (e.g., CNTO95); and anti-Her3 antibodies described in International Patent Application Publication WO 2012/019024.

In one embodiment, the CD37-binding agents include CD37-binding agents that comprise the heavy and light chain CDR sequences of CD37-3, CD37-12, CD37-38, CD37-50, CD37-51, CD37-56 or CD37-57. The heavy and light chain CDRs of CD37-38, CD37-50, CD37-51, CD37-56 and CD37-57 contain related sequences. Therefore, the CD-37 binding antibodies can also comprise heavy and light chain CDR sequences that comprise a consensus sequence obtained by the alignment of CD37-38, CD37-50, CD37-51, CD37-56 and CD37-57. The CDR sequences of CD37-3, CD37-12, CD37-38, CD37-50, CD37-51, CD37-56 and CD37-57, as well as the consensus sequence of CD37-38, CD37-50, CD37-51, CD37-56 and CD37-57 are described in Tables 1 and 2 below.

TABLE 1

Variable heavy chain CDR amino acid sequences

| Antibody | VH-CDR1 | VH-CDR2 | VH-CDR3 |
| --- | --- | --- | --- |
| CD37-3 | TSGVS (SEQ ID NO: 121) | VIWGDGSTN (SEQ ID NO: 122) | GGYSLAH (SEQ ID NO: 123) |
| CD37-12 | KYGMN (SEQ ID NO: 124) | WINTNTGESR (SEQ ID NO: 125) | GTVVAD (SEQ ID NO: 126) |
| CD37-38 | SGFGWH (SEQ ID NO: 127) | YILYSGGTD (SEQ ID NO: 128) | GYYGYGAWFVY (SEQ ID NO: 12) |
| CD37-50 | SGFAWH (SEQ ID NO: 13) | YILYSGSTV (SEQ ID NO: 14) | GYYGYGAWFAY (SEQ ID NO: 15) |
| CD37-51 | SGFAWH (SEQ ID NO: 16) | YIHYSGSTN (SEQ ID NO: 17) | GYYGFGAWFVY (SEQ ID NO: 18) |
| CD37-56 | SGFAWH (SEQ ID NO: 19) | YIHYSGGTN (SEQ ID NO: 20) | GYYGFGAWFAY (SEQ ID NO: 21) |
| CD37-57 | SGFAWH (SEQ ID NO: 22) | YILYSGSTV (SEQ ID NO: 23) | GYYGYGAWFAY (SEQ ID NO: 24) |
| CONSENSUS | SGF[A or G]WH (SEQ ID NO: 25) | YI[L or H]YSG[G or S]T[D, V, or N] (SEQ ID NO: 26) | GYYG[Y or F]GAWF[V or A]Y (SEQ ID NO: 27) |

TABLE 2

Variable light chain CDR amino acid sequences

| Antibody | VL-CDR1 | VL-CDR2 | VL-CDR3 |
| --- | --- | --- | --- |
| CD37-3 | RASENIRSNLA (SEQ ID NO: 28) | VATNLAD (SEQ ID NO: 29) | QHYWGTTWT (SEQ ID NO: 30) |
| CD37-12 | RASQSVSTSSYSYLY (SEQ ID NO: 31) | YASNLAS (SEQ ID NO: 32) | QHSWEIPYT (SEQ ID NO: 33) |
| CD37-38 | SASSSVTYMH (SEQ ID NO: 34) | DTSKLAS (SEQ ID NO: 35) | QQWISNPPT (SEQ ID NO: 36) |
| CD37-50 | SATSSVTYMH (SEQ ID NO: 37) | DTSKLPY (SEQ ID NO: 38) Humanized DTSNLPY (SEQ ID NO: 40) | QQWSDNPPT (SEQ ID NO: 39) |
| CD37-51 | SATSSVTYMH (SEQ ID NO: 41) | DTSKLAS (SEQ ID NO: 42) | QQWSSNPPT (SEQ ID NO: 43) |
| CD37-56 | SASSSVTYMH (SEQ ID NO: 44) | DTSKLAS (SEQ ID NO: 45) Humanized DTSNLAS (SEQ ID NO: 47) | QQWISDPPT (SEQ ID NO: 46) |
| CD37-57 | SATSSVTYMH (SEQ ID NO: 48) | DTSKLAS (SEQ ID NO: 49) Humanized DTSNLAS (SEQ ID NO: 51) | QQWSDNPPT (SEQ ID NO: 50) |

TABLE 2-continued

Variable light chain CDR amino acid sequences

| Antibody | VL-CDR1 | VL-CDR2 | VL-CDR3 |
|---|---|---|---|
| CONSENSUS | SA[T or S]SSVTYMH (SEQ ID NO: 52) | DTS[K or N]L[A or P][S or Y] (SEQ ID NO: 53) | QQW[I or S][S or D][N or D]PPT (SEQ ID NO: 54) |

The CD37 binding molecules can be antibodies or antigen binding fragments that specifically bind to CD37 that comprise the CDRs of CD37-3, CD37-12, CD37-50, CD37-51, CD37-56, or CD37-57 with up to four (i.e. 0, 1, 2, 3, or 4) conservative amino acid substitutions per CDR.

Polypeptides can comprise one of the individual variable light chains or variable heavy chains described herein.

Antibodies and polypeptides can also comprise both a variable light chain and a variable heavy chain. The variable light chain and variable heavy chain sequences of murine, chimeric, and humanized CD37-3, CD37-12, CD37-50, CD37-51, CD37-56, and CD37-57 antibodies are provided in Tables 3 and 4 below.

TABLE 3

Variable heavy chain amino acid sequences

| Antibody | VH Amino Acid Sequence (SEQ ID NO) |
|---|---|
| muCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 55) |
| chCD37-3 | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 56) |
| huCD37-3v1.0 | QVQVQESGPGLVAPSQTLSITCTVSGFSLTTSGVSWVRQPPGKGLEWLGVIW GDGSTNYHPSLKSRLSIKKDHSKSQVFLKLNSLTAADTATYYCAKGGYSLA HWGQGTLVTVSS (SEQ ID NO: 57) |
| huCD37-3v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSS (SEQ ID NO: 58) |
| muCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSS (SEQ ID NO: 59) |
| chCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSS (SEQ ID NO: 60) |
| muCD37-38 | DVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSA (SEQ ID NO: 61) |
| chCD37-38 | QVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSA (SEQ ID NO: 62) |
| huCD37-38 | QVQLQESGPGLVKPSQSLSLTCTVSGYSITSGFGWHWIRQFPGKGLEWMAYI LYSGGTDYNPSLKSRISITRDTSKNQFFLRLSSVTAADTATYYCARGYYGYG AWFVYWGQGTLVTVSS (SEQ ID NO: 63) |
| muCD37-50 | DVQLQESGPDLLKPSQSLSLTCTVTGYSITSGFAWHWIRQFPGNKLEWMGYI LYSGSTVYSPSLKSRISITRDTSKNHFFLQLNSVTTEDTATYYCARGYYGYG AWFAY (SEQ ID NO: 64) |
| huCD37-50 | QVQLQESGPGLLKPSQSLSLTCTVSGYSITSGFAWHWIRQHPGNKLEWMGY ILYSGSTVYSPSLKSRISITRDTSKNHFFLQLNSVTAADTATYYCARGYYGYG AWFAYWGQGTLVTVSA (SEQ ID NO: 65) |
| muCD37-51 | DVQLQESGPDLLKPSQSLSLTCTVTGYSISSGFAWHWIRQFPGNKLEWMGYI HYSGSTNYSPSLKSRISITRDSSKNQFFLQLNSVTTEDTATYYCARGYYGFGA WFVYWGQGTLVTVSA (SEQ ID NO: 66) |
| huCD37-51 | EVQLVESGPEVLKPGESLSLTCTVSGYSISSGFAWHWIRQFPGKGLEWMGYI HYSGSTNYSPSLQGRISITRDSSINQFFLQLNSVTASDTATYYCARGYYGFGA WFVYWGQGTLVTVSA (SEQ ID NO: 67) |

TABLE 3-continued

Variable heavy chain amino acid sequences

| Antibody | VH Amino Acid Sequence (SEQ ID NO) |
|---|---|
| muCD37-56 | DVQLQESGPDLVKPSQSLSLTCTVTGYSITSGFAWHWIRQFPGNKLEWMGY IHYSGGTNYNPSLKSRVSITRDTSKNQFFLQLNSVTTEDTATYYCARGYYGF GAWFAYWGQGTLVPVSA (SEQ ID NO: 68) |
| huCD37-56 | QVQLQESGPGLVKPSQSLSLTCTVSGYSITSGFAWHWIRQFPGKGLEWMGYI HYSGGTNYNPSLKSRVSITRDTSKNQFFLQLNSVTAADTATYYCARGYYGF GAWFAYWGQGTLVPVSA (SEQ ID NO: 69) |
| muCD37-57 | DVQLQESGPDLLKPSQSLSLTCTVTGYSITSGFAWHWIRQFPGNKLEWMGYI LYSGSTVYSPSLKSRISITRDTSKNQFFLQLNSVTTEDTATYYCARGYYGYG AWFAYWGQGTLVTVSA (SEQ ID NO: 70) |
| huCD37-57 | QVQLQESGPGLLKPSQSLSLTCTVSGYSITSGFAWHWIRQFPGKGLEWMGYI LYSGSTVYSPSLKSRISITRDTSKNQFFLQLNSVTAADTATYYCARGYYGYG AWFAYWGQGTLVTVSA (SEQ ID NO: 71) |

TABLE 4

Variable light chain amino acid sequences

| Antibody | VL Amino Acid Sequence (SEQ ID NO) |
|---|---|
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 72) |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKR (SEQ ID NO: 73) |
| huCD37-3 (1.0 and 1.1) | QVQVKESGPGLVAPSQSLSITCTVSGFSLTTSGVSWVRQPPGKGLEWLGVIW GDGSTNYHSALKSRLSIKKDHSKSQVFLKLNSLQTDDTATYYCAKGGYSLA HWGQGTLVTVSA (SEQ ID NO: 74) |
| muCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKR (SEQ ID NO: 75) |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKR (SEQ ID NO: 76) |
| muCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKR (SEQ ID NO: 77) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKR (SEQ ID NO: 78) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKR (SEQ ID NO: 79) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKR (SEQ ID NO: 80) |
| huCD37-50 | EIVLTQSPATMSASPGERVTMTCSATSSVTYMHWYQQKPGQSPKRWIYDTS NLPYGVPARFSGSGSGTSYSLTISSMEAEDAATYYCQQWSDNPPTFGQGTKL EIKR (SEQ ID NO: 81) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKR (SEQ ID NO: 82) |
| huCD37-51 | EIVLTQSPATMSASPGERVTMTCSATSSVTYMHWYQQKPGQSPKRWIYDTS KLASGVPARFSGSGSGTSYSLTISSMEAEDAATYYCQQWSSNPPTFGQGTKL EIKR (SEQ ID NO: 83) |

TABLE 4-continued

Variable light chain amino acid sequences

| Antibody | VL Amino Acid Sequence (SEQ ID NO) |
|---|---|
| muCD37-56 | QIVLTQSPAFMSASPGDKVTMTCSASSSVTYMHWYQQKSGTSPKRWIYDTS<br>KLASGVPARFSGGGSGTSYSLTISTMEAEDAATYYCQQWISDPPTFGGGTKL<br>EIKR (SEQ ID NO: 84) |
| huCD37-56 | DIVLTQSPAFMSASPGEKVTMTCSASSSVTYMHWYQQKPDQSPKRWIYDTS<br>NLASGVPSRFSGGGSGTDYSLTISSMEAEDAATYYCQQWISDPPTFGQGTKL<br>EIKR (SEQ ID NO: 85) |
| muCD37-57 | QIVLTQSPAIMSASPGEKVTMTCSATSSVTYMHWYQQKSGTSPKRWIYDTS<br>KLASGVPARFSGSGSGTSYSLTISSMEAEDAATYYCQQWSDNPPTFGSGTKL<br>EIKR (SEQ ID NO: 86) |
| huCD37-57 | EIVLTQSPATMSASPGERVTMTCSATSSVTYMHWYQQKPGQSPRRWIYDTS<br>NLASGVPARFSGSGSGTSYSLTISSMEAEDAATYYCQQWSDNPPTFGQGTKL<br>EIKR (SEQ ID NO: 87) |

Also provided are polypeptides that comprise: (a) a polypeptide having at least about 90% sequence identity to SEQ ID NOs:55-71; and/or (b) a polypeptide having at least about 90% sequence identity to SEQ ID NOs:72-87. In certain embodiments, the polypeptide comprises a polypeptide having at least about 95%, at least about 96%, at least about 97%, at least about 98%, or at least about 99% sequence identity to SEQ ID NOs:55-87. Thus, in certain embodiments, the polypeptide comprises (a) a polypeptide having at least about 95% sequence identity to SEQ ID NOs:55-71, and/or (b) a polypeptide having at least about 95% sequence identity to SEQ ID NOs:72-87. In certain embodiments, the polypeptide comprises (a) a polypeptide having the amino acid sequence of SEQ ID NOs:55-71; and/or (b) a polypeptide having the amino acid sequence of SEQ ID NOs:72-87.

In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:55-87 differs from SEQ ID NOs:55-87 by conservative amino acid substitutions only.

Polypeptides can comprise one of the individual light chains or heavy chains described herein. Antibodies and polypeptides can also comprise both a light chain and a heavy chain. The light chain and variable chain sequences of murine, chimeric, and humanized CD37-3, CD37-12, CD37-50, CD37-51, CD37-56, and CD37-57 antibodies are provided in Tables 5 and 6 below.

TABLE 5

Full-length heavy chain amino acid sequences

| Antibody | Full-Length Heavy Chain Amino Acid Sequence (SEQ ID NO) |
|---|---|
| muCD37-3 | QVQVKESGPGLVAPSQSLSITCTVSGFSLTTSGVSWVRQPPGKGLEWLGVIW<br>GDGSTNYHSALKSRLSIKKDHSKSQVFLKLNSLQTDDTATYYCAKGGYSLA<br>HWGQGTLVTVSAAKTTAPSVYPLAPVCGDTTGSSVTLGCLVKGYFPEPVTL<br>TWNSGSLSSGVHTFPAVLQSDLYTLSSSVTVTSSTWPSQSITCNVAHPASSTK<br>VDKKIEPRGPTIKPCPPCKCPAPNLLGGPSVFIFPPKIKDVLMISLSPIVTCVVV<br>DVSEDDPDVQISWFVNNVEVHTAQTQTHREDYNSTLRVVSALPIQHQDWM<br>SGKEFKCKVNNKDLPAPIERTISKPKGSVRAPQVYVLPPPEEEMTKKQVTLT<br>CMVTDFMPEDIYVEWTNNGKTELNYKNTEPVLDSDGSYFMYSKLRVEKKN<br>WVERNSYSCSVVHEGLHNHHTTKSFSRTPGK (SEQ ID NO: 88) |
| chCD37-3 | QVQVKESGPGLVAPSQSLSITCTVSGFSLTTSGVSWVRQPPGKGLEWLGVIW<br>GDGSTNYHSALKSRLSIKKDHSKSQVFLKLNSLQTDDTATYYCAKGGYSLA<br>HWGQGTLVTVSAASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDK<br>SRWQQGNVFSCSVMHEALHNHYTQKSLSLSPGK (SEQ ID NO: 89) |
| huCD37-3v1.0 | QVQVQESGPGLVAPSQTLSITCTVSGFSLTTSGVSWVRQPPGKGLEWLGVIW<br>GDGSTNYHPSLKSRLSIKKDHSKSQVFLKLNSLTAADTATYYCAKGGYSLA<br>HWGQGTLVTVSSASTKGPSVFPLAPSSKSTSGGTAALGCLVKDYFPEPVTVS<br>WNSGALTSGVHTFPAVLQSSGLYSLSSVVTVPSSSLGTQTYICNVNHKPSNT<br>KVDKKVEPKSCDKTHTCPPCPAPELLGGPSVFLFPPKPKDTLMISRTPEVTCV<br>VVDVSHEDPEVKFNWYVDGVEVHNAKTKPREEQYNSTYRVVSVLTVLHQ<br>DWLNGKEYKCKVSNKALPAPIEKTISKAKGQPREPQVYTLPPSRDELTKNQ<br>VSLTCLVKGFYPSDIAVEWESNGQPENNYKTTPPVLDSDGSFFLYSKLTVDK<br>SRWQQGNVFSCSVMHEALHNHYTQKSLSLSPG (SEQ ID NO: 90) |

TABLE 5-continued

Full-length heavy chain amino acid sequences

| Antibody | Full-Length Heavy Chain Amino Acid Sequence (SEQ ID NO) |
|---|---|
| huCD37-3v1.1 | QVQVQESGPGLVAPSQTLSITCTVSGFSLTTSGVSWVRQPPGKGLEWLGVIW GDGSTNYHSSLKSRLSIKKDHSKSQVFLKLNSLTAADTATYYCAKGGYSLA HWGQGTLVTVSSASTKGPSVFPLAPSSKSTSGGTAALGCLVKDYFPEPVTVS WNSGALTSGVHTFPAVLQSSGLYSLSSVVTVPSSSLGTQTYICNVNHKPSNT KVDKKVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQ DWLNGKEYKCKVSNKALPAPIEKTISKAKGQPREPQVYTLPPSRDELTKNQ VSLTCLVKGFYPSDIAVEWESNGQPENNYKTTPPVLDSDGSFFLYSKLTVDK SRWQQGNVFSCSVMHEALHNHYTQKSLSLSPG (SEQ ID NO: 91) |
| muCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSSAKTTAPSVYPLAPVCGDTTGSSVTLGCLVKGYFPEPV TLTWNSGSLSSGVHTFPAVLQSDLYTLSSSVTVTSSTWPSQSITCNVAHPASS TKVDKKIEPRGPTIKPCPPCKCPAPNLLGGPSVFIFPPKIKDVLMISLSPIVTCV VVDVSEDDPDVQISWFVNNVEVHTAQTQTHREDYNSTLRVVSALPIQHQD WMSGKEFKCKVNNKDLPAPIERTISKPKGSVRAPQVYVLPPPEEEMTKKQV TLTCMVTDFMPEDIYVEWTNNGKTELNYKNTEPVLDSDGSYFMYSKLRVE KKNWVERNSYSCSVVHEGLHNHHTTKSFSRTPGK (SEQ ID NO: 92) |
| chCD37-12 | QIQLVQSGPELKKPGETVKISCKASGYTFTKYGMNWVKQAQGKGLKWMG WINTNTGESRNAEEFKGRFAFSLETSASTAYLQINNLKYEDTATYFCGRGTV VADWGQGTTLTVSSASTKGPSVFPLAPSSKSTSGGTAALGCLVKDYFPEPVT VSWNSGALTSGVHTFPAVLQSSGLYSLSSVVTVPSSSLGTQTYICNVNHKPS NTKVDKKVEPKSCDKTHTCPPCPAPELLGGPSVFLFPPKPKDTLMISRTPEVT CVVVDVSHEDPEVKFNVVYVDGVEVHNAKTKPREEQYNSTYRVVSVLTVL HQDWLNGKEYKCKVSNKALPAPIEKTISKAKGQPREPQVYTLPPSRDELTK NQVSLTCLVKGFYPSDIAVEWESNGQPENNYKTTPPVLDSDGSFFLYSKLTV DKSRWQQGNVFSCSVMHEALHNHYTQKSLSLSPGK (SEQ ID NO: 93) |
| muCD37-38 | DVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSAAKTTPPSVYPLAPGSAAQTNSMVTLGCLVKGYFP EPVTVTWNSGSLSSGVHTFPAVLESDLYTLSSSVTVPSSMRPSETVTCNVAH PASSTKVDKKIVPRDCGCKPCICTVPEVSSVFIFPPKPKDVLTITLTPKVTCVV VDISKDDPEVQFSWFVDDVEVHTAQTQPREEQFNSTFRSVSELPIMHQDWL NGKEFKCRVNSAAFPAPIEKTISKTKGRPKAPQVYTIPPPKEQMAKDKVSLT CMITDFFPEDITVEWQWNGQPAENYKNTQPIMNTNGSYFVYSKLNVQKSN WEAGNTFTCSVLHEGLHNHHTEKSLSHSPGK (SEQ ID NO: 94) |
| chCD37-38 | QVQLQESGPDLVKPSQSLSLTCTVTGYSITSGFGWHWIRQFPGNKLEWMAY ILYSGGTDYNPSLKSRISITRDTSKNQFFLRLSSVTTEDTATYYCARGYYGYG AWFVYWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLT VDKSRWQQGNVFSCSVMHEALHNHYTQKSLSLSPG (SEQ ID NO: 95) |
| huCD37-38 | QVQLQESGPGLVKPSQSLSLTCTVSGYSITSGFGWHWIRQFPGKGLEWMAYI LYSGGTDYNPSLKSRISITRDTSKNQFFLRLSSVTAADTATYYCARGYYGYG AWFVYWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTP EVTCVVVDVSHEDPEVKFNWYVDGVEVHNAKTKPREEQYNSTYRVVSVLT VLHQDWLNGKEYKCKVSNKALPAPIEKTISKAKGQPREPQVYTLPPSRDELT KNQVSLTCLVKGFYPSDIAVEWESNGQPENNYKTTPPVLDSDGSFFLYSKLT VDKSRWQQGNVFSCSVMHEALHNHYTQKSLSLSPG (SEQ ID NO: 96) |
| muCD37-50 | DVQLQESGPDLLKPSQSLSLTCTVTGYSITSGFAWHWIRQFPGNKLEWMGYI LYSGSTVYSPSLKSRISITRDTSKNHFFLQLNSVTTEDTATYYCARGYYGYG AWFAYWGQGTLVTVSAAKTTAPSVYPLAPVCGDTTGSSVTLGCLVKGYFP EPVTLTWNSGSLSSGVHTFPAVLQSDLYTLSSSVTVTSSTWPSQSITCNVAHP ASSTKVDKKIEPRGPTIKPCPPCKCPAPNLLGGPSVFIFPPKIKDVLMISLSPIV TCVVVDVSEDDPDVQISWFVNNVEVHTAQTQTHREDYNSTLRVVSALPIQH QDWMSGKEFKCKVNNKDLPAPIERTISKPKGSVRAPQVYVLPPPEEEMTKK QVTLTCMVTDFMPEDIYVEWTNNGKTELNYKNTEPVLDSDGSYFMYSKLR VEKKNWVERNSYSCSVVHEGLHNHHTTKSFSRTPGK (SEQ ID NO: 97) |
| huCD37-50 | QVQLQESGPGLLKPSQSLSLTCTVSGYSITSGFAWHWIRQHPGNKLEWMGY ILYSGSTVYSPSLKSRISITRDTSKNHFFLQLNSVTAADTATYYCARGYYGYG AWFAYWGQGTLVTVSSASTKGPSVFPLAPSSKSTSGGTAALGCLVKDYFPE PVTVSWNSGALTSGVHTFPAVLQSSGLYSLSSVVTVPSSSLGTQTYICNVNH KPSNTKVDKKVEPKSCDKTHTCPPCPAPELLGGPSVFLFPPKPKDTLMISRTP |

TABLE 5-continued

Full-length heavy chain amino acid sequences

| Antibody | Full-Length Heavy Chain Amino Acid Sequence (SEQ ID NO) |
|---|---|
| | EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 98) |
| muCD37-51 | DVQLQESGPDLLKPSQSLSLTCTVTGYSISSGFAWHWIRQFPGNKLEWMGYI<br>HYSGSTNYSPSLKSRISITRDSSKNQFFLQLNSVTTEDTATYYCARGYYGFGA<br>WFVYWGQGTLVTVSAAKTTAPSVYPLAPVCGDTTGSSVTLGCLVKGYFPEP<br>VTLTWNSGSLSSGVHTFPAVLQSDLYTLSSSVTVTSSTWPSQSITCNVAHPAS<br>STKVDKKIEPRGPTIKPCPPCKCPAPNLLGGPSVFIFPPKIKDVLMISLSPIVTC<br>VVVDVSEDDPDVQISWFVNNVEVHTAQTQTHREDYNSTLRVVSALPIQHQD<br>WMSGKEFKCKVNNKDLPAPIERTISKPKGSVRAPQVYVLPPPEEEMTKKQV<br>TLTCMVTDFMPEDIYVEWTNNGKTELNYKNTEPVLDSDGSYFMYSKLRVE<br>KKNWVERNSYSCSVVHEGLHNHHTTKSFSRTPGK (SEQ ID NO: 99) |
| huCD37-51 | EVQLVESGPEVLKPGESLSLTCTVSGYSISSGFAWHWIRQFPGKGLEWMGYI<br>HYSGSTNYSPSLQGRISITRDSSINQFFLQLNSVTASDTATYYCARGYYGFGA<br>WFVYWGQGTLVTVSAASTKGPSVFPLAPSSKSTSGGTAALGCLVKDYFPEP<br>VTVSWNSGALTSGVHTFPAVLQSSGLYSLSSVVTVPSSSLGTQTYICNVNHK<br>PSNTKVDKKVEPKSCDKTHTCPPCPAPELLGGPSVFLFPPKPKDTLMISRTPE<br>VTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 100) |
| muCD37-56 | DVQLQESGPDLVKPSQSLSLTCTVTGYSITSGFAWHWIRQFPGNKLEWMGY<br>IHYSGGTNYNPSLKSRVSITRDTSKNQFFLQLNSVTTEDTATYYCARGYYGF<br>GAWFAYWGQGTLVPVSAAKTTPPSVYPLAPGSAAQTNSMVTLGCLVKGYF<br>PEPVTVTWNSGSLSSGVHTFPAVLESDLYTLSSSVTVPSSMRPSETVTCNVA<br>HPASSTKVDKKIVPRDCGCKPCICTVPEVSSVFIFPPKPKDVLTITLTPKVTCV<br>VVDISKDDPEVQFSWFVDDVEVHTAQTQPREEQFNSTFRSVSELPIMHQDW<br>LNGKEFKCRVNSAAFPAPIEKTISKTKGRPKAPQVYTIPPPKEQMAKDKVSL<br>TCMITDFFPEDITVEWQWNGQPAENYKNTQPIMNTNGSYFVYSKLNVQKSN<br>WEAGNTFTCSVLHEGLHNHHTEKSLSHSPGK (SEQ ID NO: 101) |
| huCD37-56 | QVQLQESGPGLVKPSQSLSLTCTVSGYSITSGFAWHWIRQFPGKGLEWMGYI<br>HYSGGTNYNPSLKSRVSITRDTSKNQFFLQLNSVTAADTATYYCARGYYGF<br>GAWFAYWGQGTLVPVSAASTKGPSVFPLAPSSKSTSGGTAALGCLVKDYFP<br>EPVTVSWNSGALTSGVHTFPAVLQSSGLYSLSSVVTVPSSSLGTQTYICNVN<br>HKPSNTKVDKKVEPKSCDKTHTCPPCPAPELLGGPSVFLFPPKPKDTLMISRT<br>PEVTCVVVDVSHEDPEVKFNWYVDGVEVHNAKTKPREEQYNSTYRVVSVL<br>TVLHQDWLNGKEYKCKVSNKALPAPIEKTISKAKGQPREPQVYTLPPSRDEL<br>TKNQVSLTCLVKGFYPSDIAVEWESNGQPENNYKTTPPVLDSDGSFFLYSKL<br>TVDKSRWQQGNVFSCSVMHEALHNHYTQKSLSLSPG (SEQ ID NO: 102) |
| muCD37-57 | DVQLQESGPDLLKPSQSLSLTCTVTGYSITSGFAWHWIRQFPGNKLEWMGYI<br>LYSGSTVYSPSLKSRISITRDTSKNQFFLQLNSVTTEDTATYYCARGYYGYG<br>AWFAYWGQGTLVTVSAAKTTAPSVYPLAPVCGDTTGSSVTLGCLVKGYFP<br>EPVTLTWNSGSLSSGVHTFPAVLQSDLYTLSSSVTVTSSTWPSQSITCNVAHP<br>ASSTKVDKKIEPRGPTIKPCPPCKCPAPNLLGGPSVFIFPPKIKDVLMISLSPIV<br>TCVVVDVSEDDPDVQISWFVNNVEVHTAQTQTHREDYNSTLRVVSALPIQH<br>QDWMSGKEFKCKVNNKDLPAPIERTISKPKGSVRAPQVYVLPPPEEEMTKK<br>QVTLTCMVTDFMPEDIYVEWTNNGKTELNYKNTEPVLDSDGSYFMYSKLR<br>VEKKNWVERNSYSCSVVHEGLHNHHTTKSFSRTPGK (SEQ ID NO: 103) |
| huCD37-57 | QVQLQESGPGLLKPSQSLSLTCTVSGYSITSGFAWHWIRQFPGKGLEWMGYI<br>LYSGSTVYSPSLKSRISITRDTSKNQFFLQLNSVTAADTATYYCARGYYGYG<br>AWFAYWGQGTLVTVSAASTKGPSVFPLAPSSKSTSGGTAALGCLVKDYFPE<br>PVTVSWNSGALTSGVHTFPAVLQSSGLYSLSSVVTVPSSSLGTQTYICNVNH<br>KPSNTKVDKKVEPKSCDKTHTCPPCPAPELLGGPSVFLFPPKPKDTLMISRTP<br>EVTCVVVDVSHEDPEVKFNWYVDGVEVHNAKTKPREEQYNSTYRVVSVLT<br>VLHQDWLNGKEYKCKVSNKALPAPIEKTISKAKGQPREPQVYTLPPSRDELT<br>KNQVSLTCLVKGFYPSDIAVEWESNGQPENNYKTTPPVLDSDGSFFLYSKLT<br>VDKSRWQQGNVFSCSVMHEALHNHYTQKSLSLSPG (SEQ ID NO: 104) |

TABLE 6

Full-length light chain amino acid sequences

| Antibody | Full-length Light Chain Amino Acid Sequence (SEQ ID NO) |
|---|---|
| muCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRADAAPTVSIFPPSSEQLTSGGASVVCFLNNFYPKDINVKWKIDGSERQ NGVLNSWTDQDSKDSTYSMSSTLTLTKDEYERHNSYTCEATHKTSTSPIVKS FNRNEC (SEQ ID NO: 105) |
| chCD37-3 | DIQMTQSPASLSVSVGETVTITCRASENIRSNLAWYQQKQGKSPQLLVNVAT NLADGVPSRFSGSGSGTQYSLKINSLQSEDFGTYYCQHYWGTTWTFGGGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 106) |
| huCD37-3 (1.0 and 1.1) | DIQMTQSPSSLSVSVGERVTITCRASENIRSNLAWYQQKPGKSPKLLVNVAT NLADGVPSRFSGSGSGTDYSLKINSLQPEDFGTYYCQHYWGTTWTFGQGTK LEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTK SFNRGEC (SEQ ID NO: 107) |
| muCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRADAAPTVSIFPPSSEQLTSGGASVVCFLNNFYPKDINVKWKIDGSE RQNGVLNSWTDQDSKDSTYSMSSTLTLTKDEYERHNSYTCEATHKTSTSPI VKSFNRNEC (SEQ ID NO: 108) |
| chCD37-12 | DIVLTQSPASLAVSLGQRATISCRASQSVSTSSYSYLYWFQQKPGQPPKLLIK YASNLASGVPARFSGSGSGTDFTLNIHPVEEEDTATYYCQHSWEIPYTFGGG TKLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSPV TKSFNRGEC (SEQ ID NO: 109) |
| muCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 110) |
| chCD37-38 | QIVLTQSPAIMSASPGEKVTMTCSASSSVTYMHWYQQKSGTSPKRWIYDTS KLASGVPARFSGGGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 111) |
| huCD37-38 | DIVLTQSPASMSASPGERVTMTCSASSSVTYMHWYQQKPGTSPKRWIYDTS KLASGVPARFSGSGSGTSYSLTISSMEAEDAATYYCQQWISNPPTFGGGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 112) |
| muCD37-50 | QIVLTQSPAIMSASPGEKVTMTCSATSSVTYMHWYQQKSGTSPKRWIYDTS KLPYGVPGRFSGSGSGTSYSLTISSMEAEDAATYYCQQWSDNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 113) |
| huCD37-50 | EIVLTQSPATMSASPGERVTMTCSATSSVTYMHWYQQKPGQSPKRWIYDTS NLPYGVPARFSGSGSGTSYSLTISSMEAEDAATYYCQQWSDNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 114) |
| muCD37-51 | QIVLTQSPAIMSASPGEKVTMTCSATSSVTYMHWYQQKSGTSPKRWIYDTS KLASGVPARFSGSGSGTSYSLTISNMEAEDAATYYCQQWSSNPPTFGSGTKL EIKRADAAPTVSIFPPSSEQLTSGGASVVCFLNNFYPKDINVKWKIDGSERQN GVLNSWTDQDSKDSTYSMSSTLTLTKDEYERHNSYTCEATHKTSTSPIVKSF NRNEC (SEQ ID NO: 115) |
| huCD37-51 | EIVLTQSPATMSASPGERVTMTCSATSSVTYMHWYQQKPGQSPKRWIYDTS KLASGVPARFSGSGSGTSYSLTISSMEAEDAATYYCQQWSSNPPTFGQGTKL EIKRTVAAPSVFIFPPSDEQLKSGTASVVCLLNNFYPREAKVQWKVDNALQS GNSQESVTEQDSKDSTYSLSSTLTLSKADYEKHKVYACEVTHQGLSSPVTKS FNRGEC (SEQ ID NO: 116) |

TABLE 6-continued

Full-length light chain amino acid sequences

| Antibody | Full-length Light Chain Amino Acid Sequence (SEQ ID NO) |
|---|---|
| muCD37-56 | QIVLTQSPAFMSASPGDKVTMTCSASSSVTYMHWYQQKSGTSPKRWIYDTS<br>KLASGVPARFSGGGSGTSYSLTISTMEAEDAATYYCQQWISDPPTFGGGTKL<br>EIKRADAAPTVSIFPPSSEQLTSGGASVVCFLNNFYPKDINVKWKIDGSERQN<br>GVLNSWTDQDSKDSTYSMSSTLTLTKDEYERHNSYTCEATHKTSTSPIVKSF<br>NRNEC (SEQ ID NO: 117) |
| huCD37-56 | DIVLTQSPAFMSASPGEKVTMTCSASSSVTYMHWYQQKPDQSPKRWIYDTS<br>NLASGVPSRFSGGGSGTDYSLTISSMEAEDAATYYCQQWISDPPTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC (SEQ ID NO: 118) |
| muCD37-57 | QIVLTQSPAIMSASPGEKVTMTCSATSSVTYMHWYQQKSGTSPKRWIYDTS<br>KLASGVPARFSGSGSGTSYSLTISSMEAEDAATYYCQQWSDNPPTFGSGTKL<br>EIKRADAAPTVSIFPPSSEQLTSGGASVVCFLNNFYPKDINVKWKIDGSERQN<br>GVLNSWTDQDSKDSTYSMSSTLTLTKDEYERHNSYTCEATHKTSTSPIVKSF<br>NRNEC (SEQ ID NO: 119) |
| huCD37-57 | EIVLTQSPATMSASPGERVTMTCSATSSVTYMHWYQQKPGQSPRRWIYDTS<br>NLASGVPARFSGSGSGTSYSLTISSMEAEDAATYYCQQWSDNPPTFGQGTKL<br>EIKRTVAAPSVFIFPPSDEQLKSGTASVVCLLNNFYPREAKVQWKVDNALQS<br>GNSQESVTEQDSKDSTYSLSSTLTLSKADYEKHKVYACEVTHQGLSSPVTKS<br>FNRGEC (SEQ ID NO: 120) |

Also provided are polypeptides that comprise: (a) a polypeptide having at least about 90% sequence identity to SEQ ID NOs:88-104; and/or (b) a polypeptide having at least about 90% sequence identity to SEQ ID NOs:105-120. In certain embodiments, the polypeptide comprises a polypeptide having at least about 95%, at least about 96%, at least about 97%, at least about 98%, or at least about 99% sequence identity to SEQ ID NOs:88-120. Thus, in certain embodiments, the polypeptide comprises (a) a polypeptide having at least about 95% sequence identity to SEQ ID NOs:88-104, and/or (b) a polypeptide having at least about 95% sequence identity to SEQ ID NOs:105-120. In certain embodiments, the polypeptide comprises (a) a polypeptide having the amino acid sequence of SEQ ID NOs:88-104; and/or (b) a polypeptide having the amino acid sequence of SEQ ID NOs:105-120. In certain embodiments, the polypeptide is an antibody and/or the polypeptide specifically binds CD37. In certain embodiments, the polypeptide is a murine, chimeric, or humanized antibody that specifically binds CD37. In certain embodiments, the polypeptide having a certain percentage of sequence identity to SEQ ID NOs:88-120 differs from SEQ ID NOs:88-120 by conservative amino acid substitutions only.

In certain embodiments, the CD37 antibody can be the antibody produced from a hybridoma selected from the group consisting of consisting of ATCC Deposit Designation PTA-10664, deposited with the ATCC on Feb. 18, 2010, ATCC Deposit Designation PTA-10665, deposited with the ATCC on Feb. 18, 2010, ATCC Deposit Designation PTA-10666, deposited with the ATCC on Feb. 18, 2010, ATCC Deposit Designation PTA-10667 deposited with the ATCC on Feb. 18, 2010, ATCC Deposit Designation PTA-10668, deposited with the ATCC on Feb. 18, 2010, ATCC Deposit Designation PTA-10669, deposited with the ATCC on Feb. 18, 2010, and ATCC Deposit Designation PTA-10670, deposited with the ATCC on Feb. 18, 2010 (ATCC at 10801 University Boulevard, Manassas, Va. 20110). In certain embodiments, the antibody comprises the VH-CDRs and the VL-CDRS of the antibody produced from a hybridoma selected from the group consisting of PTA-10665, PTA-10666, PTA-10667, PTA-10668, PTA-10669, and PTA-10670.

In certain embodiments, the CD37 antibody can comprise a light chain encoded by the recombinant plasmid DNA phuCD37-3LC (ATCC Deposit Designation PTA-10722, deposited with the ATCC on Mar. 18, 2010). In certain embodiments, the CD37 antibody can comprise a heavy chain encoded by the recombinant plasmid DNA phuCD37-3HCv.1.0 (ATCC Deposit Designation PTA-10723, deposited with the ATCC on Mar. 18, 2010). In certain embodiments, the CD37 antibody can comprise a light chain encoded by the recombinant plasmid DNA phuCD37-3LC (PTA-10722) and a heavy chain encoded by the recombinant plasmid DNA phuCD37-3HCv.1.0 (PTA-10723). In certain embodiments, the CD37 antibody can comprise the VL-CDRs encoded by the recombinant plasmid DNA phuCD37-3LC (PTA-10722) and the VH-CDRs encoded by the recombinant plasmid DNA phuCD37-3HCv.1.0 (PTA-10723).

Particularly preferred antibodies are humanized monoclonal antibodies described herein. Examples include, but are not limited to, huN901, huMy9-6, huB4, huC242, a humanized monoclonal anti-Her2 antibody (e.g., trastuzumab), bivatuzumab, sibrotuzumab, CNTO95, huDS6, and rituximab (see, e.g., U.S. Pat. Nos. 5,639,641 and 5,665,357, U.S. Provisional Patent Application No. 60/424,332 (which is related to U.S. Pat. No. 7,557,189), International (PCT) Patent Application Publication WO 02/16401, Pedersen et al., supra, Roguska et al., supra, Liu et al., supra, Nadler et al., supra, Colomer et al., *Cancer Invest.*, 19: 49-56 (2001), Heider et al., *Eur. J. Cancer*, 31A: 2385-2391 (1995), Welt et al., *J. Clin. Oncol.*, 12: 1193-1203 (1994), and Maloney et al., *Blood*, 90: 2188-2195 (1997)). Other humanized monoclonal antibodies are known in the art and can be used in connection with the invention.

In one embodiment, the cell-binding agent is an humanized anti-folate antibody or antigen binding fragment thereof that specifically binds a human folate receptor 1, wherein the antibody comprises: (a) a heavy chain CDR1 comprising GYFMN (SEQ ID NO: 1); a heavy chain CDR2 comprising RIHPYDGDTFYNQXaa₁FXaa₂Xaa₃ (SEQ ID NO: 2); and a heavy chain CDR3 comprising YDGSRAMDY (SEQ ID NO: 3); and (b) a light chain CDR1 comprising KASQSVS-FAGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa₁ is selected from K, Q, H, and R; Xaa₂ is selected from Q, H, N, and R; and Xaa₃ is selected from G, E, T, S, A, and V. Preferably, the heavy chain CDR2 sequence comprises RIHPYDGDTFYNQKFQG (SEQ ID NO: 7).

In another embodiment, the anti-folate antibody is a humanized antibody or antigen binding fragment thereof that specifically binds the human folate receptor 1 comprising the heavy chain having the amino acid sequence of

```
                                            (SEQ ID NO: 8)
QVQLVQSGAEVVKPGASVKISCKASGYTFTGYFMNWVKQSPGQSLEWIG

RIHPYDGDTFYNQKFQGKATLTVDKSSNTAHMELLSLTSEDFAVYYCTR

YDGSRAMDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK.
```

In another embodiment, the anti-folate antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate antibody is a humanized antibody or antigen binding fragment thereof comprising a heavy chain variable domain at least about 90%, 95%, 99% or 100% identical to QVQLVQS-GAEVVKPGASVKISCK-ASGYTFTGYFMNWVKQSPGQSLEWIGRIHPYDG DTFYNQKFQGKATLTVDKSSNTAHMELLSLTSED-FAVYYCTRYDGSRAMDYWGQG TTVTVSS (SEQ ID NO: 9), and a light chain variable domain at least about 90%, 95%, 99% or 100% identical to

```
                                           (SEQ ID NO: 10)
DIVLTQSPLSLAVSLGQPAIISCKASQSVSFAGTSLMHWYHQKPGQQPR
LLIYRASNLEAGVPDRFSGSGSKTDFTLNISPVEAEDAATYYCQQSREY
PYTFGGGTKLEIKR;
or
                                           (SEQ ID NO: 11)
DIVLTQSPLSLAVSLGQPAIISCKASQSVSFAGTSLMHWYHQKPGQQPR
LLIYRASNLEAGVPDRFSGSGSKTDFTLTISPVEAEDAATYYCQQSREY
PYTFGGGTKLEIKR.
```

While the cell-binding agent preferably is an antibody, the cell-binding agent also can be a non-antibody molecule. Suitable non-antibody molecules include, for example, interferons (e.g., alpha, beta, or gamma interferon), lymphokines (e.g., interleukin 2 (IL-2), IL-3, IL-4, or IL-6), hormones (e.g., insulin), growth factors (e.g., EGF, TGF-alpha, FGF, and VEGF), colony-stimulating factors (e.g., G-CSF, M-CSF, and GM-CSF (see, e.g., Burgess, *Immunology Today*, 5: 155-158 (1984)), somatostatin, and transferrin (see, e.g., O'Keefe et al., *J. Biol. Chem.*, 260: 932-937 (1985)). For example, GM-CSF, which binds to myeloid cells, can be used as a cell-binding agent to target acute myelogenous leukemia cells. In addition, IL-2, which binds to activated T-cells, can be used for prevention of transplant graft rejection, for therapy and prevention of graft-versus-host disease, and for treatment of acute T-cell leukemia. Epidermal growth factor (EGF) can be used to target squamous cancers such as lung cancer and head and neck cancer. Somatostatin can be used to target neuroblastoma cells and other tumor cell types.

The conjugate can comprise any suitable cytotoxic agents. A "cytotoxic agent," as used herein, refers to any compound that results in the death of a cell, induces cell death, or decreases cell viability. Suitable cytotoxic agents include, for example, maytansinoids and conjugatable ansamitocins (see, for example, International Patent Application No. PCT/US11/59131, filed Nov. 3, 2011), taxoids, CC-1065 and CC-1065 analogs, and dolastatin and dolastatin analogs. In a preferred embodiment of the invention, the cytotoxic agent is a maytansinoid, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl) +/−C-19-dechloro (U.S. Pat. Nos. 4,361,650 and 4,307,016) (prepared by demethylation using *Streptomyces* or *Actinomyces* or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with $H_2S$ or $P_2S_5$), (2) C-14-alkoxymethyl (demethoxy/$CH_2OR$) (U.S. Pat. No. 4,331,598), (3) C-14-hydroxymethyl or acyloxymethyl ($CH_2OH$ or $CH_2OAc$) (U.S. Pat. No. 4,450,254) (prepared from *Nocardia*), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from *Trewia nudiflora*), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

In a preferred embodiment of the invention, the conjugate utilizes the thiol-containing maytansinoid DM1, also known as $N^{2'}$-deacetyl-$N^{2'}$-(3-mercapto-1-oxopropyl)-maytansine, as the cytotoxic agent. The structure of DM1 is represented by formula (I):

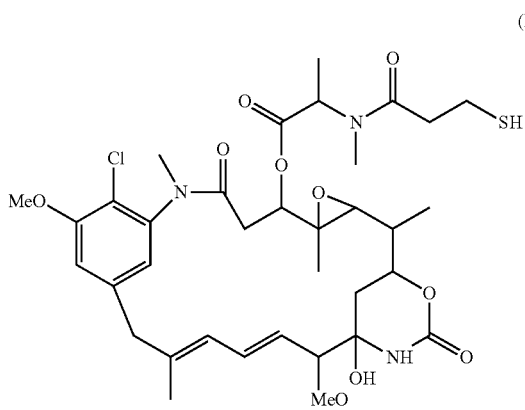

(I)

In another preferred embodiment of the invention, the conjugate utilizes the thiol-containing maytansinoid DM4, also known as N2'-deacetyl-N2'-(4-methyl-4-mercapto-1-oxopentyl)-maytansine, as the cytotoxic agent. The structure of DM4 is represented by formula (II):

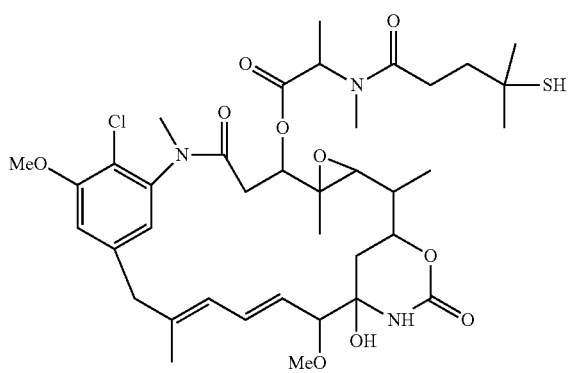

(II)

Other maytansinoids may be used in the context of the invention, including, for example, thiol and disulfide-containing maytansinoids bearing a mono or di-alkyl substitution on the carbon atom bearing the sulfur atom. Particularly preferred is a maytansinoid having at the C-3 position (a) C-14 hydroxymethyl, C-15 hydroxy, or C-20 desmethyl functionality, and (b) an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Additional maytansinoids for use in the context of the invention include compounds represented by formula (III):

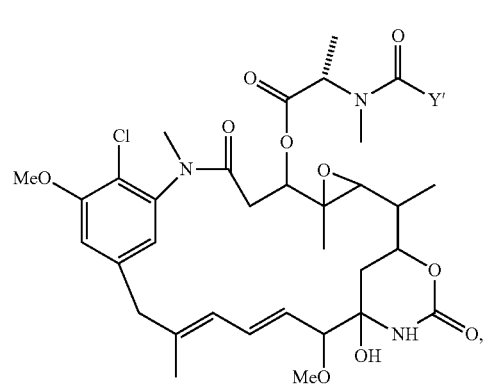

(III)

wherein Y' represents $(CR_7R_8)_l(CR_9=CR_{10})_p(C\equiv C)_qA_o(CR_5R_6)_mD_u$
$(CR_{11}=CR_{12})_r(C\equiv C)_sB_t(CR_3R_4)_nCR_1R_2SZ$, wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein A, B, D are cycloalkyl or cycloalkenyl having 3-10 carbon atoms, simple or substituted aryl, or heterocyclic aromatic, or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic, or heterocycloalkyl radical, wherein l, m, n, o, p, q, r, s, and t are each independently zero or an integer from 1 to 5, provided that at least two of l, m, n, o, p, q, r, s and t are not zero at any one time, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic, or heterocycloalkyl radical.

Preferred embodiments of formula (III) include compounds of formula (III) wherein (a) $R_1$ is H, $R_2$ is methyl and Z is H, (b) $R_1$ and $R_2$ are methyl and Z is H, (c) $R_1$ is H, $R_2$ is methyl, and Z is —$SCH_3$, and (d) $R_1$ and $R_2$ are methyl, and Z is —$SCH_3$.

Such additional maytansinoids also include compounds represented by formula (IV-L), (IV-D), or (IV-D,L):

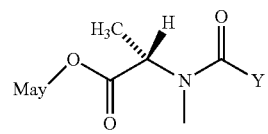

(IV-L)

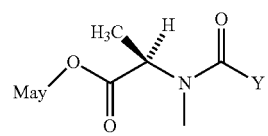

(IV-D)

-continued

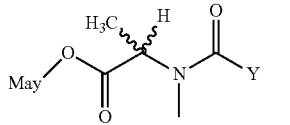
(IV-D,L)

wherein Y represents $(CR_7R_8)_l(CR_5R_6)_m(CR_3R_4)_n CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, wherein Z is H, SR, or COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical, and wherein May represents a maytansinoid which bears the side chain at C-3, C-14 hydroxymethyl, C-15 hydroxy, or C-20 desmethyl.

Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, and $R_8$ are each H, l and m are each 1, n is 0, and Z is H, (b) $R_1$ and $R_2$ are methyl, $R_5$, $R_6$, $R_7$, $R_8$ are each H, l and m are 1, n is 0, and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Preferably the cytotoxic agent is represented by formula (IV-L).

Additional preferred maytansinoids also include compounds represented by formula (V):

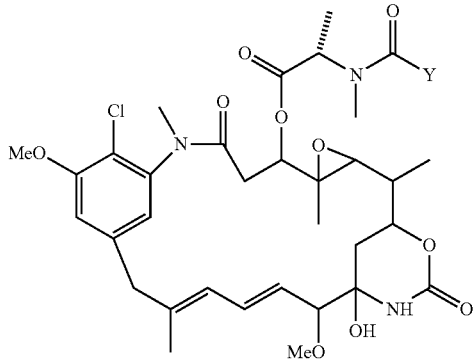
(V)

wherein Y represents $(CR_7R_8)_l(CR_5R_6)_m(CR_3R_4)_n CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein (a) $R_1$ is H, $R_2$ is methyl, $R_5$, $R_6$, $R_7$, and $R_8$ are each H; l and m are each 1; n is 0; and Z is H, (b) $R_1$ and $R_2$ are methyl; $R_5$, $R_6$, $R_7$, $R_8$ are each H, l and m are 1; n is 0; and Z is H, (c) $R_1$ is H, $R_2$ is methyl, $R_5$, $R_6$, $R_7$, and $R_8$ are each H, l and m are each 1, n is 0, and Z is —$SCH_3$, or (d) $R_1$ and $R_2$ are methyl, $R_5$, $R_6$, $R_7$, $R_8$ are each H, l and m are 1, n is 0, and Z is —$SCH_3$.

Still further preferred maytansinoids include compounds represented by formula (VI-L), (VI-D), or (VI-D,L):

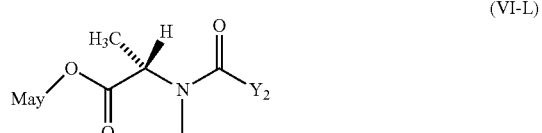
(VI-L)

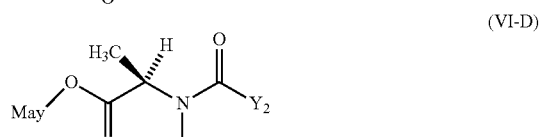
(VI-D)

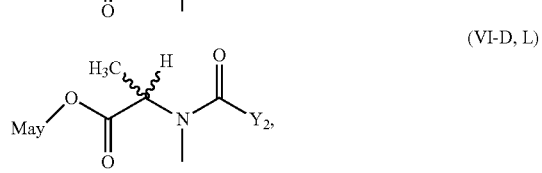
(VI-D, L)

wherein $Y_2$ represents $(CR_7R_8)_l(CR_5R_6)_m(CR_3R_4)_n CR_1R_2SZ_2$, wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, and n are each independently an integer of from 1 to 5, and in addition n can be zero, wherein $Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical, and wherein May is the macrocyclic ring structure of the maytansinoid.

Additional preferred maytansinoids include compounds represented by formula (VII):

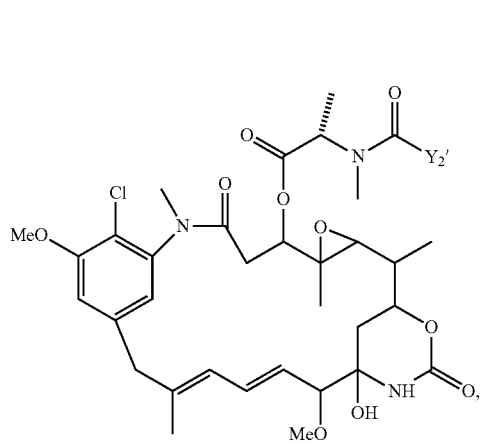

(VII)

wherein $Y_2'$ represents
$(CR_7R_8)_l(CR_9=CR_{10})_p(C\equiv C)_qA_o(CR_5R_6)_mD_u$
$(CR_u=CR_{12})_r(C\bullet C)_sB_t(CR_3R_4)_nCR_1R_2SZ_2$, wherein $R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition $R_2$ can be H, wherein A, B, and D each independently is cycloalkyl or cycloalkenyl having 3 to 10 carbon atoms, simple or substituted aryl, or heterocyclic aromatic or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, n, o, p, q, r, s, and t are each independently zero or an integer of from 1 to 5, provided that at least two of l, m, n, o, p, q, r, s and t are not zero at any one time, and wherein $Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (VII) include compounds of formula (VII), wherein $R_1$ is H and $R_2$ is methyl.

In addition to maytansinoids, the cytotoxic agent used in the conjugate can be a taxane or derivative thereof. Taxanes are a family of compounds that includes paclitaxel (Taxol®), a cytotoxic natural product, and docetaxel (Taxotere®), a semi-synthetic derivative, which are both widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell-binding agents.

A preferred taxane for use in the preparation of a cytotoxic conjugate is the taxane of formula (VIII):

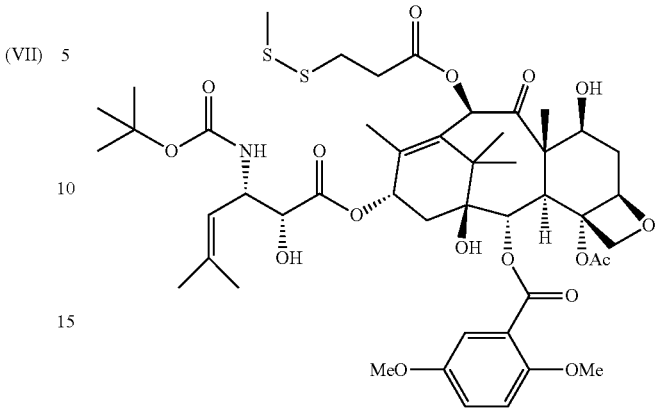

(VIII)

Methods for synthesizing taxanes that can be used in the context of the invention, along with methods for conjugating taxanes to cell-binding agents such as antibodies, are described in detail in U.S. Pat. Nos. 5,416,064, 5,475,092, 6,340,701, 6,372,738, 6,436,931, 6,596,757, 6,706,708, 6,716,821, and 7,390,898.

The cytotoxic also can be CC-1065 or a derivative thereof. CC-1065 is a potent anti-tumor antibiotic isolated from the culture broth of *Streptomyces zelensis*. CC-1065 is about 1000-fold more potent in vitro than commonly used anti-cancer drugs, such as doxorubicin, methotrexate, and vincristine (Bhuyan et al., *Cancer Res.*, 42: 3532-3537 (1982)). CC-1065 and its analogs are disclosed in U.S. Pat. Nos. 5,585,499, 5,846,545, 6,340,701, and 6,372,738. The cytotoxic potency of CC-1065 has been correlated with its alkylating activity and its DNA-binding or DNA-intercalating activity. These two activities reside in separate parts of the molecule. In this respect, the alkylating activity is contained in the cyclopropapyrroloindole (CPI) subunit and the DNA-binding activity resides in the two pyrroloindole subunits of CC-1065.

Several CC-1065 analogs are known in the art and also can be used as the cytotoxic agent in the conjugate (see, e.g., Warpehoski et al., *J. Med. Chem.*, 31: 590-603 (1988)). A series of CC-1065 analogs has been developed in which the CPI moiety is replaced by a cyclopropabenzindole (CBI) moiety (Boger et al., *J. Org. Chem.*, 55: 5823-5833 (1990), and Boger et al., *Bioorg. Med. Chem. Lett.*, 1: 115-120 (1991)). These CC-1065 analogs maintain the high in vitro potency of the parental drug, without causing delayed toxicity in mice. Like CC-1065, these compounds are alkylating agents that covalently bind to the minor groove of DNA to cause cell death.

The therapeutic efficacy of CC-1065 analogs can be greatly improved by changing the in vivo distribution through targeted delivery to a tumor site, resulting in lower toxicity to non-targeted tissues, and thus, lower systemic toxicity. To this end, conjugates of analogs and derivatives of CC-1065 with cell-binding agents that specifically target tumor cells have been generated (see, e.g., U.S. Pat. Nos. 5,475,092, 5,585,499, and 5,846,545). These conjugates typically display high target-specific cytotoxicity in vitro, and anti-tumor activity in human tumor xenograft models in mice (see, e.g., Chari et al., *Cancer Res.*, 55: 4079-4084 (1995)).

Methods for synthesizing CC-1065 analogs are described in detail in U.S. Pat. Nos. 5,475,092, 5,585,499, 5,846,545, 6,534,660, 6,586,618, 6,756,397, and 7,329,760.

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs also can be used as the cytotoxic agent of the invention. Doxarubicin and daunorubicin compounds (see, e.g., U.S. Pat. No. 6,630,579) can also be used as the cytotoxic agent.

The cell-binding agent cytotoxic agent conjugates may be prepared by in vitro methods. In order to link a cytotoxic agent to the antibody, a linking group is used. Suitable linking groups are well known in the art and include disulfide groups, acid labile groups, photolabile groups, peptidase labile groups, and esterase labile groups, as well as noncleavable linking groups. For example, the cell binding agent can be chemically coupled to the cytotoxic agent via chemical bonds selected from the group consisting of disulfide bonds, acid labile bonds, photolabile bonds, peptidase labile bonds, thioether bonds, and esterase labile bonds.

In accordance with the invention, the cell-binding agent is linked with the cytotoxic agent via a bifunctional crosslinking reagent. As used herein, a "bifunctional crosslinking reagent" refers to a reagent that possesses two reactive groups; one of which is capable of reacting with a cell-binding agent, while the other one is capable of reacting with the cytotoxic agent to link the cell-binding agent with the cytotoxic agent, thereby forming a conjugate.

Any suitable bifunctional crosslinking reagent can be used in connection with the invention, so long as the linker reagent provides for retention of the therapeutic, e.g., cytotoxicity, and targeting characteristics of the cytotoxic agent and the cell-binding agent, respectively, without undue toxicity. Preferably, the linker molecule joins the cytotoxic agent to the cell-binding agent through chemical bonds (as described above), such that the cytotoxic agent and the cell-binding agent are chemically coupled (e.g., covalently bonded) to each other.

In one embodiment, the bifunctional crosslinking reagent comprises non-cleavable linkers. A non-cleavable linker is any chemical moiety that is capable of linking a cytotoxic agent, such as a maytansinoid, a taxane, or a CC-1065 analog, to a cell-binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the cytotoxic agent or the cell-binding agent remains active.

Suitable crosslinking reagents that form non-cleavable linkers between a cytotoxic agent and the cell-binding agent are well known in the art. In one embodiment, the cytotoxic agent is linked to the cell-binding agent through a thioether bond. Examples of non-cleavable linkers include linkers having a maleimido- or haloacetyl-based moiety for reaction with the cytotoxic agent. Such bifunctional crosslinking agents are well known in the art (see U.S. Patent Application Publication Nos. 2010/0129314, 2009/0274713, 2008/0050310, 20050169933, 2009/0274713, 2010/0129314, and those available from Pierce Biotechnology Inc. P.O. Box 117, Rockland, Ill. 61105, USA) and include, but not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-(O-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME), 1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl) aminobenzoate (sulfo-SIAB), m-Maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy)sulfosuccimido ester (sulfo-EMCS), N-(γ-maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal. Preferably, the bifunctional crosslinking reagent is SMCC.

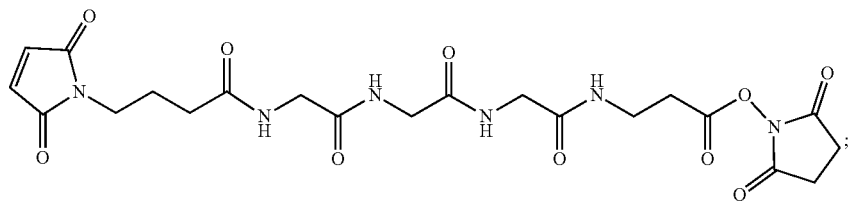

(CX1-1)

-continued

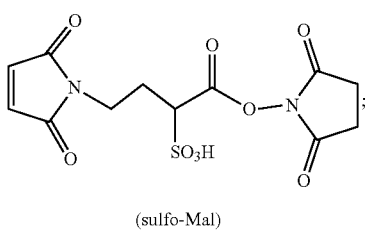

(sulfo-Mal)

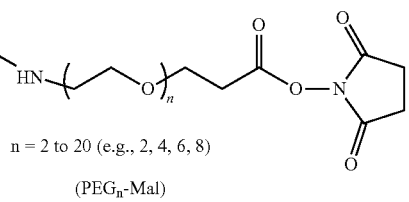

n = 2 to 20 (e.g., 2, 4, 6, 8)

(PEG$_n$-Mal)

In one embodiment, the linking reagent is a cleavable linker. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., *Proc. Natl. Acad. Sci. USA*, 79: 626-629 (1982), and Umemoto et al., *Int. J. Cancer*, 43: 677-684 (1989)). In one embodiment, the cleavable linker is cleaved under mild conditions, i.e., conditions within a cell under which the activity of the cytotoxic agent is not affected.

In another embodiment, the cytotoxic agent is linked to a cell-binding agent through a disulfide bond. The linker molecule comprises a reactive chemical group that can react with the cell-binding agent. Preferred reactive chemical groups for reaction with the cell-binding agent are N-succinimidyl esters and N-sulfosuccinimidyl esters. Additionally the linker molecule comprises a reactive chemical group, preferably a dithiopyridyl group, that can react with the cytotoxic agent to form a disulfide bond. Bifunctional crosslinking reagents that enable the linkage of the cell-binding agent with the cytotoxic agent via disulfide bonds are known in the art and include, for example, N-succinimidyl 3-(2-pyridyldithio)propionate (SPDP) (see, e.g., Carlsson et al., *Biochem. J.*, 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and N-succinimidyl-4-(2-pyridyldithio)2-sulfo butanoate (sulfo-SPDB) (see, e.g., U.S. Application Publication 2009/0274713). Other bifunctional crosslinking reagents that can be used to introduce disulfide groups are known in the art and are described in U.S. Pat. Nos. 6,913,748, 6,716,821 and U.S. Patent Application Publications 2009/0274713 and 2010/0129314, all of which are incorporated herein in its entirety by reference.

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, μ,ω-dicarboxylic acids of the general formula (IX):

HOOC—X$_l$—Y$_n$—Z$_m$—COOH   (IX), wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent Application Publication No. 2005/0169933 A1.

The following examples further illustrate the invention but, of course, should not be construed as in any way limiting its scope.

Example 1

Humanized CD37-3 antibody was reacted with the heterobifunctional crosslinking reagent SMCC and the maytansinoid DM1 using a previously described process (e.g. U.S. Pat. No. 5,208,020), as well as the one-step process that is the subject of the present application.

For the previously described process, huCD37-3 (15 mg/mL) first was reacted with SMCC (6.5-fold molar excess relative to the amount of antibody) to form the modified antibody. The modification reaction was performed at 16° C. in 50 mM sodium phosphate buffer (pH 6.9) containing 2 mM EDTA and 10% DMA for 90 minutes. The reaction was quenched with 1 M acetate to adjust the pH to 4.5 and the modified antibody was purified using a column of Sephadex G-25F resin equilibrated and eluted in 20 mM sodium acetate (pH 4.5) containing 2 mM EDTA. After purification, the modified antibody (5 mg/mL) was reacted with the maytansinoid DM1 (6.8-fold molar excess relative to the amount of antibody; 1.3-fold excess relative to the measured amount of linker on the antibody) to form the conjugated antibody. The conjugation reaction was performed at 20° C. in 20 mM sodium acetate buffer (pH 5.0) containing 2 mM EDTA and 5% DMA for approximately 20 hours. The reaction mixture was then purified using a column of Sephadex G-25F resin equilibrated and eluted in 10 mM sodium succinate (pH 5.0).

For the inventive process, huCD37-3 (2.5 mg/mL) was mixed with DM1 (6.2-fold molar excess relative to the amount of antibody) and then with SMCC (5.2-fold excess relative to the amount of antibody). The reaction was performed at 20° C. in 50 mM EPPS [4-(2-Hydroxyethyl)-1-piperazinepropanesulfonic acid] buffer (pH 8.1) containing 2 mM EDTA and 10% DMA for approximately 4 hours. The reaction was quenched by adding 1 M acetate to adjust the pH to 5.0. The reaction mixture was then held at 2-8° C. for approximately 20 hours. After holding, the reaction mixture was filtered through a 0.2 μm PVDF filter and purified and diafiltered into 10 mM sodium succinate (pH 5.0) using Tangential Flow Filtration (TFF).

Conjugate derived from the two processes was analyzed by: UV spectroscopy for concentration and cytotoxic agent loading (Maytansinoid to Antibody Ratio, MAR); Mass Spectrometry for determination of unconjugated linker level; reduced SDS PAGE electrophoresis for determination of level of non-reducible species; SEC-HPLC for determination of conjugate monomer; and stability on storage with respect to conjugate monomer and free maytansinoid release.

Concentration and Maytansinoid to Antibody Ratio (MAR) were determined by measuring the absorbance of the conjugate at 252 and 280 nm in a UV-VIS spectrophotometer and using the molar extinction coefficients of DM1 and antibody at the two wavelengths to calculate the molar concentrations of antibody and DM1.

The un-conjugated linker level of the conjugates was analyzed by mass spectrometry: peak areas of individual conjugate species (including conjugates with or without un-conjugated linkers) were measured; the un-conjugated linker level was calculated by the ratio of the sum of areas containing un-conjugated linkers (weighted by the number of linkers) to the sum of areas of all conjugate species (also weighted by the number of linkers).

The non-reducible species level of the conjugates was analyzed by reduced SDS gel electrophoresis: peak areas of individual reduced conjugate species (including reduced light chain, reduced heavy chain, cross-linked light-light chains, cross-linked light-heavy chains, etc.) were measured; the non-reducible species level was calculated by the ratio of the sum of areas of non-reducible species to the sum of areas of all species.

The monomer level of the conjugates was analyzed by size exclusion HPLC: peak areas of monomer, dimer, aggregates and low molecular weight species were measured using an absorbance detector set to a wavelength of 252 nm or 280 nm; the monomer level was calculated by the ratio of the monomer area to the total area.

The amount of free maytansinoid present in the conjugate was analyzed by dual column (HiSep and C18 columns) HPLC: peak areas of total free maytansinoid species (eluted in the gradient and identified by comparison of elution time with known standards) were measured using an absorbance detector set to a wavelength of 252 nm; the amount of free maytansinoid was calculated using a standard curve generated by the peak areas of known amount of standards.

As shown in Table 1 below, conjugate manufactured using the inventive process was superior to that manufactured using the previously described process with respect to unconjugated linker, non-reducible species, and conjugate monomer. In addition, the stability of conjugate made by the inventive process was significantly superior with respect to free maytansinoid release after storage for five months at 4° C. Monomer levels of conjugates made by both processes were stable.

TABLE 7

Comparison of key properties of CD37-3 conjugate manufactured by the inventive process compared to previous process

| | Previous Process | Inventive Process |
|---|---|---|
| Conjugate concentration | 3.9 | 8.1 |
| Maytansinoid to Antibody ratio | 4.1 | 3.4 |
| Unconjugated Linker (%) | 12 | <1 |
| Nonreducible species (%) | 9.4 | 0.9 |
| Conjugate monomer, (%) (t = 0) | 97.8 | 98.9 |
| Conjugate monomer, (%) (after 5 months at 4° C.) | 97.8 | 98.4 |

TABLE 7-continued

Comparison of key properties of CD37-3 conjugate manufactured by the inventive process compared to previous process

| | Previous Process | Inventive Process |
|---|---|---|
| Free Maytansinoid, (%) (t = 0) | 0.4 | 0.2 |
| Free Maytansinoid, (%) (after 5 months at 4° C.) | 3.3 | 0.5 |

The results of the experiments reflected in this example demonstrate an improved processes for preparing cell-binding agent-cytotoxic agent conjugates that are of substantially high purity. In addition to the improvements in conjugate purity and stability from using the inventive process, there are also improvements in processing time and convenience, due to elimination of two processing steps (modification reaction and purification of the modified antibody).

Example 2

Humanized Folate Receptor antibody huMov19 (see U.S. Application Publication 2012/0009181) was reacted with the heterobifunctional crosslinking reagent sulfo-SPDB and the maytansinoid DM4 using two previously described processes, as well as the improved process that is the subject of the present application.

For the previously described Process A (two-step process, e.g. Chari et al., U.S. Pat. No. 5,208,020), huMov19 antibody (20 mg/mL) first was reacted with sulfo-SPDB (5.7-fold molar excess relative to the amount of antibody, dissolved in DMA, dimethylacetamide) to form the modified antibody. The modification reaction was performed at 20° C. in 50 mM EPPS (4-(2-hydroxyethyl)piperazine-1-propanesulfonic acid) buffer (pH 8.1) containing 5% DMA for 180 minutes. The modified antibody was purified using a column of Sephadex G-25F resin equilibrated and eluted in 50 mM EPPS (pH 8.1) with 2 mM EDTA (Ethylenediaminetetraacetic acid). After purification, the modified antibody (5.0 mg/mL) was reacted with the maytansinoid DM4 (Dissolved in DMA; 9.7-fold molar excess relative to the amount of antibody; 1.7-fold excess relative to the measured amount of linker on the antibody) to form the conjugated antibody. The conjugation reaction was performed at room temperature in 50 mM EPPS (pH 8.1) containing 2 mM EDTA and 5% DMA for approximately 18 hours. The reaction mixture was then purified using a column of Sephadex G-25F resin equilibrated and eluted in 10 mM sodium succinate (pH 5.0).

For the previously described Process B (one-pot process, Dai et al., U.S. Pat. No. 7,811,572), huMov19 antibody (10 mg/mL) first was reacted with sulfo-SPDB (4.9-fold molar excess relative to the amount of antibody, dissolved in DMA) to form the modified antibody. The modification reaction was performed at 20° C. in 50 mM EPPS buffer (pH 7.5) containing 2 mM EDTA and 10% DMA for 60 minutes. The modified antibody was not purified before the conjugation reaction. Instead, the un-purified modified antibody was reacted at 10 mg/mL with the maytansinoid DM4 (8.3-fold molar excess relative to the amount of antibody, dissolved in DMA) to form the conjugated antibody. The conjugation reaction was performed at room temperature in 50 mM EPPS buffer (pH 7.5) containing 2 mM EDTA and 10% DMA for approximately 18 hours. The reaction mixture was then purified using a column of Sephadex G-25F resin equilibrated and eluted in 10 mM sodium succinate (pH 5.0).

For the inventive process in which Sephadex G-25 was used (Process C, one-step process) to purify the conjugate, huMov19 antibody (6.0 mg/mL) was mixed with DM4 (9.7-fold molar excess relative to the amount of antibody, dissolved in DMA) and then sulfo-SPDB (5.7-fold excess relative to the amount of antibody, dissolved in DMA) was added. The reaction was performed at 20° C. in 50 mM EPPS buffer (pH 8.1) containing 2 mM EDTA and 10% DMA for approximately 20 hours. The reaction mixture was then purified using a column of Sephadex G-25F resin equilibrated and eluted in 10 mM sodium succinate (pH 5.0).

For the inventive process in which tangential flow filtration (TFF) (Process D, one-step process) was used to purify the conjugate, huMov19 antibody (5.0 mg/mL) was mixed with DM4 (10.2-fold molar excess relative to the amount of antibody, dissolved in DMA) and then with sulfo-SPDB (6.0-fold excess relative to the amount of antibody, dissolved in DMA). The reaction was performed at 20° C. in 50 mM EPPS buffer (pH 8.5) containing 2 mM EDTA and 10% DMA for approximately 20 hours. The reaction mixture was then purified and diafiltered using a TFF into 10 mM sodium succinate (pH 5.0).

Conjugate derived from the different processes was analyzed by: UV spectroscopy (for concentration and maytansinoid to antibody ratio, MAR); reversed phase HPLC for determination of Free Maytansinoid; Mass Spectrometry for determination of unconjugated linker level and mass distribution profile; reduced SDS PAGE electrophoresis for determination of level of non-reducible species; non-reduced SDS PAGE electrophoresis for determination of level of fragmentation; SEC-HPLC for determination of conjugate monomer. Stability on storage was assessed with respect to conjugate monomer and free maytansinoid release. Additional details on the analytical methodologies are provided in Example 1.

As shown in Table 8 below, conjugate manufactured using the inventive process was superior to that manufactured using the previously described processes with respect to monomer. Conjugate manufactured using the one-pot and one-step processes in which the final purification of conjugate was performed using Sephadex G-25, Processes B and C, respectively, had a higher level of free maytansinoid than conjugate manufactured using the two step process, Process A. However, when a different final purification process, TFF, was used (Process D), the level of free maytansinoid was very low and comparable to that seen with the two-step process, both after initial purification and after storage at 4° C. for six weeks. With respect to other important conjugate attributes (e.g. fragmentation, non-reducible species, mass distribution profile and unconjugated linker), conjugate manufactured using the inventive process was equivalent to that manufactured by the previously described processes.

TABLE 8

Comparison of key properties of huMov19 conjugate manufactured by the inventive process compared to previous processes

| | Process | | | |
|---|---|---|---|---|
| | Process A* | Process B* | Process C* | Process D** |
| Number of Unit Operations | 5 | 4 | 3 | 3 |
| Concentration (mg/mL) | 1.0 | 1.0 | 1.0 | 4.2 |
| MAR (UV) | 4 | 3.8 | 3.7 | 3.6 |
| Conjugate Monomer, (%) at t = 0 | 94.8 | 97.4 | 98.9 | 98.6 |
| Conjugate Monomer, (%) at t = 6 weeks, 4°C. | 94.4 | 97.5 | 98.8 | 98.1 |

TABLE 8-continued

Comparison of key properties of huMov19 conjugate manufactured by the inventive process compared to previous processes

| | Process | | | |
|---|---|---|---|---|
| | Process A* | Process B* | Process C* | Process D** |
| Free Maytansinoid, (%) at t = 0 | 0.6 | 6.3 | 3.1 | 0.1 |
| Free Maytansinoid, (%) at t = 6 weeks, 4°C. | 0.6 | 5.4 | 2.7 | 0.4 |
| Fragmentation By non-reducing gel-chip (%) | 10 | 14 | 14 | 12 |
| Non-reducible species By reducing gel-chip (%) | 0.7 | 0.8 | 0.7 | 0.5 |
| Mass Distribution Profile (MDP) | Comparable | | | |
| Unconjugated Linker (MDP) | Non-Detectible | | | |

*Purified with Sephadex G-25
**Purified using TFF

The results of the experiments reflected in this example demonstrate an improved processes for preparing cell-binding agent-cytotoxic agent conjugates that are of substantially high purity. In addition to the improvements in conjugate purity and stability from using the inventive process, there are also improvements in processing time and convenience, due to elimination of two processing steps (modification reaction and purification of the modified antibody).

Example 3

This example demonstrates that the one-step process described herein can be used to make conjugates starting with a variety of linkers and maytansinoid cytotoxic agents.

Humanized huN901 antibody was mixed with Maytansinoid (DMlor DM4) and then with Linker (Sulfo-SMCC, SMCC, SPDB, or SPP). The reaction was performed at 20° C. in 50 mM phosphate buffer (pH 7.5) containing 2 mM EDTA and 10% DMA for approximately 20-24 hours. The reaction mixture was then purified using a column of Sephadex G25F resin equilibrated and eluted in 10 mM sodium succinate (pH 5.0).

As shown in Table 9 below, the one-step reaction can be performed on different linker and maytansinoid combinations and yield conjugate with good MAR and monomer levels.

TABLE 9

Making conjugates by using different linker and maytansinoid combinations

| | Linker | DMx | Conjugate MAR | Conjugate Monomer (%) |
|---|---|---|---|---|
| Two-step | SPP | DM1 | 3.5 | 96.8 |
| One-step | SPP | DM1 | 3.4 | 97.5 |
| (Inventive) | SPDB | DM1 | 4.6 | 97.7 |
| | SMCC | DM4 | 4.5 | 95.1 |
| | S-SMCC | DM1 | 3.5 | 98.0 |
| | SPDB | DM4 | 3.8 | 97.3 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing an antibody maytansinoid conjugate comprising the step of: (a) contacting a monoclonal antibody that binds CD37 with a maytansinoid to form a first mixture comprising the antibody and the maytansinoid, then contacting the first mixture with a bifunctional crosslinking reagent comprising a linker, in a solution having a pH of about 4 to about 9 to provide a second mixture comprising (i) the antibody maytansinoid conjugate, wherein the antibody is chemically coupled through the linker to the maytansinoid, (ii) free maytansinoid, and (iii) reaction by-products; and (b) contacting the second mixture with additional maytansinoid to form a third mixture;

and then contacting the third mixture with additional bifunctional crosslinking reagent at a pH of about 4 to about 9 to provide a fourth mixture.

2. The process of claim 1, wherein the process further comprises the step of:

(c) purifying the fourth mixture comprising the antibody maytansinoid conjugate to provide a purified antibody maytansinoid conjugate.

3. The process of claim 2, wherein step (b) is repeated one or more times before step (c) is carried out.

4. The process of claim 3, wherein each repeated step (b) is carried out after about one or more hours following initial step (b).

5. The process of claim 2, further comprising holding the fourth mixture between steps (b)-(c) to release the unstably bound linkers from the antibody.

6. The process of claim 5, wherein the fourth mixture is held for about 20 hours at a temperature of about 2° C. to about 8° C.

7. The process of claim 2, further comprising quenching the fourth mixture between steps (b)-(c) to quench any unreacted maytansinoid and/or unreacted bifunctional crosslinking reagent.

8. The process of claim 4, wherein the mixture is quenched by contacting the fourth mixture with a quenching reagent that reacts with the free maytansinoid.

9. The process of claim 1, wherein the contacting in step (a) occurs in a solution having a pH of about 7 to about 9.

10. The process of claim 1, wherein the contacting in step (a) occurs at a temperature of about 16° C. to about 24° C.

11. The process of claim 1, wherein the maytansinoid comprises a thiol group.

12. The process of claim 11, wherein the maytansinoid is $N^2$-deacetyl-$N^2$-(3-mercapto-1-oxopropyl)-maytansine (DM1) or maytansinoid is $N^2$-deacetyl-$N^2$-(4-methyl-4-mercapto-1-oxopentyl)-maytansine (DM4).

13. The process of claim 1, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

14. The process of claim 1, wherein the bifunctional crosslinking reagent comprises an N-succinimidyl ester moiety, an N-sulfosuccinimidyl ester moiety, a maleimido-based moiety, or a haloacetyl-based moiety.

15. The process of claim 14, wherein the bifunctional crosslinking reagent is selected from the group consisting of N-succinimidyl 3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)2-sulfo butanoate (sulfo-SPDB), N-succinimidyl 4-(maleimidomethyl)cyclohexanecarboxylate (SMCC), PEG-mal, sulfo-Mal, and CX1-1.

16. The process of claim 1, wherein the solution in step (a) comprises a buffering agent selected from the group consisting of a citrate buffer, an acetate buffer, a succinate buffer, and a phosphate buffer.

17. The process of claim 1, wherein the antibody comprises a heavy chain variable region (VH) complementary determining region 1 (CDR1) sequence of SEQ ID NO: TSGVS (SEQ ID NO: 121), VH CDR2 sequence of VIWGDGSTN (SEQ ID NO: 122), VH CDR3 sequence of GGYSLAH (SEQ ID NO: 123), light chain variable region (VL) CDR1 sequence of RASENIRSNLA (SEQ ID NO: 28), VL CDR2 sequence of VATNLAD (SEQ ID NO: 29), and VL CDR3 sequence of QHYWGTTWT (SEQ ID NO: 30).

18. The process of claim 17, wherein the maytansinoid is DM1.

19. The process of claim 17, wherein the bifunctional crosslinking reagent is SMCC and the maytansinoid is DM1.

20. The process of claim 1, wherein the antibody comprises a VH sequence of SEQ ID NO: 57 or 58 and a VL sequence of SEQ ID NO: 74.

21. The process of claim 20, wherein the maytansinoid is DM1.

22. The process of claim 20, wherein the bifunctional crosslinking reagent is SMCC and the maytansinoid is DM1.

* * * * *

SEQUENCE LISTING

```
<160> NUMBER OF SEQ ID NOS: 127

<210> SEQ ID NO 1
<211> LENGTH: 5
<212> TYPE: PRT
<213> ORGANISM: Artificial Sequence
<220> FEATURE:
<223> OTHER INFORMATION: Heavy Chain CDR1

<400> SEQUENCE: 1

Gly Tyr Phe Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Heavy Chain CDR2
<220> FEATURE:
<221> NAME/KEY: MISC_FEATURE
<222> LOCATION: (14)..(14)
<223> OTHER INFORMATION: Xaa is Lys, Gln, His, or Arg
<220> FEATURE:
<221> NAME/KEY: MISC_FEATURE
<222> LOCATION: (16)..(16)
<223> OTHER INFORMATION: Xaa is Gln, His, Asn, or Arg
<220> FEATURE:
<221> NAME/KEY: MISC_FEATURE
<222> LOCATION: (17)..(17)
<223> OTHER INFORMATION: Xaa is Gly, Glu, Thr, Ser, Ala, or Val

<400> SEQUENCE: 2

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial Sequence
<220> FEATURE:
<223> OTHER INFORMATION: Heavy Chain CDR3

<400> SEQUENCE: 3

Tyr Asp Gly Ser Arg Ala Met Asp Tyr
1               5

<210> SEQ ID NO 4
```

-continued

<210> SEQ ID NO 4
<211> LENGTH: 15
<212> TYPE: PRT
<213> ORGANISM: Artificial Sequence
<220> FEATURE:
<223> OTHER INFORMATION: Light Chain CDR1

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 6

Gln Gln Ser Arg Glu Tyr Pro Tyr Thr
1               5

<210> SEQ ID NO 7
<211> LENGTH: 17
<212> TYPE: PRT
<213> ORGANISM: Artificial Sequence
<220> FEATURE:
<223> OTHER INFORMATION: Heavy Chain CDR2

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 448
<212> TYPE: PRT
<213> ORGANISM: Artificial Sequence
<220> FEATURE:
<223> OTHER INFORMATION: Heavy Chain

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

```
Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 9
<211> LENGTH: 117
<212> TYPE: PRT
<213> ORGANISM: Artificial Sequence
<220> FEATURE:
<223> OTHER INFORMATION: Heavy Chain Variable Domain

<400> SEQUENCE: 9

Gln Val Gln Leu Val Gln Ser Gly Ala Glu Val Val Lys Pro Gly Ala
1               5                   10                  15
```

Ser Val Lys Ile Ser Lys Ala Ser Gly Tyr Thr Phe Thr Gly Tyr Phe
           20                  25                  30

Met Asn Trp Val Lys Gln Ser Pro Gly Gln Ser Leu Glu Trp Ile Gly
           35                  40                  45

Arg Ile His Pro Tyr Asp Gly Asp Thr Phe Tyr Asn Gln Lys Phe Gln
 50                  55                  60

Gly Lys Ala Thr Leu Thr Val Asp Lys Ser Ser Asn Thr Ala His Met
 65                  70                  75                  80

Glu Leu Leu Ser Leu Thr Ser Glu Asp Phe Ala Val Tyr Tyr Cys Thr
               85                  90                  95

Arg Tyr Asp Gly Ser Arg Ala Met Asp Tyr Trp Gly Gln Gly Thr Thr
           100                 105                 110

Val Thr Val Ser Ser
           115

<210> SEQ ID NO 10
<211> LENGTH: 112
<212> TYPE: PRT
<213> ORGANISM: Artificial Sequence
<220> FEATURE:
<223> OTHER INFORMATION: Light Chain Variable Domain

<400> SEQUENCE: 10

Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
           20                  25                  30

Gly Thr Ser Leu Met His Trp Tyr His Gln Lys Pro Gly Gln Gln Pro
           35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Asn Ile Ser
 65                  70                  75                  80

Pro Val Glu Ala Glu Asp Ala Ala Thr Tyr Tyr Cys Gln Gln Ser Arg
               85                  90                  95

Glu Tyr Pro Tyr Thr Phe Gly Gly Gly Thr Lys Leu Glu Ile Lys Arg
           100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Light Chain Variable Domain

<400> SEQUENCE: 11

Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
           20                  25                  30

Gly Thr Ser Leu Met His Trp Tyr His Gln Lys Pro Gly Gln Gln Pro
           35                  40                  45

Arg Leu Leu Ile Tyr Arg Ala Ser Asn Leu Glu Ala Gly Val Pro Asp
 50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg 85                  90                  95
Glu Tyr Pro Tyr Thr Phe Gly Gly Gly Thr Lys Leu Glu Ile Lys Arg
            100                 105                 110

<210> SEQ ID NO 12
<211> LENGTH: 11
<212> TYPE: PRT
<213> ORGANISM: Artificial Sequence
<220> FEATURE:
<223> OTHER INFORMATION: Variable heavy chain CDR amino acid sequence;
      Antibody CD37-38, VH-CDR3

<400> SEQUENCE: 12

Gly Tyr Tyr Gly Tyr Gly Ala Trp Phe Val Tyr
1               5                   10

<210> SEQ ID NO 13
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Antibody CD37-50, VH-CDR1

<400> SEQUENCE: 13

Ser Gly Phe Ala Trp His
1               5

<210> SEQ ID NO 14
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Antibody CD37-50, VH-CDR2

<400> SEQUENCE: 14

Tyr Ile Leu Tyr Ser Gly Ser Thr Val
1               5

<210> SEQ ID NO 15
<211> LENGTH: 11
<212> TYPE: PRT
<213> ORGANISM: Artificial Sequence
<220> FEATURE:
<223> OTHER INFORMATION: Variable heavy chain CDR amino acid sequence;
      Antibody CD37-50, VH-CDR3

<400> SEQUENCE: 15

Gly Tyr Tyr Gly Tyr Gly Ala Trp Phe Ala Tyr
1               5                   10

<210> SEQ ID NO 16
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Antibody CD37-51, VH-CDR1

<400> SEQUENCE: 16

Ser Gly Phe Ala Trp His
1               5

<210> SEQ ID NO 17
<211> LENGTH: 9
<212> TYPE: PRT

```
<213> ORGANISM: Artificial Sequence
<220> FEATURE:
<223> OTHER INFORMATION: Variable heavy chain CDR amino acid sequence;
      Antibody CD37-51, VH-CDR2

<400> SEQUENCE: 17

Tyr Ile His Tyr Ser Gly Ser Thr Asn
1               5

<210> SEQ ID NO 18
<211> LENGTH: 11
<212> TYPE: PRT
<213> ORGANISM: Artificial Sequence
<220> FEATURE:
<223> OTHER INFORMATION: Variable heavy chain CDR amino acid sequence;
      Antibody CD37-51, VH-CDR3

<400> SEQUENCE: 18

Gly Tyr Tyr Gly Phe Gly Ala Trp Phe Val Tyr
1               5                   10

<210> SEQ ID NO 19
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Antibody CD37-56, VH-CDR1

<400> SEQUENCE: 19

Ser Gly Phe Ala Trp His
1               5

<210> SEQ ID NO 20
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Antibody CD37-56, VH-CDR2

<400> SEQUENCE: 20

Tyr Ile His Tyr Ser Gly Gly Thr Asn
1               5

<210> SEQ ID NO 21
<211> LENGTH: 11
<212> TYPE: PRT
<213> ORGANISM: Artificial Sequence
<220> FEATURE:
<223> OTHER INFORMATION: Variable heavy chain CDR amino acid sequence;
      Antibody CD37-56, VH-CDR3

<400> SEQUENCE: 21

Gly Tyr Tyr Gly Phe Gly Ala Trp Phe Ala Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Antibody CD37-57, VH-CDR1

<400> SEQUENCE: 22

Ser Gly Phe Ala Trp His
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Antibody CD37-57, VH-CDR2

<400> SEQUENCE: 23

Tyr Ile Leu Tyr Ser Gly Ser Thr Val
1               5

<210> SEQ ID NO 24
<211> LENGTH: 11
<212> TYPE: PRT
<213> ORGANISM: Artificial Sequence
<220> FEATURE:
<223> OTHER INFORMATION: Variable heavy chain CDR amino acid sequence;
      Antibody CD37-57, VH-CDR3

<400> SEQUENCE: 24

Gly Tyr Tyr Gly Tyr Gly Ala Trp Phe Ala Tyr
1               5                   10

<210> SEQ ID NO 25
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Consensus, VH-CDR1
<220> FEATURE:
<221> NAME/KEY: MISC_FEATURE
<222> LOCATION: (4)..(4)
<223> OTHER INFORMATION: Where Xaa is Ala or Gly

<400> SEQUENCE: 25

Ser Gly Phe Xaa Trp His
1               5

<210> SEQ ID NO 26
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Consensus, VH-CDR2
<220> FEATURE:
<221> NAME/KEY: MISC_FEATURE
<222> LOCATION: (3)..(3)
<223> OTHER INFORMATION: Where Xaa is Leu or His
<220> FEATURE:
<221> NAME/KEY: MISC_FEATURE
<222> LOCATION: (7)..(7)
<223> OTHER INFORMATION: Where Xaa is Gly or Ser
<220> FEATURE:
<221> NAME/KEY: MISC_FEATURE
<222> LOCATION: (9)..(9)
<223> OTHER INFORMATION: Where Xaa is Asp, Val or Asn

<400> SEQUENCE: 26

Tyr Ile Xaa Tyr Ser Gly Xaa Thr Xaa
1               5

<210> SEQ ID NO 27
<211> LENGTH: 11
<212> TYPE: PRT
<213> ORGANISM: Artificial Sequence
<220> FEATURE:
```

```
<223> OTHER INFORMATION: Variable heavy chain CDR amino acid sequence;
      Consensus, VH-CDR3
<220> FEATURE:
<221> NAME/KEY: MISC_FEATURE
<222> LOCATION: (5)..(5)
<223> OTHER INFORMATION: Where Xaa is Tyr or Phe
<220> FEATURE:
<221> NAME/KEY: MISC_FEATURE
<222> LOCATION: (10)..(10)
<223> OTHER INFORMATION: Where Xaa is Val or Ala

<400> SEQUENCE: 27

Gly Tyr Tyr Gly Xaa Gly Ala Trp Phe Xaa Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Variable light chain CDR amino acid sequence;
      CD37-3, VL-CDR1

<400> SEQUENCE: 28

Arg Ala Ser Glu Asn Ile Arg Ser Asn Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-3, VL-CDR2

<400> SEQUENCE: 29

Val Ala Thr Asn Leu Ala Asp
1               5

<210> SEQ ID NO 30
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-3, VL-CDR3

<400> SEQUENCE: 30

Gln His Tyr Trp Gly Thr Thr Trp Thr
1               5

<210> SEQ ID NO 31
<211> LENGTH: 15
<212> TYPE: PRT
<213> ORGANISM: Artificial Sequence
<220> FEATURE:
<223> OTHER INFORMATION: Variable light chain CDR amino acid sequence;
      CD37-12, VL-CDR1

<400> SEQUENCE: 31

Arg Ala Ser Gln Ser Val Ser Thr Ser Ser Tyr Ser Tyr Leu Tyr
1               5                   10                  15

<210> SEQ ID NO 32
<211> LENGTH: 7
<212> TYPE: PRT
<213> ORGANISM: Artificial Sequence
<220> FEATURE:
<223> OTHER INFORMATION: Variable light chain CDR amino acid sequence;
```

CD37-12, VL-CDR2

<400> SEQUENCE: 32

Tyr Ala Ser Asn Leu Ala Ser
1               5

<210> SEQ ID NO 33
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-12, VL-CDR3

<400> SEQUENCE: 33

Gln His Ser Trp Glu Ile Pro Tyr Thr
1               5

<210> SEQ ID NO 34
<211> LENGTH: 10
<212> TYPE: PRT
<213> ORGANISM: Artificial Sequence
<220> FEATURE:
<223> OTHER INFORMATION: Variable light chain CDR amino acid sequence;
      CD37-38, VL-CDR1

<400> SEQUENCE: 34

Ser Ala Ser Ser Ser Val Thr Tyr Met His
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-38, VL-CDR2

<400> SEQUENCE: 35

Asp Thr Ser Lys Leu Ala Ser
1               5

<210> SEQ ID NO 36
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-38, VL-CDR3

<400> SEQUENCE: 36

Gln Gln Trp Ile Ser Asn Pro Pro Thr
1               5

<210> SEQ ID NO 37
<211> LENGTH: 10
<212> TYPE: PRT
<213> ORGANISM: Artificial Sequence
<220> FEATURE:
<223> OTHER INFORMATION: Variable light chain CDR amino acid sequence;
      CD37-50, VL-CDR1

<400> SEQUENCE: 37

Ser Ala Thr Ser Ser Val Thr Tyr Met His
1               5                   10

<210> SEQ ID NO 38

```
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-50, VL-CDR2

<400> SEQUENCE: 38

Asp Thr Ser Lys Leu Pro Tyr
1               5

<210> SEQ ID NO 39
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-50, VL-CDR3

<400> SEQUENCE: 39

Gln Gln Trp Ser Asp Asn Pro Pro Thr
1               5

<210> SEQ ID NO 40
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-50, VL-CDR2,
      Humanized

<400> SEQUENCE: 40

Asp Thr Ser Asn Leu Pro Tyr
1               5

<210> SEQ ID NO 41
<211> LENGTH: 10
<212> TYPE: PRT
<213> ORGANISM: Artificial Sequence
<220> FEATURE:
<223> OTHER INFORMATION: Variable light chain CDR amino
      acid sequence; CD37-51, VL-CDR1

<400> SEQUENCE: 41

Ser Ala Thr Ser Ser Val Thr Tyr Met His
1               5                   10

<210> SEQ ID NO 42
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-51, VL-CDR2

<400> SEQUENCE: 42

Asp Thr Ser Lys Leu Ala Ser
1               5

<210> SEQ ID NO 43
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-51, VL-CDR3

<400> SEQUENCE: 43
```

Gln Gln Trp Ser Ser Asn Pro Pro Thr
1               5

<210> SEQ ID NO 44
<211> LENGTH: 10
<212> TYPE: PRT
<213> ORGANISM: Artificial Sequence
<220> FEATURE:
<223> OTHER INFORMATION: Variable light chain CDR amino acid sequence;
      CD37-56, VL-CDR1

<400> SEQUENCE: 44

Ser Ala Ser Ser Ser Val Thr Tyr Met His
1               5                   10

<210> SEQ ID NO 45
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-56, VL-CDR2

<400> SEQUENCE: 45

Asp Thr Ser Lys Leu Ala Ser
1               5

<210> SEQ ID NO 46
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-56, VL-CDR3

<400> SEQUENCE: 46

Gln Gln Trp Ile Ser Asp Pro Pro Thr
1               5

<210> SEQ ID NO 47
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-56, VL-CDR2,
      Humanized

<400> SEQUENCE: 47

Asp Thr Ser Asn Leu Ala Ser
1               5

<210> SEQ ID NO 48
<211> LENGTH: 10
<212> TYPE: PRT
<213> ORGANISM: Artificial Sequence
<220> FEATURE:
<223> OTHER INFORMATION: Variable light chain CDR amino
      acid sequence; CD37-57, VL-CDR1

<400> SEQUENCE: 48

Ser Ala Thr Ser Ser Val Thr Tyr Met His
1               5                   10

<210> SEQ ID NO 49
<211> LENGTH: 7
<212> TYPE: PRT

```
<213> ORGANISM: Artificial Sequence
<220> FEATURE:
<223> OTHER INFORMATION: Variable light chain CDR amino acid sequence;
      CD37-57, VL-CDR2

<400> SEQUENCE: 49

Asp Thr Ser Lys Leu Ala Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Variable light chain CDR amino acid sequence;
      CD37-57, VL-CDR3

<400> SEQUENCE: 50

Gln Gln Trp Ser Asp Asn Pro Pro Thr
1               5

<210> SEQ ID NO 51
<211> LENGTH: 7
<212> TYPE: PRT
<213> ORGANISM: Artificial Sequence
<220> FEATURE:
<223> OTHER INFORMATION: Variable light chain CDR amino acid sequence;
      CD37-57, VL-CDR2,
      Humanized

<400> SEQUENCE: 51

Asp Thr Ser Asn Leu Ala Ser
1               5

<210> SEQ ID NO 52
<211> LENGTH: 10
<212> TYPE: PRT
<213> ORGANISM: Artificial Sequence
<220> FEATURE:
<223> OTHER INFORMATION: Variable light chain CDR amino acid sequence;
      Consensus, VL-CDR1
<220> FEATURE:
<221> NAME/KEY: MISC_FEATURE
<222> LOCATION: (3)..(3)
<223> OTHER INFORMATION: Where Xaa is Thr or Ser

<400> SEQUENCE: 52

Ser Ala Xaa Ser Ser Val Thr Tyr Met His
1               5                   10

<210> SEQ ID NO 53
<211> LENGTH: 7
<212> TYPE: PRT
<213> ORGANISM: Artificial Sequence
<220> FEATURE:
<223> OTHER INFORMATION: Variable light chain CDR amino acid sequence;
      Consensus, VL-CDR2
<220> FEATURE:
<221> NAME/KEY: MISC_FEATURE
<222> LOCATION: (4)..(4)
<223> OTHER INFORMATION: Where Xaa is Lys or Asn
<220> FEATURE:
<221> NAME/KEY: MISC_FEATURE
<222> LOCATION: (6)..(6)
<223> OTHER INFORMATION: Where Xaa is Ala or Pro
<220> FEATURE:
<221> NAME/KEY: MISC_FEATURE
<222> LOCATION: (7)..(7)
<223> OTHER INFORMATION: Where Xaa is Ser or Tyr

<400> SEQUENCE: 53
```

```
Asp Thr Ser Xaa Leu Xaa Xaa
1               5
```

<210> SEQ ID NO 54
<211> LENGTH: 9
<212> TYPE: PRT
<213> ORGANISM: Artificial Sequence
<220> FEATURE:
<223> OTHER INFORMATION: Variable light chain CDR amino acid sequence;
      Consensus, VL-CDR3
<220> FEATURE:
<221> NAME/KEY: MISC_FEATURE
<222> LOCATION: (4)..(4)
<223> OTHER INFORMATION: Where Xaa is Ile or Ser
<220> FEATURE:
<221> NAME/KEY: MISC_FEATURE
<222> LOCATION: (5)..(5)
<223> OTHER INFORMATION: Where Xaa is Ser or Asp
<220> FEATURE:
<221> NAME/KEY: MISC_FEATURE
<222> LOCATION: (6)..(6)
<223> OTHER INFORMATION: Where Xaa is Asn or Asp

<400> SEQUENCE: 54

```
Gln Gln Trp Xaa Xaa Xaa Pro Pro Thr
1               5
```

<210> SEQ ID NO 55
<211> LENGTH: 115
<212> TYPE: PRT
<213> ORGANISM: Artificial Sequence
<220> FEATURE:
<223> OTHER INFORMATION: Variable heavy chain amino acid sequences;
      muCD37-3 antibody

<400> SEQUENCE: 55

```
Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115
```

<210> SEQ ID NO 56
<211> LENGTH: 115
<212> TYPE: PRT
<213> ORGANISM: Artificial Sequence
<220> FEATURE:
<223> OTHER INFORMATION: Variable heavy chain amino acid sequences;
      chCD37-3 antibody

<400> SEQUENCE: 56

```
Gln Val Gln Val Lys Glu Ser Gly Pro Gly Leu Val Ala Pro Ser Gln
1               5                   10                  15
```

```
Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala
        115

<210> SEQ ID NO 57
<211> LENGTH: 115
<212> TYPE: PRT
<213> ORGANISM: Artificial Sequence
<220> FEATURE:
<223> OTHER INFORMATION: Variable heavy chain amino acid sequences;
      huCD37-3v1.0 antibody

<400> SEQUENCE: 57

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Pro Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser
        115

<210> SEQ ID NO 58
<211> LENGTH: 115
<212> TYPE: PRT
<213> ORGANISM: Artificial Sequence
<220> FEATURE:
<223> OTHER INFORMATION: Variable heavy chain amino acid sequences;
      huCD37-3v1.1 antibody

<400> SEQUENCE: 58

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60
```

-continued

```
Ser Arg Leu Ser Ile Lys Lys Asp His Ser Lys Ser Gln Val Phe Leu
 65                  70                  75                  80

Lys Leu Asn Ser Leu Thr Ala Ala Asp Thr Ala Thr Tyr Tyr Cys Ala
                 85                  90                  95

Lys Gly Gly Tyr Ser Leu Ala His Trp Gly Gln Gly Thr Leu Val Thr
            100                 105                 110

Val Ser Ser
        115

<210> SEQ ID NO 59
<211> LENGTH: 115
<212> TYPE: PRT
<213> ORGANISM: Artificial Sequence
<220> FEATURE:
<223> OTHER INFORMATION: Variable heavy chain amino acid sequences;
      muCD37-12 antibody

<400> SEQUENCE: 59

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
         35                 40                  45

Gly Trp Ile Asn Thr Asn Thr Gly Glu Ser Arg Asn Ala Glu Glu Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Tyr Glu Asp Thr Ala Thr Tyr Phe Cys
                 85                  90                  95

Gly Arg Gly Thr Val Val Ala Asp Trp Gly Gln Gly Thr Thr Leu Thr
            100                 105                 110

Val Ser Ser
        115

<210> SEQ ID NO 60
<211> LENGTH: 115
<212> TYPE: PRT
<213> ORGANISM: Artificial Sequence
<220> FEATURE:
<223> OTHER INFORMATION: Variable heavy chain amino acid sequences;
      chCD37-12 antibody

<400> SEQUENCE: 60

Gln Ile Gln Leu Val Gln Ser Gly Pro Glu Leu Lys Lys Pro Gly Glu
 1               5                  10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
         35                 40                  45

Gly Trp Ile Asn Thr Asn Thr Gly Glu Ser Arg Asn Ala Glu Glu Phe
     50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Tyr Glu Asp Thr Ala Thr Tyr Phe Cys
                 85                  90                  95

Gly Arg Gly Thr Val Val Ala Asp Trp Gly Gln Gly Thr Thr Leu Thr
            100                 105                 110
```

Val Ser Ser
        115

<210> SEQ ID NO 61
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-38 antibody

<400> SEQUENCE: 61

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala
        115                 120

<210> SEQ ID NO 62
<211> LENGTH: 120
<212> TYPE: PRT
<213> ORGANISM: Artificial Sequence
<220> FEATURE:
<223> OTHER INFORMATION: Variable heavy chain amino acid sequences;
      chCD37-38 antibody

<400> SEQUENCE: 62

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ala
        115                 120

<210> SEQ ID NO 63
<211> LENGTH: 120
<212> TYPE: PRT
<213> ORGANISM: Artificial Sequence
<220> FEATURE:

<223> OTHER INFORMATION: Variable heavy chain amino acid sequences;
      huCD37-38 antibody

<400> SEQUENCE: 63

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Gly Trp His Trp Ile Arg Gln Phe Pro Gly Lys Gly Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Ala Ala Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ser
        115                 120

<210> SEQ ID NO 64
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-50 antibody

<400> SEQUENCE: 64

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120

<210> SEQ ID NO 65
<211> LENGTH: 120
<212> TYPE: PRT
<213> ORGANISM: Artificial Sequence
<220> FEATURE:
<223> OTHER INFORMATION: Variable heavy chain amino acid sequences;
      huCD37-50 antibody

<400> SEQUENCE: 65

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly

```
                    20                  25                  30

Phe Ala Trp His Trp Ile Arg Gln His Pro Gly Asn Lys Leu Glu Trp
            35                  40                  45

Met Gly Tyr Ile Leu Tyr Ser Gly Ser Thr Val Tyr Ser Pro Ser Leu
        50                  55                  60

Lys Ser Arg Ile Ser Ile Thr Arg Asp Thr Ser Lys Asn His Phe Phe
 65                  70                  75                  80

Leu Gln Leu Asn Ser Val Thr Ala Ala Asp Thr Ala Thr Tyr Tyr Cys
                    85                  90                  95

Ala Arg Gly Tyr Tyr Gly Tyr Gly Ala Trp Phe Ala Tyr Trp Gly Gln
                100                 105                 110

Gly Thr Leu Val Thr Val Ser Ala
            115                 120

<210> SEQ ID NO 66
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-51 antibody

<400> SEQUENCE: 66

Asp Val Gln Leu Gln Glu Ser Gly Pro Asp Leu Leu Lys Pro Ser Gln
 1               5                  10                  15

Ser Leu Ser Leu Thr Cys Thr Val Thr Gly Tyr Ser Ile Ser Ser Gly
                    20                  25                  30

Phe Ala Trp His Trp Ile Arg Gln Phe Pro Gly Asn Lys Leu Glu Trp
            35                  40                  45

Met Gly Tyr Ile His Tyr Ser Gly Ser Thr Asn Tyr Ser Pro Ser Leu
        50                  55                  60

Lys Ser Arg Ile Ser Ile Thr Arg Asp Ser Ser Lys Asn Gln Phe Phe
 65                  70                  75                  80

Leu Gln Leu Asn Ser Val Thr Thr Glu Asp Thr Ala Thr Tyr Tyr Cys
                    85                  90                  95

Ala Arg Gly Tyr Tyr Gly Phe Gly Ala Trp Phe Val Tyr Trp Gly Gln
                100                 105                 110

Gly Thr Leu Val Thr Val Ser Ala
            115                 120

<210> SEQ ID NO 67
<211> LENGTH: 120
<212> TYPE: PRT
<213> ORGANISM: Artificial Sequence
<220> FEATURE:
<223> OTHER INFORMATION: Variable heavy chain amino acid sequences;
      huCD37-51 antibody

<400> SEQUENCE: 67

Glu Val Gln Leu Val Glu Ser Gly Pro Glu Val Leu Lys Pro Gly Glu
 1               5                  10                  15

Ser Leu Ser Leu Thr Cys Thr Val Ser Gly Tyr Ser Ile Ser Ser Gly
                    20                  25                  30

Phe Ala Trp His Trp Ile Arg Gln Phe Pro Gly Lys Gly Leu Glu Trp
            35                  40                  45

Met Gly Tyr Ile His Tyr Ser Gly Ser Thr Asn Tyr Ser Pro Ser Leu
        50                  55                  60

Gln Gly Arg Ile Ser Ile Thr Arg Asp Ser Ser Ile Asn Gln Phe Phe
```

```
                65                  70                  75                  80
Leu Gln Leu Asn Ser Val Thr Ala Ser Asp Thr Ala Thr Tyr Tyr Cys
                        85                  90                  95

Ala Arg Gly Tyr Tyr Gly Phe Gly Ala Trp Phe Val Tyr Trp Gly Gln
                    100                 105                 110

Gly Thr Leu Val Thr Val Ser Ala
            115                 120
```

<210> SEQ ID NO 68
<211> LENGTH: 120
<212> TYPE: PRT
<213> ORGANISM: Artificial Sequence
<220> FEATURE:
<223> OTHER INFORMATION: Variable heavy chain amino acid sequences;
    muCD37-56 antibody

<400> SEQUENCE: 68

```
Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
                20                  25                  30

Phe Ala Trp His Trp Ile Arg Gln Phe Pro Gly Asn Lys Leu Glu Trp
            35                  40                  45

Met Gly Tyr Ile His Tyr Ser Gly Gly Thr Asn Tyr Asn Pro Ser Leu
        50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                        85                  90                  95

Ala Arg Gly Tyr Tyr Gly Phe Gly Ala Trp Phe Ala Tyr Trp Gly Gln
                    100                 105                 110

Gly Thr Leu Val Pro Val Ser Ala
            115                 120
```

<210> SEQ ID NO 69
<211> LENGTH: 120
<212> TYPE: PRT
<213> ORGANISM: Artificial Sequence
<220> FEATURE:
<223> OTHER INFORMATION: Variable heavy chain amino acid sequences;
    huCD37-56 antibody

<400> SEQUENCE: 69

```
Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
                20                  25                  30

Phe Ala Trp His Trp Ile Arg Gln Phe Pro Gly Lys Gly Leu Glu Trp
            35                  40                  45

Met Gly Tyr Ile His Tyr Ser Gly Gly Thr Asn Tyr Asn Pro Ser Leu
        50                  55                  60

Lys Ser Arg Val Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                        85                  90                  95

Ala Arg Gly Tyr Tyr Gly Phe Gly Ala Trp Phe Ala Tyr Trp Gly Gln
                    100                 105                 110

Gly Thr Leu Val Pro Val Ser Ala
```

```
                115                 120

<210> SEQ ID NO 70
<211> LENGTH: 120
<212> TYPE: PRT
<213> ORGANISM: Artificial Sequence
<220> FEATURE:
<223> OTHER INFORMATION: Variable heavy chain amino acid sequences;
      muCD37-57 antibody

<400> SEQUENCE: 70

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120

<210> SEQ ID NO 71
<211> LENGTH: 120
<212> TYPE: PRT
<213> ORGANISM: Artificial Sequence
<220> FEATURE:
<223> OTHER INFORMATION: Variable heavy chain amino acid sequences;
      huCD37-57 antibody

<400> SEQUENCE: 71

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala
        115                 120

<210> SEQ ID NO 72
<211> LENGTH: 108
<212> TYPE: PRT
<213> ORGANISM: Artificial Sequence
<220> FEATURE:
<223> OTHER INFORMATION: Variable light chain amino acid sequences;
``` muCD37-3 antibody

<400> SEQUENCE: 72

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg
            100                 105

<210> SEQ ID NO 73
<211> LENGTH: 108
<212> TYPE: PRT
<213> ORGANISM: Artificial Sequence
<220> FEATURE:
<223> OTHER INFORMATION: Variable light chain amino acid sequences;
      chCD37-3 antibody

<400> SEQUENCE: 73

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg
            100                 105

<210> SEQ ID NO 74
<211> LENGTH: 108
<212> TYPE: PRT
<213> ORGANISM: Artificial Sequence
<220> FEATURE:
<223> OTHER INFORMATION: Variable light chain amino acid sequences;
      huCD37-3v1.0 and huCD37-3v1.1 antibody

<400> SEQUENCE: 74

Asp Ile Gln Met Thr Gln Ser Pro Ser Ser Leu Ser Val Ser Val Gly
1               5                   10                  15

Glu Arg Val Thr Ile Thr Cys Arg Ala Ser Glu Asn Ile Arg Ser Asn
            20                  25                  30

Leu Ala Trp Tyr Gln Gln Lys Pro Gly Lys Ser Pro Lys Leu Leu Val
        35                  40                  45

Asn Val Ala Thr Asn Leu Ala Asp Gly Val Pro Ser Arg Phe Ser Gly
    50                  55                  60

```
Ser Gly Ser Gly Thr Asp Tyr Ser Leu Lys Ile Asn Ser Leu Gln Pro
65                  70                  75                  80

Glu Asp Phe Gly Thr Tyr Tyr Cys Gln His Tyr Trp Gly Thr Thr Trp
                85                  90                  95

Thr Phe Gly Gln Gly Thr Lys Leu Glu Ile Lys Arg
            100                 105
```

<210> SEQ ID NO 75
<211> LENGTH: 112
<212> TYPE: PRT
<213> ORGANISM: Artificial Sequence
<220> FEATURE:
<223> OTHER INFORMATION: Variable light chain amino acid sequences; muCD37-12 antibody

<400> SEQUENCE: 75

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110
```

<210> SEQ ID NO 76
<211> LENGTH: 112
<212> TYPE: PRT
<213> ORGANISM: Artificial Sequence
<220> FEATURE:
<223> OTHER INFORMATION: Variable light chain amino acid sequences; chCD37-12 antibody

<400> SEQUENCE: 76

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110
```

<210> SEQ ID NO 77
<211> LENGTH: 107
<212> TYPE: PRT
<213> ORGANISM: Artificial Sequence

```
<220> FEATURE:
<223> OTHER INFORMATION: Variable light chain amino acid sequences;
      muCD37-38 antibody

<400> SEQUENCE: 77

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg
            100                 105

<210> SEQ ID NO 78
<211> LENGTH: 107
<212> TYPE: PRT
<213> ORGANISM: Artificial Sequence
<220> FEATURE:
<223> OTHER INFORMATION: Variable light chain amino acid sequences;
      chCD37-38 antibody

<400> SEQUENCE: 78

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg
            100                 105

<210> SEQ ID NO 79
<211> LENGTH: 107
<212> TYPE: PRT
<213> ORGANISM: Artificial Sequence
<220> FEATURE:
<223> OTHER INFORMATION: Variable light chain amino acid sequences;
      huCD37-38 antibody

<400> SEQUENCE: 79

Asp Ile Val Leu Thr Gln Ser Pro Ala Ser Met Ser Ala Ser Pro Gly
1               5                   10                  15

Glu Arg Val Thr Met Thr Cys Ser Ala Ser Ser Val Thr Tyr Met
            20                  25                  30

His Trp Tyr Gln Gln Lys Pro Gly Thr Ser Pro Lys Arg Trp Ile Tyr
        35                  40                  45
```

-continued

```
Asp Thr Ser Lys Leu Ala Ser Gly Val Pro Ala Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ile Ser Asn Pro Pro Thr
                85                  90                  95
Phe Gly Gly Gly Thr Lys Leu Glu Ile Lys Arg
            100                 105

<210> SEQ ID NO 80
<211> LENGTH: 107
<212> TYPE: PRT
<213> ORGANISM: Artificial Sequence
<220> FEATURE:
<223> OTHER INFORMATION: Variable light chain amino acid sequences;
      muCD37-50 antibody

<400> SEQUENCE: 80

Gln Ile Val Leu Thr Gln Ser Pro Ala Ile Met Ser Ala Ser Pro Gly
1               5                   10                  15
Glu Lys Val Thr Met Thr Cys Ser Ala Thr Ser Ser Val Thr Tyr Met
                20                  25                  30
His Trp Tyr Gln Gln Lys Ser Gly Thr Ser Pro Lys Arg Trp Ile Tyr
            35                  40                  45
Asp Thr Ser Lys Leu Pro Tyr Gly Val Pro Gly Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Asp Asn Pro Pro Thr
                85                  90                  95
Phe Gly Ser Gly Thr Lys Leu Glu Ile Lys Arg
            100                 105

<210> SEQ ID NO 81
<211> LENGTH: 107
<212> TYPE: PRT
<213> ORGANISM: Artificial Sequence
<220> FEATURE:
<223> OTHER INFORMATION: Variable light chain amino acid sequences;
      huCD37-50 antibody

<400> SEQUENCE: 81

Glu Ile Val Leu Thr Gln Ser Pro Ala Thr Met Ser Ala Ser Pro Gly
1               5                   10                  15
Glu Arg Val Thr Met Thr Cys Ser Ala Thr Ser Ser Val Thr Tyr Met
                20                  25                  30
His Trp Tyr Gln Gln Lys Pro Gly Gln Ser Pro Lys Arg Trp Ile Tyr
            35                  40                  45
Asp Thr Ser Asn Leu Pro Tyr Gly Val Pro Ala Arg Phe Ser Gly Ser
    50                  55                  60
Gly Ser Gly Thr Ser Tyr Ser Leu Thr Ile Ser Ser Met Glu Ala Glu
65                  70                  75                  80
Asp Ala Ala Thr Tyr Tyr Cys Gln Gln Trp Ser Asp Asn Pro Pro Thr
                85                  90                  95
Phe Gly Gln Gly Thr Lys Leu Glu Ile Lys Arg
            100                 105

<210> SEQ ID NO 82
<211> LENGTH: 107
```

```
<212> TYPE: PRT
<213> ORGANISM: Artificial Sequence
<220> FEATURE:
<223> OTHER INFORMATION: Variable light chain amino acid sequences;
      muCD37-51 antibody

<400> SEQUENCE: 82

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg
            100                 105

<210> SEQ ID NO 83
<211> LENGTH: 107
<212> TYPE: PRT
<213> ORGANISM: Artificial Sequence
<220> FEATURE:
<223> OTHER INFORMATION: Variable light chain amino acid sequences;
      huCD37-51 antibody

<400> SEQUENCE: 83

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys Arg
            100                 105

<210> SEQ ID NO 84
<211> LENGTH: 107
<212> TYPE: PRT
<213> ORGANISM: Artificial Sequence
<220> FEATURE:
<223> OTHER INFORMATION: Variable light chain amino acid sequences;
      muCD37-56 antibody

<400> SEQUENCE: 84

Gln Ile Val Leu Thr Gln Ser Pro Ala Phe Met Ser Ala Ser Pro Gly
1               5                   10                  15

Asp Lys Val Thr Met Thr Cys Ser Ala Ser Ser Val Thr Tyr Met
            20                  25                  30

His Trp Tyr Gln Gln Lys Ser Gly Thr Ser Pro Lys Arg Trp Ile Tyr
```

35                  40                  45

Asp Thr Ser Lys Leu Ala Ser Gly Val Pro Ala Arg Phe Ser Gly Gly
                50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gly Gly Thr Lys Leu Glu Ile Lys Arg
            100                 105

<210> SEQ ID NO 85
<211> LENGTH: 107
<212> TYPE: PRT
<213> ORGANISM: Artificial Sequence
<220> FEATURE:
<223> OTHER INFORMATION: Variable light chain amino acid sequences;
      huCD37-56 antibody

<400> SEQUENCE: 85

Asp Ile Val Leu Thr Gln Ser Pro Ala Phe Met Ser Ala Ser Pro Gly
1               5                   10                  15

Glu Lys Val Thr Met Thr Cys Ser Ala Ser Ser Val Thr Tyr Met
                20                  25                  30

His Trp Tyr Gln Gln Lys Pro Asp Gln Ser Pro Lys Arg Trp Ile Tyr
                35                  40                  45

Asp Thr Ser Asn Leu Ala Ser Gly Val Pro Ser Arg Phe Ser Gly Gly
                50                  55                  60

Gly Ser Gly Thr Asp Tyr Ser Leu Thr Ile Ser Ser Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gln Gly Thr Lys Leu Glu Ile Lys Arg
            100                 105

<210> SEQ ID NO 86
<211> LENGTH: 107
<212> TYPE: PRT
<213> ORGANISM: Artificial Sequence
<220> FEATURE:
<223> OTHER INFORMATION: Variable light chain amino acid sequences;
      muCD37-57 antibody

<400> SEQUENCE: 86

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
                20                  25                  30

His Trp Tyr Gln Gln Lys Ser Gly Thr Ser Pro Lys Arg Trp Ile Tyr
                35                  40                  45

Asp Thr Ser Lys Leu Ala Ser Gly Val Pro Ala Arg Phe Ser Gly Ser
                50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg
            100                 105

-continued

<210> SEQ ID NO 87
<211> LENGTH: 107
<212> TYPE: PRT
<213> ORGANISM: Artificial Sequence
<220> FEATURE:
<223> OTHER INFORMATION: Variable light chain amino acid sequences;
      huCD37-57 antibody

<400> SEQUENCE: 87

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Arg Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg
            100                 105

<210> SEQ ID NO 88
<211> LENGTH: 445
<212> TYPE: PRT
<213> ORGANISM: Artificial Sequence
<220> FEATURE:
<223> OTHER INFORMATION: Full-length heavy chain amino acid sequences;
      muCD37-3 antibody

<400> SEQUENCE: 88

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ala Ala Lys Thr Thr Ala Pro Ser Val Tyr Pro Leu Ala Pro
        115                 120                 125

Val Cys Gly Asp Thr Thr Gly Ser Ser Val Thr Leu Gly Cys Leu Val
    130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
            180                 185                 190

Gln Ser Ile Thr Cys Asn Val Ala His Pro Ala Ser Ser Thr Lys Val

```
                195                 200                 205
Asp Lys Lys Ile Glu Pro Arg Gly Pro Thr Ile Lys Pro Cys Pro Pro
210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
        275                 280                 285

Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
        355                 360                 365

Asp Phe Met Pro Glu Asp Ile Tyr Val Glu Trp Thr Asn Asn Gly Lys
    370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445

<210> SEQ ID NO 89
<211> LENGTH: 445
<212> TYPE: PRT
<213> ORGANISM: Artificial Sequence
<220> FEATURE:
<223> OTHER INFORMATION: Full-length heavy chain amino acid sequences;
      chCD37-3 antibody

<400> SEQUENCE: 89

Gln Val Gln Val Lys Glu Ser Gly Pro Gly Leu Val Ala Pro Ser Gln
1               5                   10                  15

Ser Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ala Leu Lys
    50                  55                  60

Ser Arg Leu Ser Ile Lys Lys Asp His Ser Lys Ser Gln Val Phe Leu
65                  70                  75                  80

Lys Leu Asn Ser Leu Gln Thr Asp Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110
```

```
Val Ser Ala Ala Ser Thr Lys Gly Pro Ser Val Phe Pro Leu Ala Pro
            115                 120                 125

Ser Ser Lys Ser Thr Ser Gly Gly Thr Ala Ala Leu Gly Cys Leu Val
        130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
        435                 440                 445

<210> SEQ ID NO 90
<211> LENGTH: 444
<212> TYPE: PRT
<213> ORGANISM: Artificial Sequence
<220> FEATURE:
<223> OTHER INFORMATION: Full-length heavy chain amino acid sequences;
      huCD37-3v1.0 antibody

<400> SEQUENCE: 90

Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30
```

-continued

```
Gly Val Ser Trp Val Arg Gln Pro Gly Lys Gly Leu Glu Trp Leu
         35                  40                  45
Gly Val Ile Trp Gly Asp Gly Ser Thr Asn Tyr His Pro Ser Leu Lys
 50                  55                  60
Ser Arg Leu Ser Ile Lys Lys Asp His Ser Lys Ser Gln Val Phe Leu
 65                  70                  75                  80
Lys Leu Asn Ser Leu Thr Ala Ala Asp Thr Ala Thr Tyr Tyr Cys Ala
                 85                  90                  95
Lys Gly Gly Tyr Ser Leu Ala His Trp Gly Gln Gly Thr Leu Val Thr
                100                 105                 110
Val Ser Ser Ala Ser Thr Lys Gly Pro Ser Val Phe Pro Leu Ala Pro
             115                 120                 125
Ser Ser Lys Ser Thr Ser Gly Gly Thr Ala Ala Leu Gly Cys Leu Val
         130                 135                 140
Lys Asp Tyr Phe Pro Glu Pro Val Thr Val Ser Trp Asn Ser Gly Ala
145                 150                 155                 160
Leu Thr Ser Gly Val His Thr Phe Pro Ala Val Leu Gln Ser Ser Gly
                165                 170                 175
Leu Tyr Ser Leu Ser Ser Val Val Thr Val Pro Ser Ser Ser Leu Gly
            180                 185                 190
Thr Gln Thr Tyr Ile Cys Asn Val Asn His Lys Pro Ser Asn Thr Lys
        195                 200                 205
Val Asp Lys Lys Val Glu Pro Lys Ser Cys Asp Lys Thr His Thr Cys
    210                 215                 220
Pro Pro Cys Pro Ala Pro Glu Leu Leu Gly Gly Pro Ser Val Phe Leu
225                 230                 235                 240
Phe Pro Pro Lys Pro Lys Asp Thr Leu Met Ile Ser Arg Thr Pro Glu
                245                 250                 255
Val Thr Cys Val Val Val Asp Val Ser His Glu Asp Pro Glu Val Lys
            260                 265                 270
Phe Asn Trp Tyr Val Asp Gly Val Glu Val His Asn Ala Lys Thr Lys
        275                 280                 285
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
    370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly
        435                 440
```

<210> SEQ ID NO 91
<211> LENGTH: 444
<212> TYPE: PRT
<213> ORGANISM: Artificial Sequence
<220> FEATURE:
<223> OTHER INFORMATION: Full-length heavy chain amino acid sequences; huCD37-3v1.1 antibody

<400> SEQUENCE: 91

```
Gln Val Gln Val Gln Glu Ser Gly Pro Gly Leu Val Ala Pro Ser Gln
1               5                   10                  15

Thr Leu Ser Ile Thr Cys Thr Val Ser Gly Phe Ser Leu Thr Thr Ser
            20                  25                  30

Gly Val Ser Trp Val Arg Gln Pro Pro Gly Lys Gly Leu Glu Trp Leu
        35                  40                  45

Gly Val Ile Trp Gly Asp Gly Ser Thr Asn Tyr His Ser Ser Leu Lys
    50                  55                  60

Ser Arg Leu Ser Ile Lys Lys Asp His Ser Lys Ser Gln Val Phe Leu
65                  70                  75                  80

Lys Leu Asn Ser Leu Thr Ala Ala Asp Thr Ala Thr Tyr Tyr Cys Ala
                85                  90                  95

Lys Gly Gly Tyr Ser Leu Ala His Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365
```

```
Gly Phe Tyr Pro Ser Asp Ile Ala Val Glu Trp Glu Ser Asn Gly Gln
            370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly
            435                 440

<210> SEQ ID NO 92
<211> LENGTH: 445
<212> TYPE: PRT
<213> ORGANISM: Artificial Sequence
<220> FEATURE:
<223> OTHER INFORMATION: Full-length heavy chain amino acid sequences;
      muCD37-12 antibody

<400> SEQUENCE: 92

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Gln Gly Lys Gly Leu Lys Trp Met
            35                  40                  45

Gly Trp Ile Asn Thr Asn Thr Gly Glu Ser Arg Asn Ala Glu Glu Phe
50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser Ala Lys Thr Thr Ala Pro Ser Val Tyr Pro Leu Ala Pro
            115                 120                 125

Val Cys Gly Asp Thr Thr Gly Ser Ser Val Thr Leu Gly Cys Leu Val
            130                 135                 140

Lys Gly Tyr Phe Pro Glu Pro Val Thr Leu Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Thr Ser Ser Thr Trp Pro Ser
                180                 185                 190

Gln Ser Ile Thr Cys Asn Val Ala His Pro Ala Ser Ser Thr Lys Val
            195                 200                 205

Asp Lys Lys Ile Glu Pro Arg Gly Pro Thr Ile Lys Pro Cys Pro Pro
210                 215                 220

Cys Lys Cys Pro Ala Pro Asn Leu Leu Gly Gly Pro Ser Val Phe Ile
225                 230                 235                 240

Phe Pro Pro Lys Ile Lys Asp Val Leu Met Ile Ser Leu Ser Pro Ile
                245                 250                 255

Val Thr Cys Val Val Val Asp Val Ser Glu Asp Asp Pro Asp Val Gln
            260                 265                 270

Ile Ser Trp Phe Val Asn Asn Val Glu Val His Thr Ala Gln Thr Gln
```

```
                275                 280                 285
Thr His Arg Glu Asp Tyr Asn Ser Thr Leu Arg Val Val Ser Ala Leu
    290                 295                 300

Pro Ile Gln His Gln Asp Trp Met Ser Gly Lys Glu Phe Lys Cys Lys
305                 310                 315                 320

Val Asn Asn Lys Asp Leu Pro Ala Pro Ile Glu Arg Thr Ile Ser Lys
                325                 330                 335

Pro Lys Gly Ser Val Arg Ala Pro Gln Val Tyr Val Leu Pro Pro Pro
            340                 345                 350

Glu Glu Glu Met Thr Lys Lys Gln Val Thr Leu Thr Cys Met Val Thr
        355                 360                 365

Asp Phe Met Pro Glu Asp Ile Tyr Val Glu Trp Thr Asn Asn Gly Lys
    370                 375                 380

Thr Glu Leu Asn Tyr Lys Asn Thr Glu Pro Val Leu Asp Ser Asp Gly
385                 390                 395                 400

Ser Tyr Phe Met Tyr Ser Lys Leu Arg Val Glu Lys Lys Asn Trp Val
                405                 410                 415

Glu Arg Asn Ser Tyr Ser Cys Ser Val Val His Glu Gly Leu His Asn
            420                 425                 430

His His Thr Thr Lys Ser Phe Ser Arg Thr Pro Gly Lys
        435                 440                 445

<210> SEQ ID NO 93
<211> LENGTH: 445
<212> TYPE: PRT
<213> ORGANISM: Artificial Sequence
<220> FEATURE:
<223> OTHER INFORMATION: Full-length heavy chain amino acid sequences;
      chCD37-12 antibody

<400> SEQUENCE: 93

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
                20                  25                  30

Gly Met Asn Trp Val Lys Gln Ala Gln Gly Lys Gly Leu Lys Trp Met
            35                  40                  45

Gly Trp Ile Asn Thr Asn Thr Gly Glu Ser Arg Asn Ala Glu Glu Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Gly Arg Gly Thr Val Val Ala Asp Trp Gly Gln Gly Thr Thr Leu Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
        260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
        340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
        420                 425                 430

His Tyr Thr Gln Lys Ser Leu Ser Leu Ser Pro Gly Lys
            435                 440                 445

<210> SEQ ID NO 94
<211> LENGTH: 444
<212> TYPE: PRT
<213> ORGANISM: Artificial Sequence
<220> FEATURE:
<223> OTHER INFORMATION: Full-length heavy chain amino acid sequences;
      muCD37-38 antibody

<400> SEQUENCE: 94

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Gly Trp His Trp Ile Arg Gln Phe Pro Gly Asn Lys Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Thr Glu Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110
```

Gly Thr Leu Val Thr Val Ser Ala Ala Lys Thr Thr Pro Pro Ser Val
            115                 120                 125

Tyr Pro Leu Ala Pro Gly Ser Ala Ala Gln Thr Asn Ser Met Val Thr
        130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
370                 375                 380

Ala Glu Asn Tyr Lys Asn Thr Gln Pro Ile Met Asn Thr Asn Gly Ser
                385                 390                 395                 400

Tyr Phe Val Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
        420                 425                 430

His Thr Glu Lys Ser Leu Ser His Ser Pro Gly Lys
    435                 440

<210> SEQ ID NO 95
<211> LENGTH: 449
<212> TYPE: PRT
<213> ORGANISM: Artificial Sequence
<220> FEATURE:
<223> OTHER INFORMATION: Full-length heavy chain amino acid sequences;
      chCD37-38 antibody

<400> SEQUENCE: 95

Gln Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly

```
            20                  25                  30
Phe Gly Trp His Trp Ile Arg Gln Phe Pro Gly Asn Lys Leu Glu Trp
        35                  40                  45
Met Ala Tyr Ile Leu Tyr Ser Gly Gly Thr Asp Tyr Asn Pro Ser Leu
50                  55                  60
Lys Ser Arg Ile Ser Ile Thr Arg Asp Thr Ser Lys Asn Gln Phe Phe
65                  70                  75                  80
Leu Arg Leu Ser Ser Val Thr Thr Glu Asp Thr Ala Thr Tyr Tyr Cys
                85                  90                  95
Ala Arg Gly Tyr Tyr Gly Tyr Gly Ala Trp Phe Val Tyr Trp Gly Gln
                100                 105                 110
Gly Thr Leu Val Thr Val Ser Ala Ala Ser Thr Lys Gly Pro Ser Val
                115                 120                 125
Phe Pro Leu Ala Pro Ser Ser Lys Ser Thr Ser Gly Gly Thr Ala Ala
                130                 135                 140
Leu Gly Cys Leu Val Lys Asp Tyr Phe Pro Glu Pro Val Thr Val Ser
145                 150                 155                 160
Trp Asn Ser Gly Ala Leu Thr Ser Gly Val His Thr Phe Pro Ala Val
                165                 170                 175
Leu Gln Ser Ser Gly Leu Tyr Ser Leu Ser Ser Val Val Thr Val Pro
                180                 185                 190
Ser Ser Ser Leu Gly Thr Gln Thr Tyr Ile Cys Asn Val Asn His Lys
                195                 200                 205
Pro Ser Asn Thr Lys Val Asp Lys Lys Val Glu Pro Lys Ser Cys Asp
                210                 215                 220
Lys Thr His Thr Cys Pro Pro Cys Pro Ala Pro Glu Leu Leu Gly Gly
225                 230                 235                 240
Pro Ser Val Phe Leu Phe Pro Pro Lys Pro Lys Asp Thr Leu Met Ile
                245                 250                 255
Ser Arg Thr Pro Glu Val Thr Cys Val Val Val Asp Val Ser His Glu
                260                 265                 270
Asp Pro Glu Val Lys Phe Asn Trp Tyr Val Asp Gly Val Glu Val His
                275                 280                 285
Asn Ala Lys Thr Lys Pro Arg Glu Glu Gln Tyr Asn Ser Thr Tyr Arg
                290                 295                 300
Val Val Ser Val Leu Thr Val Leu His Gln Asp Trp Leu Asn Gly Lys
305                 310                 315                 320
Glu Tyr Lys Cys Lys Val Ser Asn Lys Ala Leu Pro Ala Pro Ile Glu
                325                 330                 335
Lys Thr Ile Ser Lys Ala Lys Gly Gln Pro Arg Glu Pro Gln Val Tyr
                340                 345                 350
Thr Leu Pro Pro Ser Arg Asp Glu Leu Thr Lys Asn Gln Val Ser Leu
                355                 360                 365
Thr Cys Leu Val Lys Gly Phe Tyr Pro Ser Asp Ile Ala Val Glu Trp
                370                 375                 380
Glu Ser Asn Gly Gln Pro Glu Asn Asn Tyr Lys Thr Thr Pro Pro Val
385                 390                 395                 400
Leu Asp Ser Asp Gly Ser Phe Phe Leu Tyr Ser Lys Leu Thr Val Asp
                405                 410                 415
Lys Ser Arg Trp Gln Gln Gly Asn Val Phe Ser Cys Ser Val Met His
                420                 425                 430
Glu Ala Leu His Asn His Tyr Thr Gln Lys Ser Leu Ser Leu Ser Pro
                435                 440                 445
```

Gly

<210> SEQ ID NO 96
<211> LENGTH: 449
<212> TYPE: PRT
<213> ORGANISM: Artificial Sequence
<220> FEATURE:
<223> OTHER INFORMATION: Full-length heavy chain amino acid sequences; huCD37-38 antibody

<400> SEQUENCE: 96

```
Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
            20                  25                  30

Phe Gly Trp His Trp Ile Arg Gln Phe Pro Gly Lys Gly Leu Glu Trp
        35                  40                  45

Met Ala Tyr Ile Leu Tyr Ser Gly Gly Thr Asp Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Arg Leu Ser Ser Val Thr Ala Ala Asp Thr Ala Thr Tyr Tyr Cys
                85                  90                  95

Ala Arg Gly Tyr Tyr Gly Tyr Gly Ala Trp Phe Val Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350
```

-continued

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly

<210> SEQ ID NO 97
<211> LENGTH: 450
<212> TYPE: PRT
<213> ORGANISM: Artificial Sequence
<220> FEATURE:
<223> OTHER INFORMATION: Full-length heavy chain amino acid sequences;
      muCD37-50 antibody

<400> SEQUENCE: 97

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Thr Glu Asp Thr Ala Thr Tyr Tyr Cys
            85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Lys Thr Thr Ala Pro Ser Val
            115                 120                 125

Tyr Pro Leu Ala Pro Val Cys Gly Asp Thr Thr Gly Ser Ser Val Thr
130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
            165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
    210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
            245                 250                 255

```
Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
    290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
    370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 98
<211> LENGTH: 449
<212> TYPE: PRT
<213> ORGANISM: Artificial Sequence
<220> FEATURE:
<223> OTHER INFORMATION: Full-length heavy chain amino acid sequences;
      huCD37-50 antibody

<400> SEQUENCE: 98

Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln His Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn His Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
```

```
                145                 150                 155                 160
Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445
Gly

<210> SEQ ID NO 99
<211> LENGTH: 450
<212> TYPE: PRT
<213> ORGANISM: Artificial Sequence
<220> FEATURE:
<223> OTHER INFORMATION: Full-length heavy chain amino acid sequences;
      muCD37-51 antibody

<400> SEQUENCE: 99

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Ser Ser Gly
            20                  25                  30

Phe Ala Trp His Trp Ile Arg Gln Phe Pro Gly Asn Lys Leu Glu Trp
            35                  40                  45

Met Gly Tyr Ile His Tyr Ser Gly Ser Thr Asn Tyr Ser Pro Ser Leu
```

```
                50                  55                  60
Lys Ser Arg Ile Ser Ile Thr Arg Asp Ser Ser Lys Asn Gln Phe Phe
 65                  70                  75                  80

Leu Gln Leu Asn Ser Val Thr Glu Asp Thr Ala Thr Tyr Tyr Cys
                 85                  90                  95

Ala Arg Gly Tyr Tyr Gly Phe Gly Ala Trp Phe Val Tyr Trp Gly Gln
                100                 105                 110

Gly Thr Leu Val Thr Val Ser Ala Ala Lys Thr Thr Ala Pro Ser Val
                115                 120                 125

Tyr Pro Leu Ala Pro Val Cys Gly Asp Thr Thr Gly Ser Ser Val Thr
                130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
                180                 185                 190

Ser Thr Trp Pro Ser Gln Ser Ile Thr Cys Asn Val Ala His Pro Ala
                195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
                260                 265                 270

Asp Pro Asp Val Gln Ile Ser Trp Phe Val Asn Asn Val Glu Val His
                275                 280                 285

Thr Ala Gln Thr Gln Thr His Arg Glu Asp Tyr Asn Ser Thr Leu Arg
                290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
                340                 345                 350

Val Leu Pro Pro Pro Glu Glu Glu Met Thr Lys Lys Gln Val Thr Leu
                355                 360                 365

Thr Cys Met Val Thr Asp Phe Met Pro Glu Asp Ile Tyr Val Glu Trp
                370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
                420                 425                 430

Glu Gly Leu His Asn His His Thr Thr Lys Ser Phe Ser Arg Thr Pro
                435                 440                 445

Gly Lys
450

<210> SEQ ID NO 100
```

-continued

```
<211> LENGTH: 449
<212> TYPE: PRT
<213> ORGANISM: Artificial Sequence
<220> FEATURE:
<223> OTHER INFORMATION: Full-length heavy chain amino acid sequences;
      huCD37-51 antibody

<400> SEQUENCE: 100
```

| | | | | | | | | | | | | | | |
|---|---|---|---|---|---|---|---|---|---|---|---|---|---|---|
| Glu | Val | Gln | Leu | Val | Glu | Ser | Gly | Pro | Glu | Val | Lys | Pro | Gly | Glu |
| 1 | | | | 5 | | | | | 10 | | | | | 15 |
| Ser | Leu | Ser | Leu | Thr | Cys | Thr | Val | Ser | Gly | Tyr | Ser | Ile | Ser | Gly |
| | | | 20 | | | | | 25 | | | | | 30 | |
| Phe | Ala | Trp | His | Trp | Ile | Arg | Gln | Phe | Pro | Gly | Lys | Gly | Leu | Glu | Trp |
| | | | 35 | | | | | 40 | | | | | 45 | |
| Met | Gly | Tyr | Ile | His | Tyr | Ser | Gly | Ser | Thr | Asn | Tyr | Ser | Pro | Ser | Leu |
| | 50 | | | | | 55 | | | | | 60 | | | | |
| Gln | Gly | Arg | Ile | Ser | Ile | Thr | Arg | Asp | Ser | Ser | Ile | Asn | Gln | Phe | Phe |
| 65 | | | | | 70 | | | | | 75 | | | | | 80 |
| Leu | Gln | Leu | Asn | Ser | Val | Thr | Ala | Ser | Asp | Thr | Ala | Thr | Tyr | Tyr | Cys |
| | | | | 85 | | | | | 90 | | | | | 95 | |
| Ala | Arg | Gly | Tyr | Tyr | Gly | Phe | Gly | Ala | Trp | Phe | Val | Tyr | Trp | Gly | Gln |
| | | | | 100 | | | | | 105 | | | | | 110 | |
| Gly | Thr | Leu | Val | Thr | Val | Ser | Ala | Ala | Ser | Thr | Lys | Gly | Pro | Ser | Val |
| | | | 115 | | | | | 120 | | | | | 125 | | |
| Phe | Pro | Leu | Ala | Pro | Ser | Ser | Lys | Ser | Thr | Ser | Gly | Gly | Thr | Ala | Ala |
| | | | 130 | | | | | 135 | | | | | 140 | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | | 180 | | | | | 185 | | | | | 190 | |
| Ser | Ser | Ser | Leu | Gly | Thr | Gln | Thr | Tyr | Ile | Cys | Asn | Val | Asn | His | Lys |
| | | | 195 | | | | | 200 | | | | | 205 | | |
| Pro | Ser | Asn | Thr | Lys | Val | Asp | Lys | Lys | Val | Glu | Pro | Lys | Ser | Cys | Asp |
| | 210 | | | | | 215 | | | | | 220 | | | | |
| Lys | Thr | His | Thr | Cys | Pro | Pro | Cys | Pro | Ala | Pro | Glu | Leu | Leu | Gly | Gly |
| 225 | | | | | 230 | | | | | 235 | | | | | 240 |
| Pro | Ser | Val | Phe | Leu | Phe | Pro | Pro | Lys | Pro | Lys | Asp | Thr | Leu | Met | Ile |
| | | | | 245 | | | | | 250 | | | | | 255 | |
| Ser | Arg | Thr | Pro | Glu | Val | Thr | Cys | Val | Val | Val | Asp | Val | Ser | His | Glu |
| | | | 260 | | | | | 265 | | | | | 270 | | |
| Asp | Pro | Glu | Val | Lys | Phe | Asn | Trp | Tyr | Val | Asp | Gly | Val | Glu | Val | His |
| | | | 275 | | | | | 280 | | | | | 285 | | |
| Asn | Ala | Lys | Thr | Lys | Pro | Arg | Glu | Glu | Gln | Tyr | Asn | Ser | Thr | Tyr | Arg |
| | 290 | | | | | 295 | | | | | 300 | | | | |
| Val | Val | Ser | Val | Leu | Thr | Val | Leu | His | Gln | Asp | Trp | Leu | Asn | Gly | Lys |
| 305 | | | | | 310 | | | | | 315 | | | | | 320 |
| Glu | Tyr | Lys | Cys | Lys | Val | Ser | Asn | Lys | Ala | Leu | Pro | Ala | Pro | Ile | Glu |
| | | | | 325 | | | | | 330 | | | | | 335 | |
| Lys | Thr | Ile | Ser | Lys | Ala | Lys | Gly | Gln | Pro | Arg | Glu | Pro | Gln | Val | Tyr |
| | | | 340 | | | | | 345 | | | | | 350 | | |
| Thr | Leu | Pro | Pro | Ser | Arg | Asp | Glu | Leu | Thr | Lys | Asn | Gln | Val | Ser | Leu |
| | | | 355 | | | | | 360 | | | | | 365 | | |
| Thr | Cys | Leu | Val | Lys | Gly | Phe | Tyr | Pro | Ser | Asp | Ile | Ala | Val | Glu | Trp |

```
                370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 101
<211> LENGTH: 444
<212> TYPE: PRT
<213> ORGANISM: Artificial Sequence
<220> FEATURE:
<223> OTHER INFORMATION: Full-length heavy chain amino acid sequences;
      muCD37-56 antibody

<400> SEQUENCE: 101

Asp Val Gln Leu Gln Glu Ser Gly Pro Asp Leu Val Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile His Tyr Ser Gly Gly Thr Asn Tyr Asn Pro Ser Leu
    50                  55                  60

Lys Ser Arg Val Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Glu Ser Asp Leu Tyr Thr Leu Ser Ser Ser Val Thr Val Pro Ser
            180                 185                 190

Ser Met Arg Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
```

```
                275                 280                 285
Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
        340                 345                 350

Glu Gln Met Ala Lys Asp Lys Val Ser Leu Thr Cys Met Ile Thr Asp
            355                 360                 365

Phe Phe Pro Glu Asp Ile Thr Val Glu Trp Gln Trp Asn Gly Gln Pro
        370                 375                 380

Ala Glu Asn Tyr Lys Asn Thr Gln Pro Ile Met Asn Thr Asn Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
        420                 425                 430

His Thr Glu Lys Ser Leu Ser His Ser Pro Gly Lys
            435                 440

<210> SEQ ID NO 102
<211> LENGTH: 449
<212> TYPE: PRT
<213> ORGANISM: Artificial Sequence
<220> FEATURE:
<223> OTHER INFORMATION: Full-length heavy chain amino acid sequences;
      huCD37-56 antibody

<400> SEQUENCE: 102

Gln Val Gln Leu Gln Glu Ser Gly Pro Gly Leu Val Lys Pro Ser Gln
1               5                   10                  15

Ser Leu Ser Leu Thr Cys Thr Val Ser Gly Tyr Ser Ile Thr Ser Gly
                20                  25                  30

Phe Ala Trp His Trp Ile Arg Gln Phe Pro Gly Lys Gly Leu Glu Trp
            35                  40                  45

Met Gly Tyr Ile His Tyr Ser Gly Gly Thr Asn Tyr Asn Pro Ser Leu
        50                  55                  60

Lys Ser Arg Val Ser Ile Thr Arg Asp Thr Ser Lys Asn Gln Phe Phe
65                  70                  75                  80

Leu Gln Leu Asn Ser Val Thr Ala Ala Asp Thr Ala Thr Tyr Tyr Cys
                85                  90                  95

Ala Arg Gly Tyr Tyr Gly Phe Gly Ala Trp Phe Ala Tyr Trp Gly Gln
            100                 105                 110

Gly Thr Leu Val Pro Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 103
<211> LENGTH: 450
<212> TYPE: PRT
<213> ORGANISM: Artificial Sequence
<220> FEATURE:
<223> OTHER INFORMATION: Full-length heavy chain amino acid sequences;
      muCD37-57 antibody

<400> SEQUENCE: 103

Asp Val Gln Leu Gln Glu Ser Gly Pro Asp Leu Leu Lys Pro Ser Gln
1               5                   10                  15

Ser Leu Ser Leu Thr Cys Thr Val Thr Gly Tyr Ser Ile Thr Ser Gly
            20                  25                  30

Phe Ala Trp His Trp Ile Arg Gln Phe Pro Gly Asn Lys Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95
```

Ala Arg Gly Tyr Tyr Gly Tyr Ala Trp Phe Ala Tyr Trp Gly Gln
            100                 105                 110

Gly Thr Leu Val Thr Val Ser Ala Ala Lys Thr Thr Ala Pro Ser Val
        115                 120                 125

Tyr Pro Leu Ala Pro Val Cys Gly Asp Thr Thr Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Thr Ser
            180                 185                 190

Ser Thr Trp Pro Ser Gln Ser Ile Thr Cys Asn Val Ala His Pro Ala
        195                 200                 205

Ser Ser Thr Lys Val Asp Lys Lys Ile Glu Pro Arg Gly Pro Thr Ile
210                 215                 220

Lys Pro Cys Pro Pro Cys Lys Cys Pro Ala Pro Asn Leu Leu Gly Gly
225                 230                 235                 240

Pro Ser Val Phe Ile Phe Pro Pro Lys Ile Lys Asp Val Leu Met Ile
                245                 250                 255

Ser Leu Ser Pro Ile Val Thr Cys Val Val Val Asp Val Ser Glu Asp
            260                 265                 270

Asp Pro Asp Val Gln Ile Ser Trp Phe Val Asn Asn Val Glu Val His
        275                 280                 285

Thr Ala Gln Thr Gln Thr His Arg Glu Asp Tyr Asn Ser Thr Leu Arg
290                 295                 300

Val Val Ser Ala Leu Pro Ile Gln His Gln Asp Trp Met Ser Gly Lys
305                 310                 315                 320

Glu Phe Lys Cys Lys Val Asn Asn Lys Asp Leu Pro Ala Pro Ile Glu
                325                 330                 335

Arg Thr Ile Ser Lys Pro Lys Gly Ser Val Arg Ala Pro Gln Val Tyr
            340                 345                 350

Val Leu Pro Pro Pro Glu Glu Glu Met Thr Lys Lys Gln Val Thr Leu
        355                 360                 365

Thr Cys Met Val Thr Asp Phe Met Pro Glu Asp Ile Tyr Val Glu Trp
370                 375                 380

Thr Asn Asn Gly Lys Thr Glu Leu Asn Tyr Lys Asn Thr Glu Pro Val
385                 390                 395                 400

Leu Asp Ser Asp Gly Ser Tyr Phe Met Tyr Ser Lys Leu Arg Val Glu
                405                 410                 415

Lys Lys Asn Trp Val Glu Arg Asn Ser Tyr Ser Cys Ser Val Val His
            420                 425                 430

Glu Gly Leu His Asn His His Thr Thr Lys Ser Phe Ser Arg Thr Pro
        435                 440                 445

Gly Lys
    450

<210> SEQ ID NO 104
<211> LENGTH: 449
<212> TYPE: PRT
<213> ORGANISM: Artificial Sequence
<220> FEATURE:
<223> OTHER INFORMATION: Full-length heavy chain amino acid sequences;
      huCD37-57 antibody

<400> SEQUENCE: 104

```
Gln Val Gln Leu Gln Glu Ser Gly Pro Gly Leu Leu Lys Pro Ser Gln
1               5                   10                  15

Ser Leu Ser Leu Thr Cys Thr Val Ser Gly Tyr Ser Ile Thr Ser Gly
            20                  25                  30

Phe Ala Trp His Trp Ile Arg Gln Phe Pro Gly Lys Gly Leu Glu Trp
        35                  40                  45

Met Gly Tyr Ile Leu Tyr Ser Gly Ser Thr Val Tyr Ser Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Ala Ala Asp Thr Ala Tyr Tyr Tyr Cys
                85                  90                  95

Ala Arg Gly Tyr Tyr Gly Tyr Gly Ala Trp Phe Ala Tyr Trp Gly Gln
            100                 105                 110

Gly Thr Leu Val Thr Val Ser Ala Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415
```

-continued

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 105
<211> LENGTH: 214
<212> TYPE: PRT
<213> ORGANISM: Artificial Sequence
<220> FEATURE:
<223> OTHER INFORMATION: Full-length light chain amino acid sequences;
      muCD37-3 antibody

<400> SEQUENCE: 105

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
        35                  40                  45

Asn Val Ala Thr Asn Leu Ala Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Thr Tyr Tyr Cys Gln His Tyr Trp Gly Thr Thr Trp
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 106
<211> LENGTH: 214
<212> TYPE: PRT
<213> ORGANISM: Artificial Sequence
<220> FEATURE:
<223> OTHER INFORMATION: Full-length light chain amino acid sequences;
      chCD37-3 antibody

<400> SEQUENCE: 106

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Arg Ser Asn
            20                  25                  30

Leu Ala Trp Tyr Gln Gln Lys Gln Gly Lys Ser Pro Gln Leu Leu Val
```

```
            35                  40                  45
Asn Val Ala Thr Asn Leu Ala Asp Gly Val Pro Ser Arg Phe Ser Gly
         50                  55                  60

Ser Gly Ser Gly Thr Gln Tyr Ser Leu Lys Ile Asn Ser Leu Gln Ser
 65                  70                  75                  80

Glu Asp Phe Gly Thr Tyr Tyr Cys Gln His Tyr Trp Gly Thr Thr Trp
                 85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 107
<211> LENGTH: 214
<212> TYPE: PRT
<213> ORGANISM: Artificial Sequence
<220> FEATURE:
<223> OTHER INFORMATION: Full-length light chain amino acid sequences;
      huCD37-3v1.0 and huCD37-3v1.1 antibody

<400> SEQUENCE: 107

Asp Ile Gln Met Thr Gln Ser Pro Ser Ser Leu Ser Val Ser Val Gly
 1               5                  10                  15

Glu Arg Val Thr Ile Thr Cys Arg Ala Ser Glu Asn Ile Arg Ser Asn
             20                  25                  30

Leu Ala Trp Tyr Gln Gln Lys Pro Gly Lys Ser Pro Lys Leu Leu Val
         35                  40                  45

Asn Val Ala Thr Asn Leu Ala Asp Gly Val Pro Ser Arg Phe Ser Gly
     50                  55                  60

Ser Gly Ser Gly Thr Asp Tyr Ser Leu Lys Ile Asn Ser Leu Gln Pro
 65                  70                  75                  80

Glu Asp Phe Gly Thr Tyr Tyr Cys Gln His Tyr Trp Gly Thr Thr Trp
                 85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 108
<211> LENGTH: 218
<212> TYPE: PRT
<213> ORGANISM: Artificial Sequence
<220> FEATURE:
<223> OTHER INFORMATION: Full-length light chain amino acid sequences;
      muCD37-12 antibody

<400> SEQUENCE: 108

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 109
<211> LENGTH: 218
<212> TYPE: PRT
<213> ORGANISM: Artificial Sequence
<220> FEATURE:
<223> OTHER INFORMATION: Full-length light chain amino acid sequences;
      chCD37-12 antibody

<400> SEQUENCE: 109

Asp Ile Val Leu Thr Gln Ser Pro Ala Ser Leu Ala Val Ser Leu Gly
1               5                   10                  15

Gln Arg Ala Thr Ile Ser Cys Arg Ala Ser Gln Ser Val Ser Thr Ser
            20                  25                  30
```

Ser Tyr Ser Tyr Leu Tyr Trp Phe Gln Gln Lys Pro Gly Gln Pro Pro
        35                  40                  45

Lys Leu Leu Ile Lys Tyr Ala Ser Asn Leu Ala Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Asp Thr Ala Thr Tyr Tyr Cys Gln His Ser Trp
                 85                  90                  95

Glu Ile Pro Tyr Thr Phe Gly Gly Gly Thr Lys Leu Glu Ile Lys Arg
             100                 105                 110

Thr Val Ala Ala Pro Ser Val Phe Ile Phe Pro Pro Ser Asp Glu Gln
             115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 110
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-38 antibody

<400> SEQUENCE: 110

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
             20                  25                  30

His Trp Tyr Gln Gln Lys Ser Gly Thr Ser Pro Lys Arg Trp Ile Tyr
         35                  40                  45

Asp Thr Ser Lys Leu Ala Ser Gly Val Pro Ala Arg Phe Ser Gly Gly
 50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                 85                  90                  95

Phe Gly Gly Gly Thr Lys Leu Glu Ile Lys Arg Ala Asp Ala Ala Pro
             100                 105                 110

Thr Val Ser Ile Phe Pro Pro Ser Glu Gln Leu Thr Ser Gly Gly
         115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

```
Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
        210

<210> SEQ ID NO 111
<211> LENGTH: 213
<212> TYPE: PRT
<213> ORGANISM: Artificial Sequence
<220> FEATURE:
<223> OTHER INFORMATION: Full-length light chain amino acid sequences;
      chCD37-38 antibody

<400> SEQUENCE: 111

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
        210

<210> SEQ ID NO 112
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-38 antibody

<400> SEQUENCE: 112

Asp Ile Val Leu Thr Gln Ser Pro Ala Ser Met Ser Ala Ser Pro Gly
1               5                   10                  15

Glu Arg Val Thr Met Thr Cys Ser Ala Ser Ser Ser Val Thr Tyr Met
            20                  25                  30
```

```
His Trp Tyr Gln Gln Lys Pro Gly Thr Ser Pro Lys Arg Trp Ile Tyr
        35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ile Ser Asn Pro Pro Thr
                85                  90                  95

Phe Gly Gly Gly Thr Lys Leu Glu Ile Lys Arg Thr Val Ala Ala Pro
                100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
                180                 185                 190

Cys Glu Val Thr His Gln Gly Leu Ser Ser Pro Val Thr Lys Ser Phe
                195                 200                 205

Asn Arg Gly Glu Cys
    210

<210> SEQ ID NO 113
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-50 antibody

<400> SEQUENCE: 113

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met
                20                  25                  30

His Trp Tyr Gln Gln Lys Ser Gly Thr Ser Pro Lys Arg Trp Ile Tyr
        35                  40                  45

Asp Thr Ser Lys Leu Pro Tyr Gly Val Pro Gly Arg Phe Ser Gly Ser
        50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg Ala Asp Ala Ala Pro
                100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
```

165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 114
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-50 antibody

<400> SEQUENCE: 114

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Asn Leu Pro Tyr Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 115
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-51 antibody

<400> SEQUENCE: 115

Gln Ile Val Leu Thr Gln Ser Pro Ala Ile Met Ser Ala Ser Pro Gly
1               5                   10                  15

Glu Lys Val Thr Met Thr Cys Ser Ala Thr Ser Ser Val Thr Tyr Met

```
                 20                  25                  30

His Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Asn Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Glu Gln Leu Thr Ser Gly Gly
            115                 120                 125

Ala Ser Val Val Cys Phe Leu Asn Asn Phe Tyr Pro Lys Asp Ile Asn
        130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
        210

<210> SEQ ID NO 116
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-51 antibody

<400> SEQUENCE: 116

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Lys Arg Trp Ile Tyr
        35                  40                  45

Asp Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
            115                 120                 125

Ala Ser Val Val Cys Leu Leu Asn Asn Phe Tyr Pro Arg Glu Ala Lys
        130                 135                 140

Val Gln Trp Lys Val Asp Asn Ala Leu Gln Ser Gly Asn Ser Gln Glu
145                 150                 155                 160
```

```
Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
            195                 200                 205

Asn Arg Gly Glu Cys
    210

<210> SEQ ID NO 117
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-56 antibody

<400> SEQUENCE: 117

Gln Ile Val Leu Thr Gln Ser Pro Ala Phe Met Ser Ala Ser Pro Gly
1               5                   10                  15

Asp Lys Val Thr Met Thr Cys Ser Ala Ser Ser Ser Val Thr Tyr Met
            20                  25                  30

His Trp Tyr Gln Gln Lys Ser Gly Thr Ser Pro Lys Arg Trp Ile Tyr
        35                  40                  45

Asp Thr Ser Lys Leu Ala Ser Gly Val Pro Ala Arg Phe Ser Gly Gly
    50                  55                  60

Gly Ser Gly Thr Ser Tyr Ser Leu Thr Ile Ser Thr Met Glu Ala Glu
65                  70                  75                  80

Asp Ala Ala Thr Tyr Tyr Cys Gln Gln Trp Ile Ser Asp Pro Pro Thr
                85                  90                  95

Phe Gly Gly Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
            115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
            195                 200                 205

Asn Arg Asn Glu Cys
    210

<210> SEQ ID NO 118
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-56 antibody

<400> SEQUENCE: 118

Asp Ile Val Leu Thr Gln Ser Pro Ala Phe Met Ser Ala Ser Pro Gly
1               5                   10                  15
```

```
Glu Lys Val Thr Met Thr Cys Ser Ala Ser Ser Val Thr Tyr Met
                20                  25                  30

His Trp Tyr Gln Gln Lys Pro Asp Gln Ser Pro Lys Arg Trp Ile Tyr
            35                  40                  45

Asp Thr Ser Asn Leu Ala Ser Gly Val Pro Ser Arg Phe Ser Gly Gly
        50                  55                  60

Gly Ser Gly Thr Asp Tyr Ser Leu Thr Ile Ser Ser Met Glu Ala Glu
 65                  70                  75                  80

Asp Ala Ala Thr Tyr Tyr Cys Gln Gln Trp Ile Ser Asp Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 119
<211> LENGTH: 213
<212> TYPE: PRT
<213> ORGANISM: Artificial Sequence
<220> FEATURE:
<223> OTHER INFORMATION: Full-length light chain amino acid sequences;
      muCD37-57 antibody

<400> SEQUENCE: 119

Gln Ile Val Leu Thr Gln Ser Pro Ala Ile Met Ser Ala Ser Pro Gly
 1                5                  10                  15

Glu Lys Val Thr Met Thr Cys Ser Ala Thr Ser Ser Val Thr Tyr Met
                20                  25                  30

His Trp Tyr Gln Gln Lys Ser Gly Thr Ser Pro Lys Arg Trp Ile Tyr
            35                  40                  45

Asp Thr Ser Lys Leu Ala Ser Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Asp Asn Pro Pro Thr
                85                  90                  95

Phe Gly Ser Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
    130                 135                 140

Val Lys Trp Lys Ile Asp Gly Ser Glu Arg Gln Asn Gly Val Leu Asn
145                 150                 155                 160
```

```
Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 120
<211> LENGTH: 213
<212> TYPE: PRT
<213> ORGANISM: Artificial Sequence
<220> FEATURE:
<223> OTHER INFORMATION: Full-length light chain amino acid sequences;
      huCD37-57 antibody

<400> SEQUENCE: 120

Glu Ile Val Leu Thr Gln Ser Pro Ala Thr Met Ser Ala Ser Pro Gly
1               5                   10                  15

Glu Arg Val Thr Met Thr Cys Ser Ala Thr Ser Ser Val Thr Tyr Met
            20                  25                  30

His Trp Tyr Gln Gln Lys Pro Gly Gln Ser Pro Arg Arg Trp Ile Tyr
        35                  40                  45

Asp Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Asp Asn Pro Pro Thr
                85                  90                  95

Phe Gly Gln Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 121
<211> LENGTH: 5
<212> TYPE: PRT
<213> ORGANISM: Artificial Sequence
<220> FEATURE:
<223> OTHER INFORMATION: Variable heavy chain CDR amino acid sequence;
      Antibody CD37-3, VH-CDR1

<400> SEQUENCE: 121

Thr Ser Gly Val Ser
1               5
```

<210> SEQ ID NO 122
<211> LENGTH: 9
<212> TYPE: PRT
<213> ORGANISM: Artificial Sequence
<220> FEATURE:
<223> OTHER INFORMATION: Variable heavy chain CDR amino acid sequence;
      Antibody CD37-3, VH-CDR2

<400> SEQUENCE: 122

Val Ile Trp Gly Asp Gly Ser Thr Asn
1               5

<210> SEQ ID NO 123
<211> LENGTH: 7
<212> TYPE: PRT
<213> ORGANISM: Artificial Sequence
<220> FEATURE:
<223> OTHER INFORMATION: Variable heavy chain CDR amino acid sequence;
      Antibody CD37-3, VH-CDR3

<400> SEQUENCE: 123

Gly Gly Tyr Ser Leu Ala His
1               5

<210> SEQ ID NO 124
<211> LENGTH: 5
<212> TYPE: PRT
<213> ORGANISM: Artificial Sequence
<220> FEATURE:
<223> OTHER INFORMATION: Variable heavy chain CDR amino acid sequence;
      Antibody CD37-12, VH-CDR1

<400> SEQUENCE: 124

Lys Tyr Gly Met Asn
1               5

<210> SEQ ID NO 125
<211> LENGTH: 10
<212> TYPE: PRT
<213> ORGANISM: Artificial Sequence
<220> FEATURE:
<223> OTHER INFORMATION: Variable heavy chain CDR amino acid sequence;
      Antibody CD37-12, VH-CDR2

<400> SEQUENCE: 125

Trp Ile Asn Thr Asn Thr Gly Glu Ser Arg
1               5                   10

<210> SEQ ID NO 126
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Antibody CD37-12, VH-CDR3

<400> SEQUENCE: 126

Gly Thr Val Val Ala Asp
1               5

<210> SEQ ID NO 127
<211> LENGTH: 6
<212> TYPE: PRT
<213> ORGANISM: Artificial Sequence
<220> FEATURE:
<223> OTHER INFORMATION: Variable heavy chain CDR amino acid sequence;
      Antibody CD37-38, VH-CDR1

<400> SEQUENCE: 127

Ser Gly Phe Gly Trp His
1               5